(12) United States Patent
Ok et al.

(10) Patent No.: US 9,771,453 B2
(45) Date of Patent: *Sep. 26, 2017

(54) PROCESS OF PRODUCING POLYCARBONATE BY COPOLYMERIZATION OF CARBON DIOXIDE AND EPOXIDE USING THE SAME AS CATALYST

(71) Applicant: SK INNOVATION CO., LTD., Seoul (KR)

(72) Inventors: Myungahn Ok, Daejeon (KR); Jisu Jeong, Daejeon (KR); BunYeoul Lee, Gyeonggi-do (KR); Sujith S., Gyeonggi-do (KR); Anish Cyriac, Gyeonggi-do (KR); JaeKi Min, Gyeonggi-do (KR); JongEon Seong, Incheon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,988

(22) Filed: Nov. 16, 2015

(65) Prior Publication Data

US 2016/0075824 A1 Mar. 17, 2016

Related U.S. Application Data

(62) Division of application No. 14/164,355, filed on Jan. 27, 2014, now Pat. No. 9,217,057, which is a division of application No. 13/411,917, filed on Mar. 5, 2012, now Pat. No. 8,642,721, which is a division of application No. 12/458,998, filed on Jul. 29, 2009, now abandoned.

(30) Foreign Application Priority Data

| Jul. 30, 2008 | (KR) | 10-2008-0074435 |
|---|---|---|
| Dec. 11, 2008 | (KR) | 10-2008-0126170 |
| Jun. 18, 2009 | (KR) | 10-2009-0054481 |
| Jun. 18, 2009 | (KR) | 10-2009-0054569 |

(51) Int. Cl.

| C08G 64/34 | (2006.01) |
|---|---|
| C07C 251/24 | (2006.01) |
| C07C 37/16 | (2006.01) |
| C07C 39/24 | (2006.01) |
| C07C 45/63 | (2006.01) |
| C07C 45/68 | (2006.01) |
| C07F 15/06 | (2006.01) |
| C07C 45/00 | (2006.01) |
| C07C 249/02 | (2006.01) |

(52) U.S. Cl.
CPC .............. *C08G 64/34* (2013.01); *C07C 37/16* (2013.01); *C07C 39/24* (2013.01); *C07C 45/00* (2013.01); *C07C 45/63* (2013.01); *C07C 45/68* (2013.01); *C07C 249/02* (2013.01); *C07C 251/24* (2013.01); *C07F 15/065* (2013.01); *C07C 2601/14* (2017.05)

(58) Field of Classification Search
None
See application file for complete search history.

(56) References Cited

U.S. PATENT DOCUMENTS 2,073,995 A   3/1937 Raiziss et al.

FOREIGN PATENT DOCUMENTS

| DE | 102005054770 A1 | 5/2007 |
|---|---|---|
| JP | 60-97990 | 5/1985 |
| JP | 04-296767 | 10/1992 |
| JP | 2012-254989 | 12/2012 |
| KR | 10-2007-0043417 | 5/2007 |
| KR | 10-2008-0015454 | 2/2008 |
| WO | 2008/136591 | 11/2008 |

OTHER PUBLICATIONS

Nakano et al. Angew. Chem. Int. Ed. 2006, 45, 7274-7277.*
E. Noh et al., "Two Components in a Molecule: Highly Efficient and Thermally Robust Catalytic System for $CO_2$/Epoxide Copolymerization", *J. Am. Chem. Soc.* 2007, 129, 8082-8083.
S. S et al., "A Highly Active and Recyclable Catalytic System for $CO_2$/Propylene Oxide Copolymerization", *Angew, Chem. Int. Ed.* 2008, 47, 7306-7309.
X. Lu et al., "Design of Highly Active Binary Catalyst Systems for $CO_2$/Epoxide Copolymerization: Polymer Selectivity, Enantioselectivity, and Stereochemistry Control", *J. Am. Chem. Soc.* 2006, 128, 1664-1674.
C. Cohen et al., "Copolymerization of cyclohexene oxide and carbon dioxide using (salen)Co(III) complexes: synthesis and characterization of syndiotactic poly(cyclohexene carbonate)", The Royal Society of Chemistry, *Dalton Trans.*, 2006, 237-249.
R. Paddock et al., "Alternating Copolymerization of $CO_2$ and Propylene Oxide Catalyzed by $Co^{III}$(salen)/Lewis Base", *Macromolecules* 2005, 38, 6251-6253.
D. Darensbourg et al., "Copolymerization of $CO_2$ and Epoxides Catalyzed by Metal Salen Complexes", *Acc. Chem. Res.* 2004, 37, 836-844.
D. Darensbourg et al., "Role of the Cocatalyst in the Copolymerization of $CO_2$ and Cyclohexene Oxide Utilizing Chromium Salen Complexes", *J. Am. Chem. Soc.* 2005, 127, 14026-14038.

(Continued)

*Primary Examiner* — Yun Qian
(74) *Attorney, Agent, or Firm* — Clark & Brody

(57) ABSTRACT

Provided are a complex prepared from ammonium salt-containing ligands and having such an equilibrium structural formula that the metal center takes a negative charge of 2 or higher, and a method for preparing polycarbonate via copolymerization of an epoxide compound and carbon dioxide using the complex as a catalyst. When the complex is used as a catalyst for copolymerizing an epoxide compound and carbon dioxide, it shows high activity and high selectivity and provides high-molecular weight polycarbonate, and thus easily applicable to commercial processes. In addition, after forming polycarbonate via carbon dioxide/epoxide copolymerization using the complex as a catalyst, the catalyst may be separately recovered from the copolymer.

3 Claims, 6 Drawing Sheets

(56) References Cited

OTHER PUBLICATIONS

C. Tagusagawa et al., "Efficient Utilization of Nanospace of Layered Transition Metal Oxide $HNbMoO_6$ as a Strong, Water-Tolerant Solid Acid Catalyst", *J. Am. Chem. Soc.* 2008, 130, 7230-7231.

C. Becker et al., "Ligand Subsititution Reactions in Tetrakis(Benzylisocyanide)-bis(Tri-p-Tolyarsine Oxide)Cobalt(III) Tetrafluoroborate: An Example of a Labile Six-Coordinate Cobalt(III) Complex", *Synth. React. Inorg. Met.-Org. Chem.* 31(9), 1545-1552 (2001).

T. Collins et al., "Paramagnetic Cobalt(III) Complexes of Polyanionic Chelating Ligands", *J. Am. Chem. Soc.* 1986, 108, 2088-2090.

H. Gray et al., "The Electronic Structures of Square-Planar Metal Complexes. III. High-Spin Planar Cobalt(I) and Iron(I)", *J. Am. Chem. Society* 1963, 85, 2019-2020.

C. Langford et al., "Interconvertible Four-, Five-, and Six-Coordinate Cobalt Complexes", *J. Am. Chem. Soc.* 1986, 2958-2959.

J. Park et al., "Self-Assembled Dinuclear Cobalt(II)-Salen Catalyst Through Hydrogen-Bonding and Its Application to Enantioselective Nitro-Aldol (Henry) Reaction", *J. Am. Chem. Soc.* 2008, 130, 16484-16485.

K. Neuvonen et al., "Comparison of the Electronic Structures of Imine and Hydrazone Side-Chain Functionalities with the Aid of $^{13}C$ and $^{15}N$ NMR Chemical Shifts and PM3 Calculations. The Influence of C=N-Substitution on the Sensitivity to Aromatic Substitution", *J. Org. Chem.*, 2003, 68, 2151-2160.

T. Wood et al., "$^{15}N$ NMR Chemical Shifts for the Identification of Dipyrrolic Structures", *J. Org. Chem.* 2006, 71, 2964-2971.

E. Konig et al., "Magnetismn Down to 1.00 K and the Ligand Field in a Series of Paramagnetic, Five-Coordinate Cobalt(III) Complexes, Halogeno-N,N'(1,2-Propylene)-bis(o-Aminobenzylideniminato)Cobalt(III)", *Chemical Physics* 34 (1978) 379-389.

S. Kemper et al., "Jacobsen's Catalyst for Hydrolytic Kinetic Resolution: Structure Elucidation of Paramagnetic Co(III) Salen Complexes in Solution via Combined NMR and Quantum Chemical Studies", *J. Am. Chem. Soc.* 2009, 131, 4172-4173.

T. Yagi et al., "Structural and spectroscopic comparisons of the square-planar four-coordinate [o-phenylenebis(biuretato)]cobaltate(III) complex and the five-coordinate mono-and six-coordinate dicyano adducts", *J. Chem. Soc., Dalton Trans.*, 2002, 1126-1131.

M. Fujita et al., "Optically Active Coordination Compounds-XLVII.* Synthesis, Resolution and Interconversions of Isomers of Tris-Salicylatocobaltate(III)", *Polyhedron* vol. 7, No. 24, pp. 2731-2742, 1988.

A. Streitwieser, Jr. et al., "Acidity of Hydrocarbons. XLII. Effect of Temperature on the Absoption Spectra of Some Lithium and Cesium Salts of Carbanions in Amine Solvents[1]", *J. Am. Chem. Soc.* 1972, 5288-5291.

T. Hogen-Esch et al., "Studies of Contact and Solvent-Separated Ion Pairs of Carbanions. I. Effect of Temperature, Counterion, and Solvent", *J. Am. Chem. Soc.* 88, 2, 1966, 307-318.

J. Lu et al., ""Separated" versus "Contact" Ion-Pair Structures in Solution from Their Crystalline States: Dynamic Effects on Dinitrobenzenide as a Mixed-Valence Anion", *J. Am. Chem. Soc.* 2005, 127, 1797-1809.

E. Fendler et al., "Intermediates in Nucleophilic Aromatic Substitution. IV.[1] Structures and Stabilities of Spiro Meisenheimer Complexes of Dinitro-Substituted Arenes[2]", *J. Org. Chem.* vol. 33, No. 11, Nov. 1968, pp. 4141-4145.

C. Bernasconi et al., "Intermediates in Nuceleophilic Aromatic Substitution. XII.[1] Kinetic and Equilibrium Study of the Spiro Meisenheimer Complex of 1-(β-Hydroxyethoxy)-2,4-dinitrobenzene", *J. Org. Chem.* vol. 39, No. 8, 1974.

JACS, 2007, 129 pp. 8082-8083, published on web Jun. 5, 2007.

Sujith S. et al., "A Highly Active . . . Oxide Coplymerization", Angewandte Chemie, Wiley, vol. 120, No. 38, Sep. 8, 2008, pp. 7416-7419.

Min et al., Bull. Korean Chem. Soc. 2009, 30(3), 745.

* cited by examiner

PROCESS OF PRODUCING POLYCARBONATE BY COPOLYMERIZATION OF CARBON DIOXIDE AND EPOXIDE USING THE SAME AS CATALYST

This application is a Divisional of U.S. Ser. No. 14/164,355 filed on Jan. 27, 2014, which is a Divisional of U.S. Ser. No. 13/411,917 filed on Mar. 5, 2012, which is now U.S. Pat. No. 8,642,721, issued on Feb. 4, 2014, which is a Divisional of Abandoned U.S. Ser. No. 12/458,998, filed on Jul. 29, 2009.

TECHNICAL FIELD

The present invention relates to a novel catalyst for use in preparing polycarbonate from an epoxide compound and carbon dioxide and a method for preparing polycarbonate using the same. More particularly, the present invention relates to a catalyst for preparing the above polymer, which includes a complex having such an equilibrium structural formula that the metal center of the complex takes a negative charge of 2 or higher, as well as to a method for preparing polycarbonate via copolymerization of carbon dioxide and epoxide using the same complex as a catalyst. In addition, the present invention relates to a method including carrying out polymerization using the above catalyst, and separately recovering the catalyst from the solution in which the resultant copolymer and the catalyst are dissolved.

BACKGROUND ART

Aliphatic polycarbonate is an easily biodegradable polymer and is useful for packaging or coating materials, etc. Processes for preparing polycarbonate from an epoxide compound and carbon dioxide is highly eco-friendly in that they use no harmful compound, phosgene, and adopt easily available and inexpensive carbon dioxide.

Since 1960's, many researchers have developed various types of catalysts to prepare polycarbonate from an epoxide compound and carbon dioxide. Recently, we have developed a catalyst for carrying out carbon dioxide/epoxide copolymerization. The catalyst includes a complex having an onium salt and a metal center with a Lewis acid group in one molecule. Use of the catalyst allows the growth point of the polymer chain to be positioned always in the vicinity of the metal in the polymerization medium for carrying out epoxide/carbon dioxide copolymerization, regardless of the concentration of the catalyst. In this manner, the catalyst shows high activity even under a high ratio of monomer/catalyst, exhibits high cost-efficiency by virtue of a decrease in catalyst need, and provides polycarbonate with a high molecular weight. Moreover, the catalyst realizes polymerization activity even at high temperature to increase the conversion, permits easy removal of the polymerization reaction heat, and thus is easily applicable to commercial processes [see, Korean Patent Application No. 10-2007-0043417 (May 4, 2007, Title: COORDINATION COMPLEXS CONTAINING TWO COMPONENTS IN A MOLECULE AND PROCESS OF PRODUCING POLYCARBONATE BY COPOLYMERIZATION OF CARBON DIOXIDE AND EPOXIDE USING THE SAME); International Patent Application No. PCT/KR2008/002453; Eun Kyung Noh, Sung Jae Na, Sujith S, Sang-Wook Kim, and Bun Yeoul Lee* *J. Am. Chem. Soc.* 2007, 129, 8082-8083 (2007 Jul. 4)]. Further, when the complex having an onium salt and a metal center with a Lewis acid group in one molecule is used as a catalyst for carbon dioxide/epoxide copolymerization, the catalyst is easily separated and reutilized from the copolymer after the polymerization. Thus, such a method for separately recovering the catalyst has been described in a patent application and a journal [Korean Patent Application No. 10-2008-0015454 (Feb. 20, 2008, Title: METHOD FOR RECOVERING CATALYST FROM PROCESS FOR PREPARING COPOLYMER); Bun Yeol Lee, Sujith S, Eun Kyung Noh, Jae Ki Min, "A PROCESS PRODUCING POLYCARBONATE AND A COORDINATION COMPLEXES USED THEREFOR" PCT/KR2008/002453 (2008 Apr. 30); Sujith S, Jae Ki Min, Jong Eon Seong, Sung Jea Na, and Bun Yeoul Lee* "A HIGHLY ACTIVE AND RECYCLABLE CATALYTIC SYSTEM FOR CO$_2$/(PROPYLENE OXIDE) COPOLYMERIZATION" *Angew. Chem. Int. Ed.,* 2008, 47, 7306-7309].

The complex of the above studies mainly includes Salen-cobalt compound ([H$_2$Salen=N,N'-bis(3,5-dialkylsalicylidene)-1,2-cyclohexanediamine]) (see the following chemical formula), obtained from a Schiff base ligand of a salicylaldehyde compound and a diamine compound. The complex is a tetradentate (or quadradendate) cobalt compound-based complex in which trivalent cobalt atom is coordinated with two nitrogen imine ligands and two phenolate ligands at the same time:

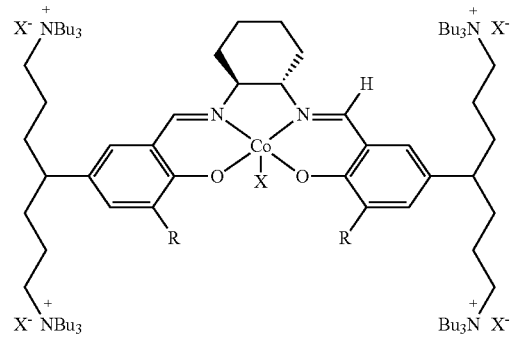

X = 2,4-dinitrophenolate

The complex may be referred to as a tetradentate (or quadradendate) Schiff base complex, and may be prepared according to the following reaction scheme:

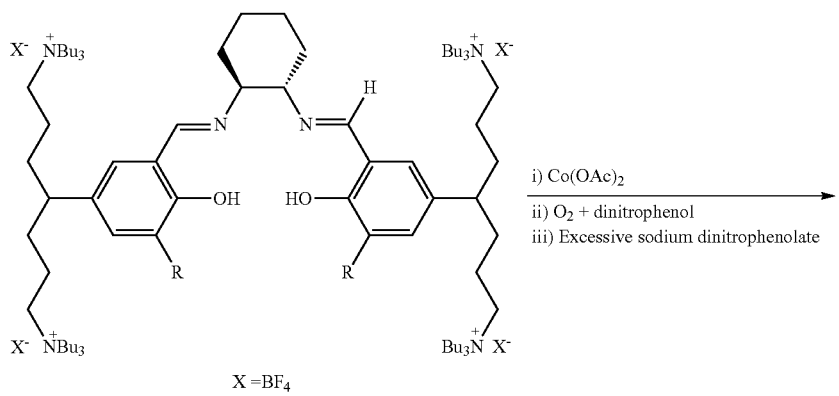

The above tetradentate (or quadradentate) Schiff-base cobalt or chrome complex has been developed intensively as a carbon dioxide/epoxide copolymerization catalyst. (Cobalt-based catalyst: (a) Lu, X.-B.; Shi, L.; Wang, Y.-M.; Zhang, R.; Zhang, Y.-J.; Peng, X.-J.; Zhang, Z.-C.; Li, B. *J. Am. Chem. Soc.* 2006, 128, 1664. (b) Cohen, C. T. Thomas, C. M. Peretti, K. L. Lobkovsky, E. B. Coates, G. W. *Dalton Trans.* 2006, 237. (c) Paddock, R. L. Nguyen, S. T. *Macromolecules* 2005, 38, 6251. Chrome-based catalyst: (a) Darensbourg, D. J.; Phelps, A. L.; Gall, N. L.; Jia, L. *Acc. Chem. Res.* 2004, 37, 836. (b) Darensbourg, D. J.; Mackiewicz, R. M. *J. Am. Chem. Soc.* 2005, 127, 14026.).

DISCLOSURE

Technical Problem

We have studied about the characteristics and structures of the tetradentate (or quadradentate) complex having the above described structure and unexpectedly found that the complex shows significantly different activities and selectivities depending on the R group. In order word, when R is a sterically hindered group such as t-butyl, the compound shows commonly expectable activity and selectivity. However, when R has decreased steric hindrance, or R is a radical such as methyl, the complex provides an activity (TOF, turnover frequency) of 26000 h$^{-1}$, which is about 20 times higher than the activity (1300 h$^{-1}$) of the corresponding t-butyl group-containing complex. In addition, the methyl group-containing complex provides an increase in selectivity from 84% to 99% or higher. Based on these findings, we have conducted several types of structural analysis including $^1$H MNR, $^{13}$C MNR, $^{15}$N MNR, $^{19}$F NMR, IR, IAP-AES, elemental analysis, electrochemical analysis, etc. As a result, we have found that when R is a less sterically hindered radical, such as methyl, another complex (i.e. bidentate complex) having a different structure in which the metal is not coordinated with the adjacent nitrogen is obtained, and the complex has high activity and selectivity.

Therefore, an object of the present invention is to provide a method for copolymerizing carbon dioxide and epoxide using a complex coordinated with monodentate, bidentate or tridentate ligands having at least one protonated group rather than the existing tetradentate (or quadradentate) complex.

Another object of the present invention is to provide a method for the formation of a copolymer using the above complex as a catalyst, and for the separation and recovery of the catalyst from the mixed solution of the resultant copolymer and the catalyst.

Still another object of the present invention is to provide the above-described novel complex.

Technical Solution

To achieve the object of the present invention, the present invention provides a novel complex coordinated with monodentate, bidentate or tridentate ligands having at least one protonated group, and a method for preparing a carbon dioxide/epoxide copolymer using the same complex as a catalyst.

Hereinafter, the present invention will be explained in more detail.

The present invention provides a novel complex as a catalyst for preparing a carbon dioxide/epoxide copolymer. The complex is coordinated with monodentate, bidentate or tridentate ligands having at least one protonated group. The complex is represented by Chemical Formula 1:

$$[L_aMX_b]X_c \qquad \text{[Chemical Formula 1]}$$

wherein

M represents a metal element;

L represents a L-type or X-type ligand;

a represents 1, 2 or 3, wherein when a is 1, L includes at least two protonated groups, and when a is 2 or 3, L(s) are the same or different, and may be linked to each other to be chelated to the metal as a bidentate or tridentate ligand, with the proviso that at least one L includes at least one protonated group and the total number of protonated groups contained in L(s) is 2 or more;

X(s) independently represent a halide ion; $BF_4^-$; $ClO_4^-$; $NO_3^-$; $PF_6^-$; $HCO_3^-$; or a (C6-C20)aryloxy anion; (C1-C20) alkylcarboxy anion; (C1-C20)alkoxy anion; (C1-C20)alkylcarbonate anion; (C1-C20)alkylsulfonate anion; (C1-C20) alkylamide anion; (C1-C20)alkylcarbamate anion; or anion of Meisenheimer salt with or without at least one of halogen, nitrogen, oxygen, silicon, sulfur and phosphorus atoms; and b and c satisfy the condition of "(b+c)=(total number of protonated groups contained in L)+[(oxidation number of metal)−(number of X-type ligands in L)]".

The anion of Meisenheimer salt is a compound having the following structural formula:

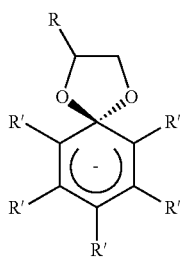

wherein

R represents methyl or H; and

R' is selected from H and nitro (—NO$_2$), with the proviso that at least one of the five R' radicals represents nitro (—NO$_2$).

In Chemical Formula 1, L-type and X-type ligands are described in detail in [Gray L. Spessard and Gary L. Miessler, Organometallic Chemistry, published by Prentice Hall, p. 46]. L-type ligands mean neutral ligands and particularly include non-paired electron pair donors, such as phosphine, pi-bond donors, such as ethylene, or sigma-bond donors, such as hydrogen. L-type ligands are bound to the metal by donating non-paired electron pairs, and binding of the L-type ligands has no effect on the oxidation number of the metal. X-type ligands include anionic ligands, such as chlorine or methyl. Binding of such X-type ligands is regarded as binding between X$^-$ anion and M$^+$ cation, and affects the oxidation number of the metal.

The complex used as a carbon dioxide/epoxide copolymerization catalyst herein is a complex coordinated with monodentate, bidentate or tridentate ligands having at least one protonated group (i.e. complex represented by Chemical Formula 1), and having such an equilibrium structural formula that the metal center takes a negative charge of 2 or higher. The carbon dioxide/epoxide copolymerization catalysts developed to date are tetradentate (or quadradentate) Schiff-base complexes wherein "four groups are bound to one metal atom", and thus are clearly different from the complex disclosed herein.

According to one embodiment of the present invention, there is provided a complex represented by Chemical Formula 1, wherein the protonated group contained in L represents a functional group represented by Chemical Formula 2a, 2b or 2c, and M represents cobalt (III) or chromium (III):

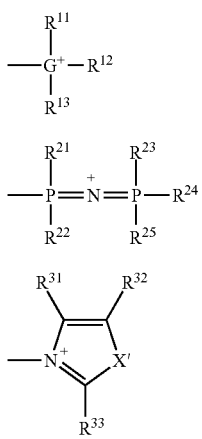

[Chemical Formula 2a]

[Chemical Formula 2b]

[Chemical Formula 2c]

wherein

G represents a nitrogen or phosphorus atom;

$R^{11}$, $R^{12}$, $R^{13}$, $R^{21}$, $R^{22}$, $R^{23}$, $R^{24}$ and $R^{25}$ independently represent a (C1-C20)alkyl, (C2-C20)alkenyl, (C1-C15)alkyl(C6-C20)aryl or (C6-C20)aryl(C1-C15)alkyl radical with or without at least one of halogen, nitrogen, oxygen, silicon, sulfur and phosphorus atoms; or a hydrocarbyl-substituted metalloid radical of a Group 14 metal, wherein two of $R^{11}$, $R^{12}$ and $R^{13}$, or two of $R^{21}$, $R^{22}$, $R^{23}$, $R^{24}$ and $R^{25}$ may be linked to each other to form a ring;

$R^{31}$, $R^{32}$ and $R^{33}$ independently represent a hydrogen radical; (C1-C20)alkyl, (C2-C20)alkenyl, (C1-C15)alkyl(C6-C20)aryl or (C6-C20)aryl(C1-C15)alkyl radical with or without at least one of halogen, nitrogen, oxygen, silicon, sulfur and phosphorus atoms; or a hydrocarbyl-substituted metalloid radical of a Group 14 metal, wherein two of $R^{31}$, $R^{32}$ and $R^{33}$ may be linked to each other to form a ring;

X' represents an oxygen atom, sulfur atom or N—R (wherein R represents a hydrogen radical; or a (C1-C20)alkyl, (C2-C20)alkenyl, (C1-C15)alkyl(C6-C20)aryl or (C6-C20)ar(C1-C15)alkyl radical with or without at least one of halogen, nitrogen, oxygen, silicon, sulfur and phosphorus atoms; and the alkyl of the alkyl, alkenyl, alkylaryl or aralkyl radicals may be linear or branched.

According to another embodiment of the present invention, there is provided a complex represented by Chemical Formula 1, wherein L represents a ligand represented by Chemical Formula 3, a represents 2 or 3, and M represents cobalt (III) or chromium (III):

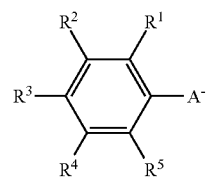

[Chemical Formula 3]

wherein

A represents an oxygen or sulfur atom;

$R^1$ through $R^5$ independently represent a hydrogen radical; linear or branched (C1-C20)alkyl, (C2-C20)alkenyl, (C1-C15)alkyl(C6-C20)aryl or (C6-C20)aryl(C1-C15)alkyl radical with or without at least one of halogen, nitrogen, oxygen, silicon, sulfur and phosphorus atoms; or a hydrocarbyl-substituted metalloid radical of a Group 14 metal, wherein the alkyl or alkenyl of $R^3$ may be further substituted by a (C1-C15)alkyl(C6-C20)aryl or (C6-C20)aryl(C1-C15)alkyl, two of $R^1$ through $R^5$ may be linked to each other to form a ring, and at least one of $R^1$ through $R^5$ include at least one of Chemical Formulas 2a to 2c;

a represents 2 or 3; and

L(s) are the same or different and may be linked to each other to be chelated to the metal as a bidentate or tridentate ligand.

According to still another embodiment of the present invention, there is provided a complex having two ligands L represented by Chemical Formula 4:

[Chemical Formula 4]

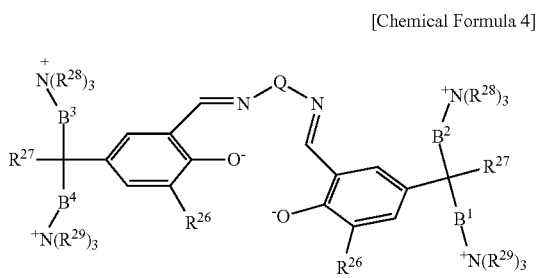

wherein $B^1$ through $B^4$ independently represent (C2-C20)alkylene or (C3-C20)cycloalkylene;

$R^{26}$ represents primary or secondary (C1-C20)alkyl;

$R^{27}$ through $R^{29}$ are independently selected from (C1-C20)alkyl and (C6-C30)aryl;

Q represents a divalent organic bridge group for linking the two nitrogen atoms with each other; and the alkylene or alkyl may be linear or branched.

More particularly, in Chemical Formula 4, Q represents (C6-C30)arylene, (C1-C20)alkylene, (C2-C20)alkenylene, (C2-C20)alkynylene, (C3-C20)cycloalkylene or fused (C3-C20)cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N.

Preferably, in Chemical Formula 4, $B^1$ through $B^4$ independently represent propylene, $R^{26}$ and $R^{27}$ independently represent methyl, $R^{28}$ and $R^{29}$ independently represent butyl, and Q represents trans-1,2-cyclohexylene.

The ligand represented by Chemical Formula 4 may be formed from a phenol derivative represented by Chemical Formula 14, which is prepared from the reaction between a phenol compound represented by Chemical Formula 15 and substituted by an alkyl group at the C2 position and a tertiary alcohol compound represented by Chemical Formula 16 in the presence of an acid catalyst:

[Chemical Formula 14]

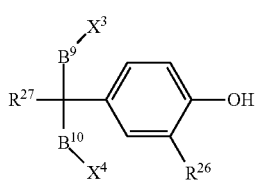

[Chemical Formula 15]

[Chemical Formula 16]

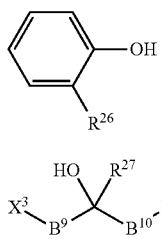

In Chemical Formulas 14 to 16, $B^9$ and $B^{10}$ independently represent (C2-C20)alkylene or (C3-C20)cycloalkylene, preferably propylene. $R^{26}$ represents primary or secondary (C1-C20)alkyl. When $R^{26}$ is a tertiary alkyl, the reaction provides a low yield due to the production of byproducts caused by various side reactions, and thus requires a purification process for removing the byproducts. In addition, cobalt complexes obtained from such a tertiary alkyl-containing phenol compound have a different structure and low activity. Thus, primary or secondary (C1-C20)alkyl is preferred. More particularly, $R^{26}$ represents primary or secondary (C1-C7)alkyl. Herein, the term 'primary alkyl' includes normal alkyl, neo-alkyl or iso-alkyl. The terms 'secondary alkyl' and 'tertiary alkyl' are also referred to as 'sec-alkyl' and 'tert-alkyl', respectively.

$R^{27}$ is selected from (C1-C20)alkyl and (C6-C30)aryl, more particularly (C1-C7)alkyl, and preferably methyl. The term 'alkyl' includes a linear or branched alkyl group.

$X^3$ and $X^4$ is independently selected from Cl, Br and I.

Herein, the term 'aryl' includes an aromatic ring, such as phenyl, naphthyl, anthracenyl or biphenyl, wherein a carbon atom in the aromatic ring may be substituted by a hetero atom, such as N, O and S.

As the acid catalyst, $AlCl_3$ or an inorganic acid, such as phosphoric acid or sulfuric acid, may be used. A solid acid catalyst may be used to permit recycle of the catalyst after the reaction. Particular examples of the solid acid catalyst include Nafion NR50, Amberlyst-15, H—ZSM5, H-Beta, $HNbMoO_6$, or the like (see, Kazunari Domen et. al, *J. AM. CHEM. SOC.* 2008, 130, 7230-7231).

The tertiary alcohol compound represented by Chemical Formula 16 may be prepared by various organic reactions. For example, the tertiary alcohol compound may be obtained according to Reaction Scheme 7:

[Reaction Scheme 7]

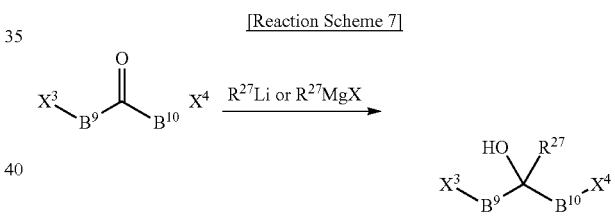

wherein $X^3$, $X^4$ and $R^{27}$ are the same as defined in Chemical Formula 16.

The present invention also provides a ligand compound represented by Chemical Formula 17 prepared from a phenol derivative represented by Chemical Formula 14:

[Chemical Formula 17]

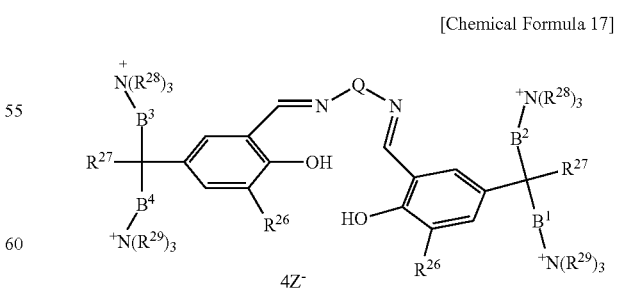

In Chemical Formula 17, $B^1$ through $B^4$ independently represent (C2-C20)alkylene or (C3-C20)cycloalkylene, preferably propylene. The alkylene may be linear or branched.

In Chemical Formula 17, $R^{26}$ represents primary or secondary (C1-C20)alkyl. When $R^{26}$ is tertiary alkyl, the reaction provides a low yield due to the production of byproducts caused by various side reactions, and thus requires a purification process for removing the byproducts. In addition, cobalt complexes obtained from such a tertiary alkyl-containing phenol compound have a different structure and low activity. Thus, primary or secondary (C1-C20)alkyl is preferred. More particularly, $R^{26}$ represents primary or secondary (C1-C7)alkyl. Most preferably, $R^{26}$ represents methyl.

In Chemical Formula 17, $R^{27}$ through $R^{29}$ are independently selected from (C1-C20)alkyl and (C6-C30)aryl groups. More particularly, $R^{27}$ through $R^{29}$ are independently selected from (C1-C7)alkyl groups. Preferably, $R^{27}$ represents methyl and $R^{28}$ and $R^{29}$ independently represent butyl.

In Chemical Formula 17, Q represents a divalent organic bridge group for linking the two nitrogen atoms with each other. Particularly, Q represents (C6-C30)arylene, (C1-C20)alkylene, (C2-C20)alkenylene, (C2-C20)alkynylene, (C3-C20)cycloalkylene or fused (C3-C20)cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N. More particularly, Q is selected from ethylene, trans-1,2-cyclohexylene and 1,2-phenylene.

In Chemical Formula 17, $Z^-$(s) are independently selected from halide ions, $BF_4^-$, $ClO_4^-$, $NO_3^-$, and $PF_6^-$, more particularly iodide ion and $BF_4^-$.

More preferably, the ligand compound represented by Chemical Formula 17 may be a ligand compound represented by Chemical Formula 18:

[Chemical Formula 18]

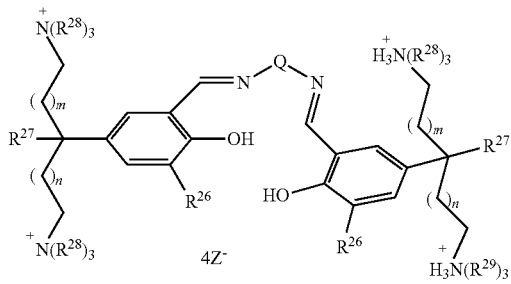

In Chemical Formula 18, m and n independently represent an integer from 1 to 19, preferably from 1 to 5, and more preferably 2.

In Chemical Formula 18, $R^{26}$ represents primary or secondary (C1-C20)alkyl. When $R^{26}$ is a tertiary alkyl, the reaction provides a low yield due to the production of byproducts caused by various side reactions, and thus requires a purification process for removing the byproducts. In addition, cobalt complexes obtained from such a tertiary alkyl-containing compound have a different structure and low activity. Thus, primary or secondary (C1-C20)alkyl is preferred. More particularly, $R^{26}$ represents primary or secondary (C1-C7)alkyl. Most preferably, $R^{26}$ represents methyl.

In Chemical Formula 18, $R^{27}$ through $R^{29}$ are independently selected from (C1-C20)alkyl and (C6-C30)aryl groups. More particularly, $R^{27}$ through $R^{29}$ are independently selected from (C1-C7)alkyl groups. Preferably, $R^{27}$ represents methyl and $R^{28}$ and $R^{29}$ independently represent butyl.

In Chemical Formula 18, Q represents a divalent organic bridge group for linking the two nitrogen atoms with each other. Particularly, Q represents (C6-C30)arylene, (C1-C20)alkylene, (C2-C20)alkenylene, (C2-C20)alkynylene, (C3-C20)cycloalkylene or fused (C3-C20)cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N. More particularly, Q is selected from ethylene, trans-1,2-cyclohexylene and 1,2-phenylene.

In Chemical Formula 18, $Z^-$(s) are independently or simultaneously selected from halide ions, $BF_4^-$, $ClO_4^-$, $NO_3^-$, and $PF_6^-$, more particularly iodide ion and $BF_4^-$.

A method for preparing the compound represented by Chemical Formula 17 or 18 includes:

adding a diamine compound to a compound represented by Chemical Formula 20 to perform imination and to produce a compound represented by Chemical Formula 21; and adding a tertiary amine compound thereto to produce a compound represented by Chemical Formula 17:

[Chemical Formula 20]

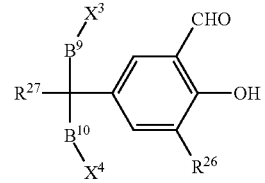

[Chemical Formula 21]

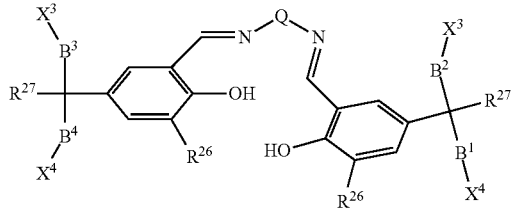

In Chemical Formulas 17, 20 and 21, $B^1$ through $B^4$, $B^9$ and $B^{10}$ independently represent (C2-C20)alkylene or (C3-C20)cycloalkylene, preferably (C2-C6)alkylene, more preferably propylene;

$R^{26}$ represents primary or secondary (C1-C20)alkyl, preferably primary or secondary (C1-C7)alkyl, more preferably methyl;

$R^{27}$ through $R^{29}$ are independently selected from (C1-C20)alkyl and (C6-C30)aryl groups, preferably (C1-C7)alkyl groups. More preferably, $R^{27}$ represents methyl and $R^{28}$ and $R^{29}$ independently represent butyl;

Q represents a divalent organic bridge group for linking the two nitrogen atoms with each other, preferably Q represents (C6-C30)arylene, (C1-C20)alkylene, (C2-C20)alkenylene, (C2-C20)alkynylene, (C3-C20)cycloalkylene or fused (C3-C20)cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N, and more preferably, Q represents trans-1,2-cyclohexylene;

$Z^-$(s) are independently selected from halide ions, $BF_4^-$, $ClO_4^-$, $NO_3^-$ and $PF_6^-$, more particularly iodide ion and $BF_4^-$; and $X^3$ and $X^4$ are independently selected from Cl, Br and I.

The compound represented by Chemical Formula 20 may be prepared by reacting the compound represented Chemical Formula 15 with the compound represented by Chemical Formula 16 in the presence of an acid catalyst to form the compound represented by Chemical Formula 14, and by attaching an aldehyde group at the compound represented by Chemical Formula 14. The acid catalyst may be selected from $AlCl_3$, inorganic acids and solid acid catalysts.

According to one embodiment of the complex represented by Chemical Formula 1, there is provided a complex represented by Chemical Formula 5:

[Chemical Formula 5]

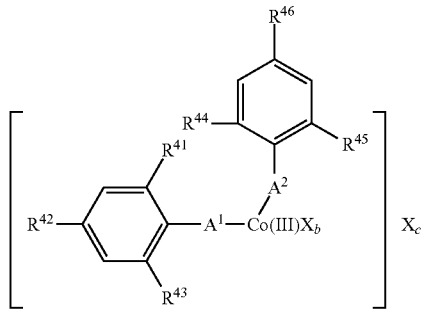

wherein $A^1$ and $A^2$ independently represent an oxygen or sulfur atom;

X(s) independently represent a halide ion; $BF_4^-$; $ClO_4^-$; $NO_3^-$; $PF_6^-$; $HCO_3^-$; or a (C6-C20)aryloxy anion; (C1-C20) alkylcarboxy anion; (C1-C20)alkoxy anion; (C1-C20)alkylcarbonate anion; (C1-C20)alkylsulfonate anion; (C1-C20) alkylamide anion; (C1-C20)alkylcarbamate anion; or anion of Meisenheimer salt with or without at least one of halogen, nitrogen, oxygen, silicon, sulfur and phosphorus atoms;

$R^{41}$, $R^{42}$, $R^{43}$, $R^{44}$, $R^{45}$ and $R^{46}$ are independently selected from H, tert-butyl, methyl, ethyl, isopropyl and $-[YR^{51}_{3-m}\{(CR^{52}R^{53})_nN^+R^{54}R^{55}R^{56}\}_m]$, with the proviso that at least one of $R^{41}$, $R^{42}$, $R^{43}$, $R^{44}$, $R^{45}$ and $R^{46}$ represents $-[YR^{51}_{3-m}\{(CR^{52}R^{53})_nN^+R^{54}R^{55}R^{56}\}_m]$(wherein Y represents a carbon or silicon atom, $R^{51}$, $R^{52}$, $R^{53}$, $R^{54}$, $R^{55}$ and $R^{56}$ independently represent a hydrogen radical; (C1-C20) alkyl, (C2-C20)alkenyl, (C1-C15)alkyl(C6-C20) aryl or (C6-C20)ar(C1-C15)alkyl radical with or without at least one of halogen, nitrogen, oxygen, silicon, sulfur and phosphorus atoms; or a hydrocarbyl-substituted metalloid radical of a Group 14 metal, wherein two of $R^{54}$, $R^{55}$ and $R^{56}$ may be linked to each other to form a ring; m represents an integer from 1 to 3; and n represents an integer from 1 to 20); and b+c−1 represents an integer that equals to the sum of m values of the total $-[YR^{51}_{3-m}\{(CR^{52}R^{53})_nN^+R^{54}R^{55}R^{56}\}_m]$ radicals contained in the complex represented by Chemical Formula 5.

Preferably, in the complex represented by Chemical Formula 5, $R^{41}$, $R^{43}$, $R^{44}$ and $R^{45}$ are independently selected from tert-butyl, methyl, ethyl and isopropyl; $R^{42}$ and $R^{46}$ independently represent $-[CH\{(CH_2)_3N^+Bu_3\}_2]$ or $-[CMe\{(CH_2)_3N^+Bu_3\}_2]$; and b+c represents 5.

According to another embodiment of the complex represented by Chemical Formula 1, there is provided a complex represented by Chemical Formula 6:

[Chemical Formula 6]

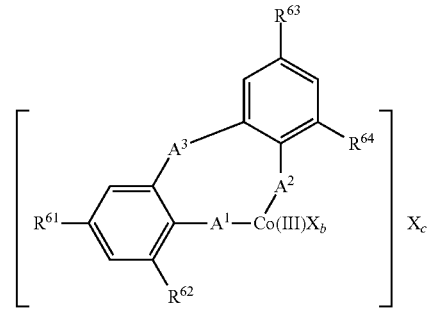

wherein $A^1$ and $A^2$ independently represent an oxygen or sulfur atom;

X(s) independently represent a halide ion; $BF_4^-$; $ClO_4^-$; $NO_3^-$; $PF_6^-$; $HCO_3^-$; or a (C6-C20)aryloxy anion; (C1-C20) alkylcarboxy anion; (C1-C20)alkoxy anion; (C1-C20)alkylcarbonate anion; (C1-C20)alkylsulfonate anion; (C1-C20) alkylamide anion; (C1-C20)alkylcarbamate anion; or anion of Meisenheimer salt with or without at least one of halogen, nitrogen, oxygen, silicon, sulfur and phosphorus atoms;

$R^{62}$ and $R^{64}$ are independently selected from tert-butyl, methyl, ethyl, isopropyl and hydrogen, and $R^{61}$ and $R^{63}$ independently represent $-[YR^{51}_{3-m}\{(CR^{52}R^{53})_nN^+R^{54}R^{55}R^{56}\}_m]$(wherein Y represents a carbon or silicon atom, $R^{51}$, $R^{52}$, $R^{53}$, $R^{54}$, $R^{55}$ and $R^{56}$ independently represent a hydrogen radical; (C1-C20)alkyl, (C2-C20)alkenyl, (C1-C15)alkyl(C6-C20)aryl or (C6-C20)ar(C1-C15)alkyl radical with or without at least one of halogen, nitrogen, oxygen, silicon, sulfur and phosphorus atoms; or a hydrocarbyl-substituted metalloid radical of a Group 14 metal, wherein two of $R^{54}$, $R^{55}$ and $R^{56}$ may be linked to each other to form a ring; m represents an integer from 1 to 3; and n represents an integer from 1 to 20);

b+c−1 represents an integer that equals to 2×m; and $A^3$ represents a chemical bond or divalent organic bridge group for linking the two benzene rings.

More particularly, $A^3$ represents a chemical bond, (C6-C30)arylene, (C1-C20)alkylene, (C2-C20)alkenylene, (C2-C20)alkynylene, (C3-C20)cycloalkylene or fused (C3-C20) cycloalkylene, or $-Si(R^{87})(R^{88})-$, $-CH=N-Q-N=CH-$ or the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N, wherein $R^{87}$ and $R^{88}$ independently represent (C1-C20) alkyl, (C3-C20)cycloalkyl, (C1-C15)alkyl(C6-C20)aryl, or (C6-C20)ar(C1-C15)alkyl, and Q includes a divalent organic bridge group for linking the two nitrogen atoms. Particularly, Q represents (C6-C30)arylene, (C1-C20)alkylene, (C2-C20)alkenylene, (C2-C20)alkynylene, (C3-C20) cycloalkylene or fused (C3-C20)cycloalkylene, wherein the arylene, alkylene, alkenylene, alkynylene, cycloalkylene or fused cycloalkylene may be further substituted by a substituent selected from halogen atoms, (C1-C7)alkyl, (C6-

C30)aryl and nitro groups, or may further include at least one hetero atom selected from O, S and N. Preferably, $R^{61}$ and $R^{63}$ independently represent —[CH{$(CH_2)_3$N+$Bu_3$}$_2$] or —[CMe{$(CH_2)_3$N$^+$Bu$_3$}$_2$], Q in the formula of —CH=N-Q-N=CH— represents trans-1,2-cyclohexylene or ethylene, and X(s) independently represent 2,4-dinitrophenolate or $BF_4^-$.

According to one embodiment of the complex represented by Chemical Formula 6, there is provided a complex represented by Chemical Formula 7:

[Chemical Formula 7]

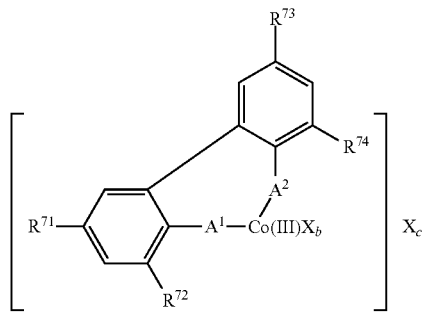

wherein $A^1$ and $A^2$ independently represent an oxygen or sulfur atom;

X(s) independently represent a halide ion; $BF_4^-$; $ClO_4^-$; $NO_3^-$; $PF_6^-$; $HCO_3^-$; or a (C6-C20)aryloxy anion; (C1-C20)alkylcarboxy anion; (C1-C20)alkoxy anion; (C1-C20)alkylcarbonate anion; (C1-C20)alkylsulfonate anion; (C1-C20)alkylamide anion; (C1-C20)alkylcarbamate anion; or anion of Meisenheimer salt with or without at least one of halogen, nitrogen, oxygen, silicon, sulfur and phosphorus atoms;

$R^{72}$ and $R^{74}$ are independently selected from tert-butyl, methyl, ethyl, isopropyl and hydrogen;

$R^{71}$ and $R^{73}$ independently represent —[CH{$(CH_2)_3$N$^+$Bu$_3$}$_2$] or —[CMe{$(CH_2)_3$N$^+$Bu$_3$}$_2$]; and b+c represents 5.

According to another embodiment of the complex represented by Chemical Formula 6, there is provided a complex represented by Chemical Formula 8:

[Chemical Formula 8]

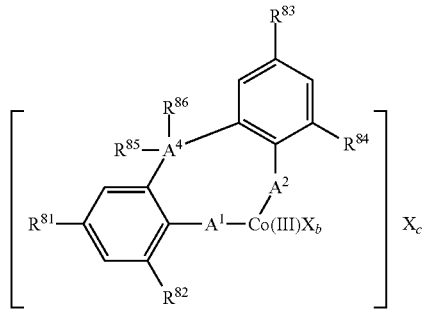

wherein $A^4$ represents a carbon or silicon atom;

$A^1$ and $A^2$ independently represent O or S;

X(s) independently represent a halide ion; $BF_4^-$; $ClO_4^-$; $NO_3^-$; $PF_6^-$; $HCO_3^-$; or a (C6-C20)aryloxy anion; (C1-C20)alkylcarboxy anion; (C1-C20)alkoxy anion; (C1-C20)alkylcarbonate anion; (C1-C20)alkylsulfonate anion; (C1-C20)alkylamide anion; (C1-C20)alkylcarbamate anion; or anion of Meisenheimer salt with or without at least one of halogen, nitrogen, oxygen, silicon, sulfur and phosphorus atoms;

$R^{82}$ and $R^{84}$ are independently selected from tert-butyl, methyl, ethyl, isopropyl and hydrogen;

$R^{81}$ and $R^{83}$ independently represent —[CH{$(CH_2)_3$N$^+$Bu$_3$}2] or —[CMe{$(CH_2)_3$N$^+$Bu$_3$}$_2$]; $R^{85}$ and $R^{86}$ independently represent (C1-C20)alkyl, (C3-C20)cycloalkyl, (C1-C15)alkyl(C6-C20)aryl or (C6-C20)ar(C1-C15)alkyl; and b+c represents 5.

According to still another embodiment of the complex represented by Chemical Formula 6, there is provided a complex represented by Chemical Formula 9:

[Chemical Formula 9]

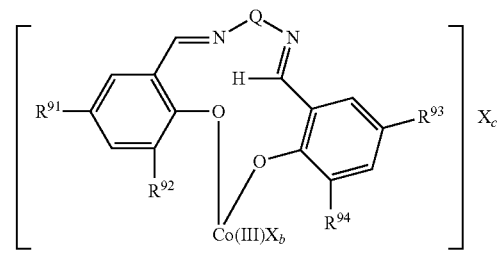

wherein

X(s) independently represent a halide ion; $BF_4^-$; $ClO_4^-$; $NO_3^-$; $PF_6^-$; $HCO_3^-$; or a (C6-C20)aryloxy anion; (C1-C20)alkylcarboxy anion; (C1-C20)alkoxy anion; (C1-C20)alkylcarbonate anion; (C1-C20)alkylsulfonate anion; (C1-C20)alkylamide anion; (C1-C20)alkylcarbamate anion; or anion of Meisenheimer salt with or without at least one of halogen, nitrogen, oxygen, silicon, sulfur and phosphorus atoms;

$R^{92}$ and $R^{94}$ are independently selected from methyl, ethyl, isopropyl and hydrogen, preferably methyl;

$R^{91}$ and $R^{93}$ independently represent —[CH{$(CH_2)_3$N$^+$Bu$_3$}$_2$] or —[CMe{$(CH_2)_3$N$^+$Bu$_3$}$_2$];

Q represents a divalent organic bridge group for linking the two nitrogen atoms;

b+c represents 5; and the alkyl in the alkylcarboxy anion, alkoxy anion, alkylcarbonate anion, alkylsulfonate anion, alkylamide anion and alkylcarbamate anion may be linear or branched.

Preferably, in the complex represented by Chemical Formula 9, Q represents trans-1,2-cyclohexylene or ethylene, and X(s) independently represent 2,4-dinitrophenolate or $BF_4^-$. One of the five X radicals represents $BF_4^-$, two of them represent 2,4-dinitrophenolate, and the remaining two X radicals represent anions represented by Chemical Formula 10:

[Chemical Formula 10]

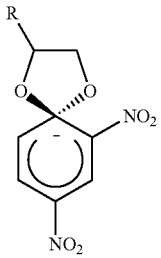

wherein

R represents methyl or H.

According to one embodiment of the complex represented by Chemical Formula 9, there is provided a complex represented by Chemical Formula 11:

[Chemical Formula 11]

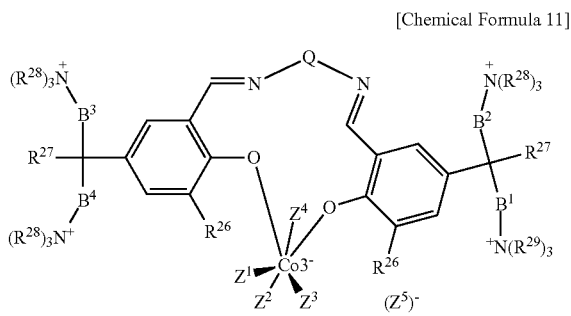

wherein $B^1$ through $B^4$ independently represent (C2-C20)alkylene or (C3-C20)cycloalkylene;

$R^{26}$ represents primary or secondary (C1-C20)alkyl;

$R^{27}$ through $R^{29}$ are independently selected from (C1-C20)alkyl and (C6-C30)aryl;

Q represents a divalent bridge group for linking the two nitrogen atoms;

$Z^1$ through $Z^5$ are independently selected from a halide ion; $BF_4^-$; $ClO_4^-$; $NO_3^-$; $PF_6^-$; $HCO_3^-$; and a (C6-C30) aryloxy anion; (C1-C20)carboxylic acid anion; (C1-C20) alkoxy anion; (C1-C20)alkylcarbonate anion; (C1-C20) alkylsulfonate anion; (C1-C20)alkylamide anion; (C1-C20) alkylcarbamate anion or anion of Meisenheimer salt with or without at least one of halogen, nitrogen, oxygen, silicon, sulfur and phosphorus atoms, wherein a part of $Z^1$ through $Z^4$ coordinated at the cobalt atom may be de-coordinated; and the alkylene and alkyl may be linear or branched.

Preferably, in Chemical Formula 11, Q represents (C6-C30)arylene, (C1-C20)alkylene, (C2-C20)alkenylene, (C2-C20)alkynylene, (C3-C20)cycloalkylene or fused (C3-C20) cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N.

Particularly, in Chemical Formula 11, $B^1$ through $B^4$ independently represent (C2-C6)alkylene, preferably propylene; $R^{26}$ represents (C1-C7)alkyl; $R^{27}$ through $R^{29}$ independently represent (C1-C7)alkyl, preferably $R^{26}$ and $R^{27}$ independently represent methyl, and $R^{28}$ and $R^{29}$ independently represent butyl; Q represents ethylene, trans-1,2-cyclohexylene or 1,2-phenylene, and more preferably trans-1,2-cyclohexylene; and $Z^1$ through $Z^5$ are independently selected from 2,4-dinitrophenolate and $BF_4^-$.

According to one embodiment of the complex represented by Chemical Formula 11, there is provided a complex represented by Chemical Formula 12:

[Chemical Formula 12]

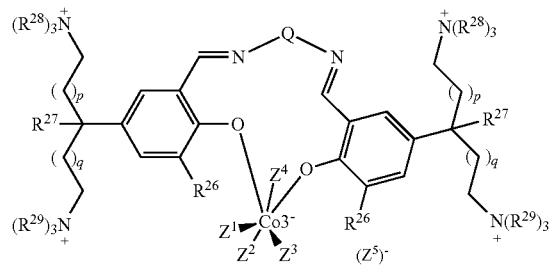

wherein p and q independently represent an integer from 1 to 19;
$R^{26}$ represents primary or secondary (C1-C20)alkyl;
$R^{27}$ through $R^{29}$ are independently selected from (C1-C20)alkyl and (C6-C30)aryl;

Q represents a divalent organic bridge group for linking the two nitrogen atoms; and $Z^1$ through $Z^5$ are independently selected from a halide ion; $BF_4^-$; $ClO_4^-$; $NO_3^-$; $PF_6^-$; $HCO_3^-$; and a (C6-C30) aryloxy anion; (C1-C20)carboxylic acid anion; (C1-C20) alkoxy anion; (C1-C20)alkylcarbonate anion; (C1-C20) alkylsulfonate anion; (C1-C20)alkylamide anion; (C1-C20) alkylcarbamate anion or anion of Meisenheimer salt with or without at least one of halogen, nitrogen, oxygen, silicon, sulfur and phosphorus atoms, wherein a part of $Z^1$ through $Z^4$ coordinated at the cobalt atom may be de-coordinated.

Particularly, in Chemical Formula 12, Q represents (C6-C30)arylene, (C1-C20)alkylene, (C2-C20)alkenylene, (C2-C20)alkynylene, (C3-C20)cycloalkylene or fused (C3-C20) cycloalkylene, wherein the arylene, alkylene, alkenylene, alkynylene, cycloalkylene or fused cycloalkylene may be further substituted by a substituent selected from halogen atoms, (C1-C7)alkyl, (C6-C30)aryl and nitro groups, or may further include at least one hetero atom selected from O, S and N. Preferably, Q represents ethylene, trans-1,2-cyclohexylene or 1,2-phenylene, and more preferably trans-1,2-cyclohexylene.

Particularly, in Chemical Formula 12, p and q independently represent an integer from 1 to 5, preferably 2; $R^{26}$ represents primary or secondary (C1-C7)alkyl; $R^{27}$ through $R^{29}$ independently represent (C1-C7)alkyl, preferably $R^{26}$ and $R^{27}$ independently represent methyl, and $R^{28}$ and $R^{29}$ independently represent butyl; and $Z^1$ through $Z^5$ are independently selected from 2,4-dinitrophenolate and $BF_4^-$.

In another aspect, the present invention provides a method for preparing polycarbonate, including: carrying out copolymerization of carbon dioxide and an epoxide compound selected from the group consisting of C2-C20 alkylene oxide substituted or unsubstituted by halogen or alkoxy; C4-C20 cycloalkene oxide substituted or unsubstituted by halogen or alkoxy; and C8-C20 styrene oxide substituted or unsubstituted by halogen, alkoxy or alkyl, in the presence of a complex selected from the complexes represented by Chemical Formulas 1, 5, 6, 7, 8, 9, 10 and 11 and the complexes containing ligands selected from Chemical Formulas 2a, 2b, 2c, 3 and 4, as a catalyst.

Cobalt (III) complexes obtained from Salen-type ligands containing four quaternary ammonium salts may have different structures depending on the structures of the ligands. Such a different coordination structure is distinguished from a general structure coordinated with the four ligands in that it is not coordinated with imine. Instead of imine, the counter anion of the quaternary ammonium salt is coordinated. This has been demonstrated herein through $^1H$, $^{13}C$, $^{15}N$ NMR spectrometry, IR spectrometry, DFT calculation, and cyclic voltammetry (CV). Such a different coordination structure is formed when the metal coordination portion of the Salen ligand is less sterically hindered as a whole, for example, when the substituent at 3-position of salicylaldehyde as a component of the Salen ligand is less sterically hindered (e.g. methyl), and when ethylene diamine as another component of the Salen ligand is not substituted, or when only one or two hydrogen atoms attached to the four carbon atoms are substituted (e.g. cyclohexane diamine). On the other hand, when the metal coordination portion of the Salen ligand is highly sterically hindered as a whole, for example, when a bulky substituent, such as tert-butyl, is attached to 3-position of salicylaldehyde, or when all of the hydrogen atoms attached to the four carbon atoms of ethylene diamine are substituted with methyl groups, a conventionally available imine-coordinated tetradentate compound is obtained.

The following Reaction Scheme illustrates different coordination systems depending on the structures of Salen ligands:

| R¹ | R² | *N | R |
|---|---|---|---|
| 7 | H | H | ¹⁵N | H |
| 5 | —(CH₂)₄— | | | H |
| 9 | —(CH₂)₄— | | | —[(CH₂)₄NBu₃]⁺[BF₄]⁻ |
| 10 | —(CH₂)₄— | | | Me |

| | R¹ | R² | R³ | R⁴ | *N | R | R' |
|---|---|---|---|---|---|---|---|
| 8 | H | H | H | H | ¹⁵N | H | ᵗBu |
| 6 | —(CH2)4— | | H | H | | H | ᵗBu |
| 11 | Me | Me | Me | Me | | Me | Me |

X = 2,4-dinitrophenolate

The compounds (5, 7 and 10) with a different coordination system having no coordination with imine unexpectedly show high activity in copolymerizing carbon dioxide/epoxide. On the contrary, the conventional imine-coordinated tetradentate compounds (6, 8 and 11) have no activity or show low activity. It has been demonstrated through NMR and CV studies that the conventional imine-coordinated tetradentate compounds are more easily reduced into cobalt (II) compounds, as compared to the compounds with a different coordination system having no coordination with imine. Such cobalt (II) compounds having no activity in carbon dioxide/epoxide copolymerization.

In the compounds with a different coordination system having no coordination with imine, the anion coordination state is related with the temperature, solvent and ligand structure. Particularly, the anion coordination state has been demonstrated through NMR spectrometry in THF-$d_8$ similar to the polymerization medium. In the compounds [5, 7 and 10 wherein X=2,4-dinitrophenolate (also referred to as DNP)], two DNP ligands are always coordinated to cobalt and the remaining two DNP ligands continuously undergo conversion/reversion between the coordinated state and the non-coordinated state. In general, it is known that diamagnetic hexa-coordinated cobalt (III) compounds are not active in ligand substitution (Becker, C. A. L.; Motladiile, S. Synth. React. Inorg. Met.-Org. Chem. 2001, 31, 1545.). However, in the compounds with a different coordination system having no coordination with imine disclosed herein, cobalt is negatively charged so that negatively charged ligands may be de-coordinated. The de-coordinated negatively charged ligands are bound to the cation of the quaternary ammonium salt, and thus may not be released away from cobalt. Basically, non-coordinated anions are thermodynamically unstable species and tend to form coordination bonds back to cobalt. The combination of the above two types of tendencies contributes to the phenomenon in which two DNP ligands continuously undergo conversion/reversion between the coordinated state and the non-coordinated state. Several species of tetra-coordinated cobalt (III) compounds having negatively charged cobalt have been reported [(a) Collins, T. J.; Richmond, T. G.; Santarsiero, B. D.; Treco B. G. R. T. J. Am. Chem. Soc. 1986, 108, 2088. (b) Gray, H. B.; Billig, E. J. Am. Chem. Soc. 1963, 85, 2019.]. It has been also reported that addition of anionic or neutral ligands to such compounds causes easy conversion among the tetra-coordinated system, penta-coordinated system and hexa-coordinated system [(a) Langford, C. H.; Billig, E.; Shupack, S. I.; Gray, H. B. J. Am. Chem. Soc. 1964, 86, 2958; (b) Park, J.; Lang, K.; Abboud, K. A.; Hong, S. J. Am. Chem. Soc. 2008, 130, 16484.]. It may be stated that such unexpectedly high activity of the compounds with a different coordination system having no coordination with imine disclosed herein results from the fact that the two anionic ligands continuously undergo conversion/reversion between the coordinated state and the non-coordinated state. The following Reaction Scheme illustrates the mechanism of the growth of a polymer chain in carbon dioxide/epoxide copolymerization. In this mechanism, it is important that the carbonate anion formed at the end of the chain attacks the coordinated epoxide from the rear side. The above-mentioned continuous conversion/reversion between the coordinated state and the non-coordinated state allows a way of attacking the carbonate anion-coordinated epoxide from the rear side. In general, a nucleophilic attack occurs by an attack on a leaving group from the rear side. Thus, it is thought that difference in activities depends on how easily the anion, undergoing continuous conversion/reversion between the coordinated state and the non-coordinated state, can be de-coordinated from cobalt. According to NMR spectrometric analysis, binding affinities of the anions undergoing continuous conversion/reversion between the coordinated state and the non-coordinated state are in order of 5>10>7. Activities thereof are in reverse order.

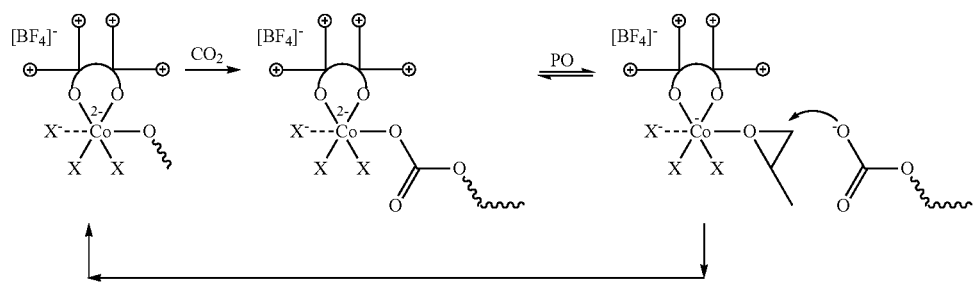

In the carbon dioxide/epoxide copolymerization reaction catalyzed with the compound with a different coordination system having no coordination with imine, the ratio of [water]/[catalyst] in the polymerization system plays an important role in realizing the catalytic activity. Even when water is removed by purifying epoxide and carbon dioxide thoroughly, the ratio of [water]/[catalyst] may be significantly high under such a polymerization condition that a relatively small amount of catalyst is added (i.e. under a ratio of [epoxide]/[catalyst] of 100,000 or 150,000). To obtain high activity (TON), it is required to realize the polymerization under a high [epoxide]/[catalyst] ratio, such as 100,000 or 150,000. Therefore, it is required for the catalyst to have low sensitivity to water so as to provide a commercially useful catalyst. In the case of a catalyst having a structure of 5, 7 or 10, induction time varies greatly depending on the degree of dewatering in the polymerization system. In other words, when the polymerization is carried out in the dry winter season, it is initiated after about 1-3 hours. However, when the polymerization is carried out in the wet and hot summer season, it is initiated sometimes after 12 hours. Once the polymerization is initiated, similar catalytic activities (TOF) are provided in the winter and summer seasons. In $^1$H NMR spectrometric study, it is observed that DNP contained in the compound attacks propylene oxide and the reaction rate rapidly decreases in the presence of a certain amount of water. It is estimated that such a decrease in the reaction rate results from the hydrogen bonding of water with the anion that undergoes continuous conversion/reversion between the coordinated state and the de-coordinated state, followed by degradation of the nucleophilic attacking capability.

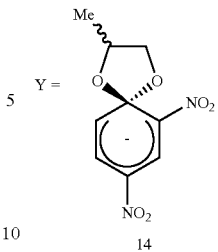

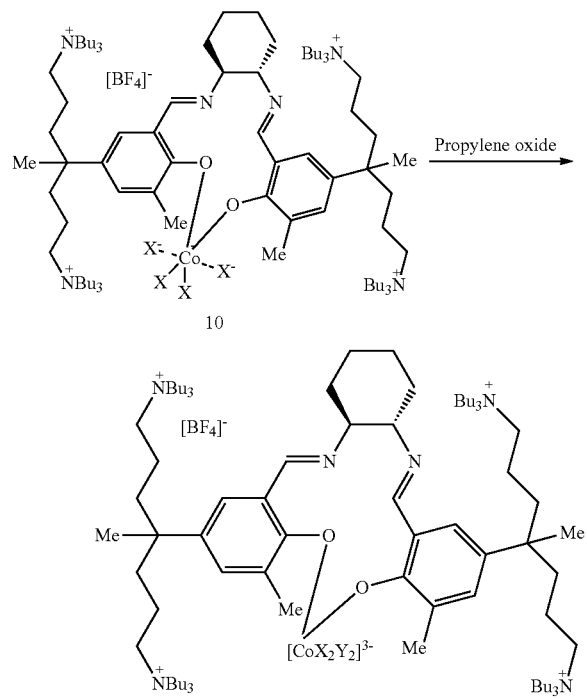

Such a great variation in the induction time depending on a degree of dewatering loads a difficulty on commercialization because of the requirement of optimization in the dewatering degree. When compound 14 in the above reaction scheme is used as a catalyst, the above problem is partially solved. Compound 14 may be obtained under a condition of very low [propylene oxide]/[catalyst] ratio (1,000 or lower). In this case, the amount of water remaining in propylene oxide is not significantly higher than the amount of catalyst. In other words, compound 14 is consistently obtained by controlling the [water]/[catalyst] ratio at a very low level. Compound 14 may be stored to be used as a catalyst. In the case of compound 14, the anion undergoing continuous conversion/reversion between the coordinated state and the de-coordinated state has already been reacted with propylene oxide. Thus, compound 14 has reduced sensitivity to water and the polymerization is realized under a consistent induction time (1-2 hours). In addition, compound 14 shows polymerization activity (TOF, 80,000 h$^{-1}$) in a short induction time (70 minutes) even under a high [epoxide]/[catalyst] ratio of 150,000, and thus provides a higher TON (20,000). In the case of compound 10, it is not capable of realizing polymerization activity under a [epoxide]/[catalyst] ratio of 150,000.

The compound with a different coordination system having no coordination with imine disclosed herein allows production of a compound (e.g. compound 14) having a structure in which the two DNP ligands are converted into the anions of the Meisenheimer salt by reacting with propylene oxide. In the case of the compound with a different coordination structure having no coordination with imine disclosed herein, two DNP ligands are strongly coordinated to cobalt and the remaining two DNP ligands undergo continuous conversion/reversion between the coordinated state and the de-coordinated state. Therefore, the latter two DNP ligands may be reacted rapidly with propylene oxide to provide compound 14 after 1 hour. On the other hand, in the case of an imine-coordinated tetradentate Salen-Co(III) compound (compound 6, 8 or 11), reaction with propylene oxide does not provide a compound (e.g. compound 14), in which only two DNP ligands are converted into the anions of Meisenheimer salt, but causes further conversion of the remaining DNP ligands into the anions of Meisenheimer salt. Especially, during the reaction with propylene oxide, reduction into a cobalt (II) compound may also significantly occur as mentioned above. As a result, it is not possible to obtain a compound (e.g. compound 14), in which two DNP ligands are maintained and the remaining two DNP ligands are converted into the anions of Meisenheimer salt. In addition, compound 14 may be prepared by the following anion substitution reaction. In the anion substitution reaction, it is a specific feature that one of the substituted anions of Meisenheimer salt is converted into DNP. When an imine-coordinated tetradentate Salen-Co (III) compound (e.g. compound 6, 8 or 11) is subjected to the same anion substitution reaction, cobalt reduction becomes a main reaction.

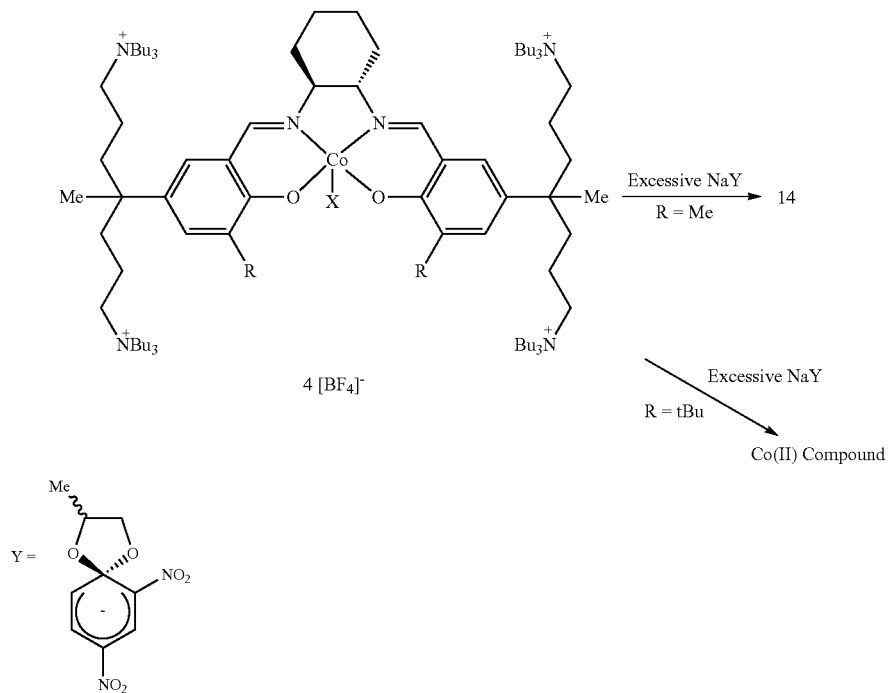

Particular examples of the epoxide compound that may be used herein include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxide-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxide norbornene, limonene oxide, dieldrin, 2,3-epoxidepropyl benzene, styrene oxide, phenylpropylene oxide, stilben oxide, chlorostilben oxide, dichlorostilben oxide, 1,2-epoxide-3-phenoxypropane, benzyloxymethyl oxirane, glycidylmethylphenyl ether, chlorophenyl-2,3-epoxidepropyl ether, ethoxypropyl methoxyphenyl ether, biphenyl glycidyl ether, glycidyl naphthyl ether, or the like. The epoxide compounds may be used alone or in combination of 2-4 kinds of compounds to perform copolymerization with carbon dioxide.

The epoxide compound may be used in the polymerization using an organic solvent as a reaction medium. Particular examples of the solvent that may be used herein include aliphatic hydrocarbons, such as pentane, octane, decane and cyclohexane, aromatic hydrocarbons, such as benzene, toluene and xylene, and halogenated hydrocarbons, such as chloromethane, methylene chloride, chloroform, carbon tetrachloride, 1,1-dichloroethane, 1,2-dichloroethane, ethyl chloride, trichloroethane, 1-chloropropane, 2-chloropropane, 1-chlorobutane, 2-chlorobutane, 1-chloro-2-methylpropane, chlorobenzene and bromobenzene. Such solvents may be used alone or in combination. More preferably, bulk polymerization using the monomer itself as a solvent may be performed.

The molar ratio of the epoxide compound to the catalyst, i.e., epoxide compound: catalyst molar ratio may be 1,000-1,000,000, preferably 50,000-200,000. Herein, the catalyst may realize a conversion ratio (i.e., moles of the epoxide compound consumed per mole of cobalt per hour) of 500 turnover/hr or higher. Carbon dioxide may be used at a pressure ranging from ambient pressure to 100 atm, preferably from 5 atm to 30 atm. The polymerization temperature may be 20° C.-120° C., suitably 50° C.-90° C.

To perform polymerization of polycarbonate, batch polymerization, semi-batch polymerization, or continuous polymerization may be used. When using a batch or semi-batch polymerization process, polymerization may be performed for 1-24 hours, preferably 1.5-4 hours. A continuous polymerization process may also be performed for an average catalyst retention time of 1.5-4 hours.

According to one embodiment of the present invention, it is possible to obtain polycarbonate having a number average molecular weight ($M_n$) of 5,000-1,000,000 and a polydispersity ($M_w/M_n$) of 1.05-4.0. Herein, $M_n$ means a number average molecular weight as measured by GPC with calibration using single-molecular weight distribution polystyrene standards. The polydispersity ($M_w/M_n$) means a ratio of a weight average molecular weight to a number average molecular weight as measured by GPC in the same manner as described above.

The resultant polycarbonate polymer includes at least 80% of carbonate bonds, sometimes at least 95% carbonate bonds. The carbonate material is easily degradable polymer leaving no residue and soot upon the combustion, and is useful as a packaging, heat insulating, coating material, etc.

The present invention provides a method for separately recovering a catalyst from a solution containing a copolymer and the catalyst, including:

contacting a solution containing the copolymer and the catalyst obtained from the above method with a solid inorganic material, polymer material or a mixture thereof non-soluble in the solution to form a complex of the solid inorganic material or polymer material and the catalyst and to separate the copolymer therefrom; and treating the complex of the solid inorganic material or polymer material and the catalyst with an acid or a metal salt of a non-reactive anion in a medium that is not capable of dissolving the solid inorganic material or polymer material to allow the catalyst to be dissolved into the medium and to separately recover the catalyst.

The expression "solution containing the copolymer and the catalyst" may be a solution obtained after the polymerization and still containing unreacted carbon dioxide and epoxide, a solution obtained after removing carbon dioxide only, or a solution obtained after removing both carbon dioxide and epoxide and further introducing another solvent thereto for the post-treatment. Preferred solvents that may be used for the post-treatment include methylene chloride, THF, etc.

To contact the solution containing the copolymer and the catalyst with the solid inorganic material, polymer material or a mixture thereof, the solid inorganic material, polymer material or a mixture thereof may be added to the solution containing the copolymer and the catalyst, followed by filtration, or the solution containing the copolymer and the catalyst may be passed through a column packed with the solid inorganic material, polymer material or a mixture thereof. The solid inorganic material may be surface-modified or non-modified silica or alumina. The solid polymer material may be a polymer material having a functional group capable of inducing deprotonation by alkoxy anion. More particularly, the functional group capable of inducing deprotonation by alkoxy anion may be a sulfonic acid, carboxylic acid, phenol or alcohol group.

The solid polymer material may have a number average molecular weight of 500-10,000,000 and is preferably crosslinked. However, non-crosslinked polymers may be used as long as they are not dissolved in the solution containing the copolymer and the catalyst. Particular examples of the "solid polymer material having a functional group capable of inducing deprotonation by alkoxy anion" include a homopolymer or copolymer containing a constitutional unit represented by any one of Chemical Formulas 13a to 13e in its polymer chain. Such a polymer material functioning as a support may be non-crosslinked as long as it is not dissolved in the above-mentioned solution. Preferably, the polymer material is suitably crosslinked to provide decreased solubility.

[Chemical Formula 13a]

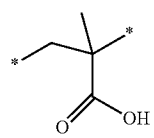

[Chemical Formula 13b]

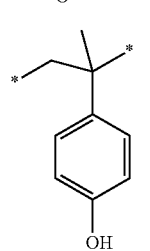

[Chemical Formula 13c]

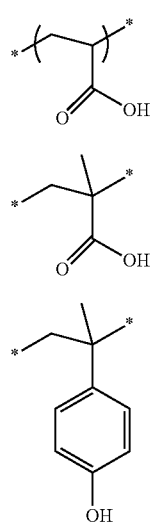

[Chemical Formula 13d]

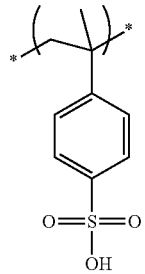

[Chemical Formula 13e]

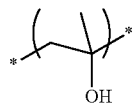

The present invention also provides a method for separately recovering a catalyst from a solution containing a copolymer and the catalyst, including:

contacting a solution containing the copolymer and the catalyst obtained from a carbon dioxide/epoxide copolymerization process using the above catalyst with silica to form a silica-catalyst complex and to separate the copolymer therefrom; and treating the silica-catalyst complex with an acid or a metal salt of a non-reactive anion in a medium that is not capable of dissolving silica to allow the catalyst to be dissolved into the medium and to separately recover the catalyst. The acid may be 2,4-dinitrophenol, and the metal salt of a non-reactive anion may be $MBF_4$ (wherein M represents Li, Na or K).

Reaction Scheme 1 shows a mechanism of separation and recovery of the catalyst. When polymerizing epoxide with carbon dioxide in the presence of the complex as a catalyst, the anion of the ammonium salt nucleophililically attacks the activated epoxide coordinated to the metal, thereby initiating the polymerization reaction. The alkoxy anion formed by the nucleophilic attack reacts with carbon dioxide to form a carbonate anion, which, in turn, attacks nucleophilically the epoxide coordinated to the metal to form a carbonate anion. As a result of the repetition of the above process, a polymer chain is formed. In this case, the anions of the ammonium salts contained in the catalyst are partially or totally converted into the carbonate anion or alkoxide anion containing the polymer chain. When removing carbon dioxide after the polymerization, the carbonate anions are converted into alkoxide anions. Then, the solution containing the catalyst and the copolymer is allowed to be in contact with the "polymer material having a functional group capable of inducing deprotonation by alkoxy anion" or a solid material (e.g. silica, alumina) having a surface hydroxyl group on the surface. As a result, the polymer chain receives protons through an acid-base reaction as shown in Reaction Scheme 1 so that it is maintained in the solution, while the catalyst forms a complex with the solid inorganic material or polymer material. Since the complex is insoluble in the solution, it may be easily separated from the solution via filtering.

[Reaction Scheme 1]
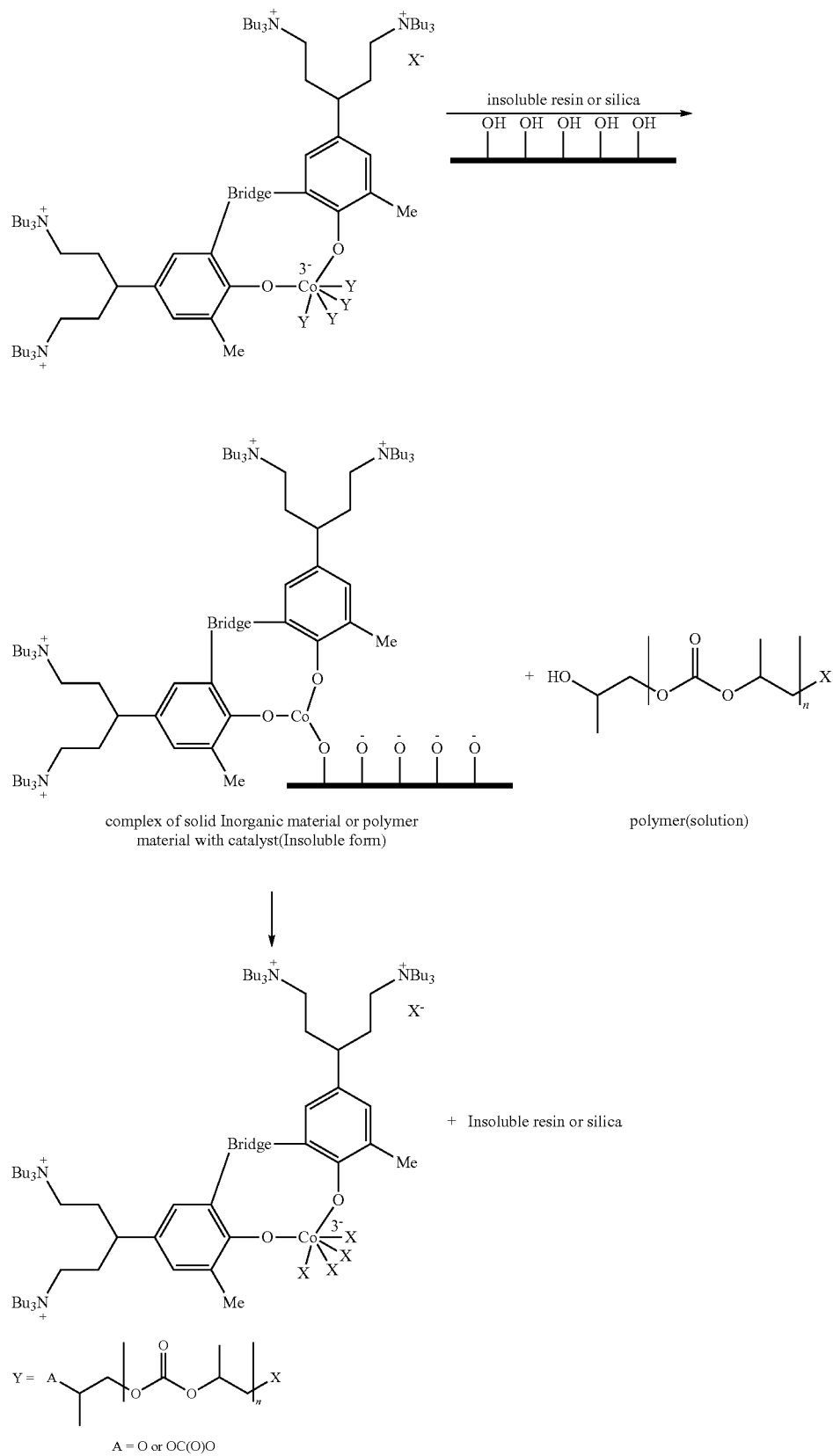

After the separation via filtering, the catalyst may be recovered and recycled from the complex of the solid inorganic material or polymer material with the catalyst. The complex of the solid inorganic material or polymer material with the catalyst is not dissolved in general solvents. However, when the recovered complex is treated with an acid or a metal salt of a non-reactive anion in a medium that is not capable of dissolving the inorganic material or polymer material, the catalyst may be dissolved into the medium via an acid-base reaction or salt metathesis. The resultant mixture may be filtered to allow the catalyst to be isolated from the solid inorganic material or polymer material, and then the catalyst may be separated and recovered. Herein, the acid used for the above treatment has a pKa value equal to or lower than the pKa value of the anion formed on the support. Preferably, the acid may be one whose conjugate base shows excellent activity in the polymerization in view of the reutilization. Particular examples of such acids include HCl and 2,4-dinitrophenol. Chloride anions and 2,4-dinitrophenolate anions are known to have high activity and high selectivity in the polymerization. Particular examples of the salt of a non-reactive anion include $DBF_4$ or $DClO_4$ (wherein D represents Li, Na or K). Upon the treatment with the salt of a non-reactive anion, a compound containing the non-reactive anion is dissolved out. The non-reactive anion may be replaced by the chloride anion and 2,4-dinitrophenolate anion having high activity and high selectivity via salt metathesis. Recovery of the catalyst may be carried out in a suitable solvent in which the catalyst is dissolved but the inorganic material or polymer material is not dissolved. Particular examples of such solvents include methylene chloride, ethanol or methanol.

It is possible to reduce the metal content of the resin to 15 ppm or lower by removing the catalyst through the above method after the polymerization. Therefore, the present invention also provides a copolymer separated from the solution containing the copolymer and the catalyst and having a metal content of 15 ppm or lower. If the catalyst is not removed from the resin in the above manner, the resin may still contain a metal compound that causes coloration. This is not favorable to commercialization. In addition, most transition metals are toxic. Thus, when the metal is not removed from the resin, the resin is significantly limited in its application. Further, when the polymer solution is not treated in the above manner so that the polymer chain has no proton at the end thereof, the polymer may be easily converted into single molecules via the so-called backbite reaction as shown in Reaction Scheme 2, under the condition of a slightly increased temperature or long-term storage. This may cause a severe problem when processing the resin and result in a significant degradation in the durability of the resin. Under these circumstances, the resin is not commercially acceptable. However, when treating the polymer solution in the above manner after the polymerizaiton, the polymer chain is provided with proton at the end thereof, and the alkoxide anion is converted into an alcohol group, which has weaker nucleophilic reactivity than alkoxide anion. Therefore, the backbite reaction of Reaction Scheme 2 does not occur so that the resin may provide good processability and durability.

[Reaction Scheme 2]

The complex disclosed herein may be prepared by providing an ammonium salt-containing ligand and coordinating the ligand to cobalt as shown in Reaction Scheme 3. A typical method for attaching the ligand to the metal include reacting cobalt acetate [Co(OAc)$_2$] with the ligand to de-coordinate the acetate ligand and to remove acetic acid, thereby providing a cobalt (II) compound, and then oxidizing the cobalt (II) compound with oxygen as an oxidizing agent in the presence of a suitable acid (HX, wherein X is the same as X in Chemical Formula 1) to obtain a cobalt (III) compound. The ammonium salt-containing ligand may be prepared according to the known method developed by the present inventors (*J. Am. Chem. Soc.* 2007, 129, 8082; *Angew. Chem. Int. Ed.*, 2008, 47, 7306-7309).

[Reaction Scheme 3]

-continued

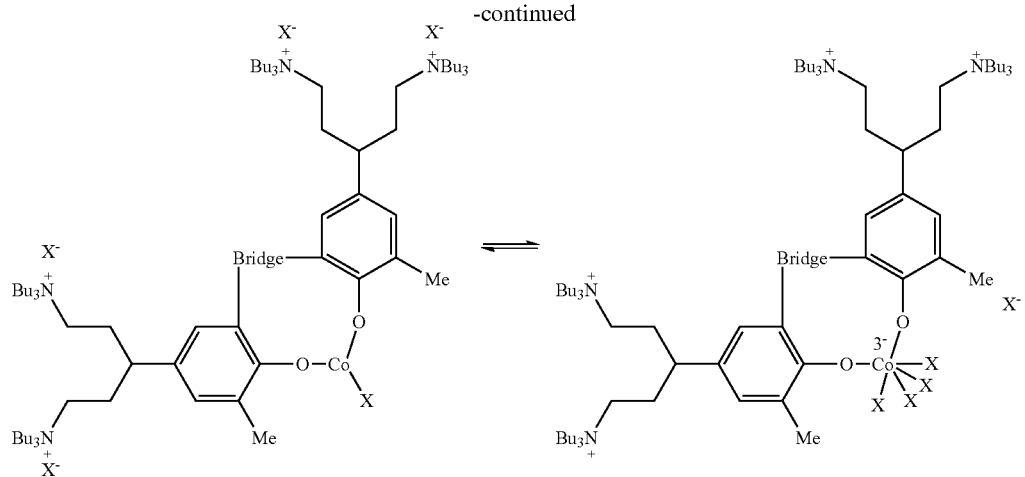

Advantageous Effects

The complex disclosed herein is prepared from a ligand containing a protonated group so that it takes a negative divalently or higher valently charged form. The complex may be used in carbon dioxide/epoxide copolymerization as a catalyst to realize high activity and high selectivity consistently. In addition, when carrying out carbon dioxide/epoxide copolymerization using the complex disclosed herein as a catalyst, the catalyst having protonated ligands is separated and recovered after the copolymerization so that it may be recycled. In this manner, it is possible to reduce the cost required for the catalyst and to realize high cost efficiency when preparing the copolymer. It is also possible to obtain a high-purity copolymer by removing the catalyst, i.e., metal compound from the copolymer. Therefore, it is possible to extend applications of the copolymer and to enhance the durability and processability of the copolymer.

DESCRIPTION OF DRAWINGS

The above and other objects, features and advantages of the present invention will become apparent from the following description of preferred embodiments given in conjunction with the accompanying drawings, in which.

BEST MODE

Figure 1:
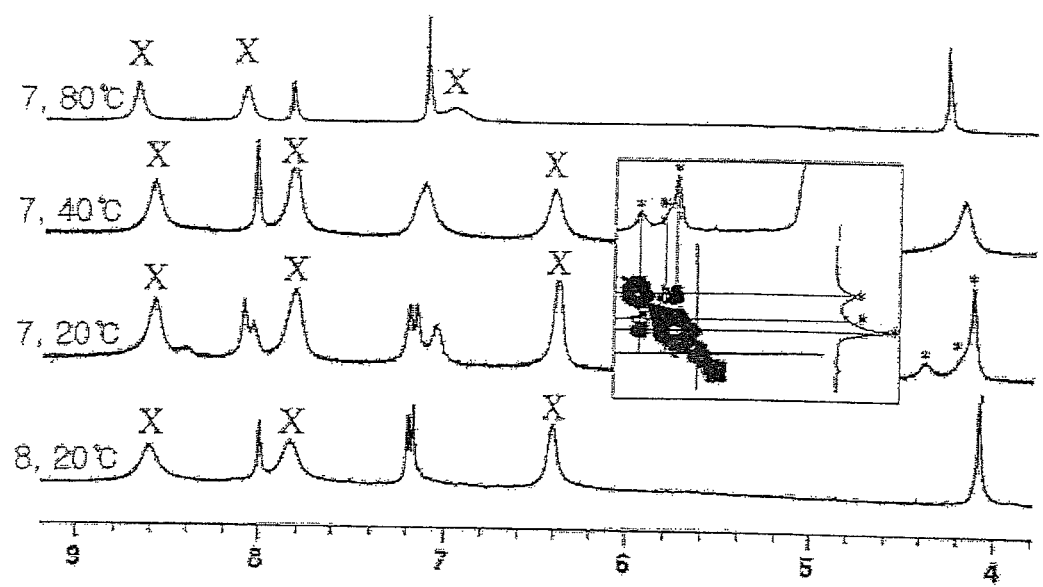
FIG. 1 shows $^1$H NMR spectra of compounds 7 and 8 in DMSO-$d_6$ as a solvent, wherein the signals labeled with X correspond to DNP signals and the 2D spectrum in the box is $^1$H-$^1$H COSY NMR spectrum of compound 7 at 20° T.

Hereinafter, the embodiments of the present invention will be described in detail with reference to examples. However, the following examples are for illustrative purposes only and not intended to limit the scope of this disclosure.

Example 1

Preparation of 3-methyl-5-[{BF$_4$$^-$Bu$_3$N$^+$(CH$_2$)$_3$}$_2$CH}]-salicylaldehyde compound The title compound is prepared by hydrolyzing the ligand represented by Chemical Formula 19a. The compound represented by Chemical Formula 19a is obtained by the known method developed by the present inventors (*Angew. Chem. Int. Ed.*, 2008, 47, 7306-7309).

[Chemical Formula 19a]

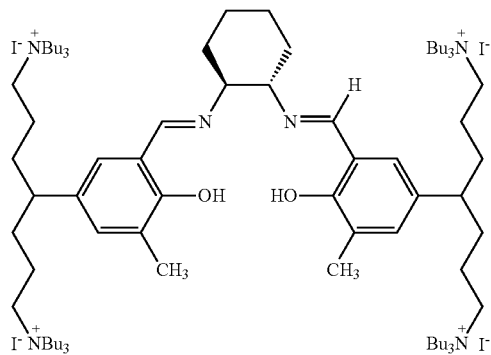

The compound represented by Chemical Formula 19a (0.500 g, 0.279 mmol) was dissolved in methylene chloride (4 mL), and then aqueous HI solution (2N, 2.5 mL) was added thereto and the resultant mixture was agitated for 3 hours at 70° C. The aqueous layer was removed, the methylene chloride layer was washed with water and dried with anhydrous magnesium chloride, and the solvents were removed under reduced pressure. The resultant product was purified by silica gel column chromatography eluting with methylene chloride/ethanol (10:1) to obtain 0.462 g of 3-methyl-5-[{I-Bu$_3$N+(CH$_2$)$_3$}$_2$CH}]-salicylaldehyde (yield 95%). The compound was dissolved in ethanol (6 mL), and AgBF$_4$ (0.225 g, 1.16 mmol) was added thereto, and the resultant mixture was stirred for 1.5 hours at room temperature, followed by filteration. The solvents were removed under reduced pressure and the resultant product was purified by silica gel column chromatography eluting with methylene chloride/ethanol (10:1) to obtain 0.410 g of 3-methyl-5-[{BF$_4$—Bu$_3$N+(CH$_2$)$_3$}$_2$CH}]-salicylaldehyde compound (yield 100%).

$^1$H NMR (CDCl$_3$): δ 11.19 (s, 1H, OH), 9.89 (s, 1H, CHO), 7.48 (s, 1H, m-H), 7.29 (s, 1H, m-H), 3.32-3.26 (m, 4H, —NCH$_2$), 3.10-3.06 (m, 12H, —NCH$_2$), 2.77 (septet, J=6.8 Hz, 1H, —CH—), 2.24 (s, 3H, —CH$_3$), 1.76-1.64 (m, 8H, —CH$_2$), 1.58-1.44 (m, 16H, —CH$_2$), 1.34-1.29 (m, 8H, —CH$_2$), 0.90 (t, J=7.6 Hz, 18H, CH$_3$) ppm. $^{13}$C {$^1$H} NMR (CDCl$_3$): δ 197.29, 158.40, 136.63, 133.48, 130.51, 127.12, 119.74, 58.23, 40.91, 32.51, 23.58, 19.48, 18.82, 15.10, 13.45 ppm.

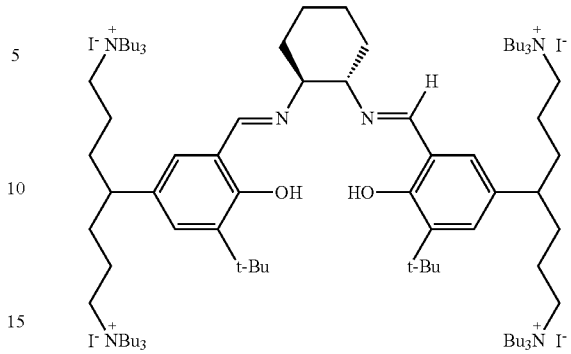

[Chemical Formula 19b]

$^1$H NMR (CDCl$_3$): δ 11.76 (s, 1H, OH), 9.92 (s, 1H, CHO), 7.53 (s, 1H, m-H), 7.35 (s, 1H, m-H), 3.36-3.22 (m, 16H, —NCH$_2$), 2.82 (br, 1H, —CH—), 1.78-1.70 (m, 4H, —CH$_2$), 1.66-1.46 (m, 16H, —CH$_2$), 1.42 (s, 9H, —C(CH$_3$)$_3$), 1.38-1.32 (m, 12H, butyl —CH$_2$), 0.93 (t, J=7.6 Hz, 18H, CH$_3$) ppm. $^{13}$C {$^1$H} NMR (CDCl$_3$): δ 197.76, 159.67, 138.70, 133.50, 132.63, 131.10, 120.40, 58.55, 41.45, 34.99, 32.28, 29.31, 23.72, 19.59, 19.00, 13.54 ppm.

Example 3

Preparation of Complex 7

Reaction Scheme 4 schematically illustrates one embodiment of the method for preparing the complex disclosed herein.

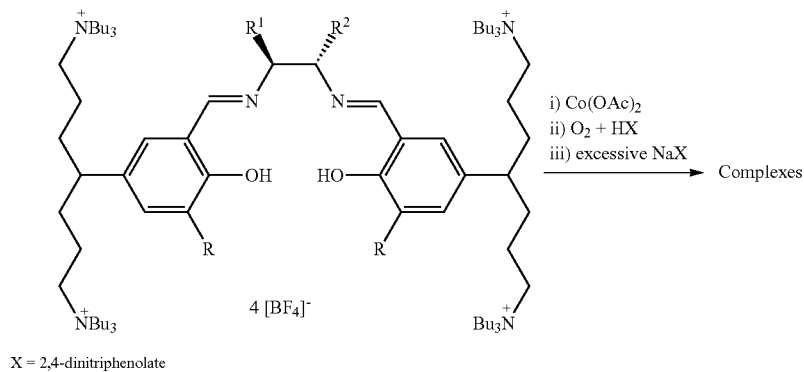

[Reaction Scheme 4]

X = 2,4-dinitriphenolate

Example 2

Preparation of 3-t-butyl-5-[{BF$_4^-$Bu$_3$N+(CH$_2$)$_3$}$_2$CH}]-salicylaldehyde compound The title compound is prepared from the compound represented by Chemical Formula 19b in the same manner as described in Example 1. The compound represented by Chemical Formula 19a is also obtained by the known method developed by the present inventors (*Angew. Chem. Int. Ed.*, 2008, 47, 7306-7309).

Ethylene diamine dihydrochloride (10 mg, 0.074 mmol), sodium t-butoxide (14 mg) and 3-methyl-5-[{BF$_4^-$Bu$_3$N+(CH$_2$)$_3$}$_2$CH}]-salicylaldehyde compound (115 mg) obtained from Example 1 are weighed with vials in a dry box, and ethanol (2 mL) was added thereto, followed by stirring at room temperature for overnight. The reaction mixture was filtered and solvent were removed under reduced pressure. The resultant product was redissolved into methylene chloride and filtered once again. The solvents were removed under reduced pressure, and Co(OAc)$_2$ (13 mg, 0.074 mmol) and ethanol (2 mL) are added thereto. The reaction mixture was stirred for 3 hours at room temperature and then the solvents were removed under reduced pressure. The resultant compound was washed with diethyl ether (2 mL) twice to obtain a solid compound. The solid compound was dissolved into methylene chloride (2 mL) and 2,4-dinitrophenol (14 mg, 0.074 mmol) was added thereto, and the resultant mixture was stirred for 3 hours in the presence of oxygen. Then, sodium 2,4-dinitrophenolate (92 mg, 0.44 mmol) was added to the reaction mixture and the stirring continued for overnight at room temperature. The reaction mixture was filtered over a pad of Celite and the solvents were removed to obtain the product as a dark brown solid compound (149 mg, yield 100%).

$^1$H NMR (DMSO-$d_6$, 40° C.): δ 8.84 (br, 2H, $(NO_2)_2C_6H_3O$), 8.09 (br, 2H, $(NO_2)_2C_6H_3O$), 8.04 (s, 1H, CH=N), 7.12 (s, 2H, m-H), 6.66 (br, 2H, $(NO_2)_2C_6H_3O$), 4.21 (br, 2H, ethylene-$CH_2$), 3.35-2.90 (br, 16H, $NCH_2$), 2.62 (s, 3H, $CH_3$), 1.91 (s, 1H, CH), 1.68-1.42 (br, 20H, $CH_2$), 1.19 (br, 12H, $CH_2$), 0.83 (br, 18H, $OH_3$) ppm. $^1$H NMR (THF-$d_8$, 20° C.): δ 8.59 (br, 1H, $(NO_2)_2C_6H_3O$), 8.10 (br, 1H, $(NO_2)_2C_6H_3O$), 7.93 (s, 1H, CH=N), 7.88 (br, 1H, $(NO_2)_2C_6H_3O$), 7.05 (s, 1H, m-H), 6.90 (s, 1H, m-H), 4.51 (s, 2H, ethylene-$CH_2$), 3.20-2.90 (br, 16H, $NCH_2$), 2.69 (s, 3H, $CH_3$), 1.73 (s, 1H, CH), 1.68-1.38 (br, 20H, $CH_2$), 1.21 (m, 12H, $CH_2$), 0.84 (t, J=6.8 Hz, 18H, $CH_3$) ppm. $^1$H NMR ($CD_2Cl_2$, 20° C.): δ 8.43 (br, 1H, $(NO_2)_2C_6H_3O$), 8.15 (br, 1H, $(NO_2)_2C_6H_3O$), 7.92 (br, 1H, $(NO_2)_2C_6H_3O$), 7.79 (s, 1H, CH=N), 6.87 (s, 1H, m-H), 6.86 (s, 1H, m-H), 4.45 (s, 2H, ethylene-$CH_2$), 3.26 (br, 2H, $NCH_2$), 3.0-2.86 (br, 14H, $NCH_2$), 2.65 (s, 3H, $CH_3$), 2.49 (br, 1H, CH), 1.61-1.32 (br, 20H, $CH_2$), 1.31-1.18 (m, 12H, $CH_2$), 0.86 (t, J=6.8 Hz, 18H, $CH_3$) ppm. $^{13}$C{$^1$H} NMR (DMSO-$d_6$, 40° C.): δ 170.33, 165.12, 160.61, 132.12 (br), 129.70, 128.97, 127.68 (br), 124.51 (br), 116.18 (br), 56.46, 40.85, 31.76, 21.92, 18.04, 16.16, 12.22 ppm. $^{15}$N{$^1$H} NMR (DMSO-$d_6$, 20° C.): δ −156.32, −159.21 ppm. $^{15}$N{$^1$H} NMR (THF-$d_8$, 20° C.): δ −154.19 ppm. $^{19}$F{$^1$H} NMR (DMSO-$d_6$, 20° C.): δ −50.63, −50.69 ppm.

Example 4

Preparation of Complex 8

Complex 8 is prepared from 3-t-butyl-5-[{$BF_4^-Bu_3N^+(CH_2)_3$}$_2$CH}]-salicylaldehyde obtained from Example 2 in the same manner as described in Example 3.

$^1$H NMR (DMSO-$d_6$, 40° C.): δ 8.82 (br, 2H, $(NO_2)_2C_6H_3O$), 7.89 (br, 3H, $(NO_2)_2C_6H_3O$, CH=N), 7.21 (s, 1H, m-H), 7.19 (s, 1H, m-H), 6.46 (br, 4H, $(NO_2)_2C_6H_3O$), 4.12 (s, 2H, ethylene-$CH_2$), 3.25-2.96 (br, 16H, $NCH_2$), 1.90 (s, 1H, CH), 1.71 (s, 9H, $C(CH_3)_3$), 1.67-1.32 (br, 20H, $CH_2$), 1.32-1.15 (m, 12H, $CH_2$), 0.88 (t, J=7.2 Hz, 18H, $CH_3$) ppm. $^1$H NMR (THF-$d_8$ 20° C.): δ 7.78 (s, 1H, CH=N), 7.31 (s, 1H, m-H), 7.12 (s, 1H, m-H), 4.19 (br, 2H, ethylene-$CH_2$), 3.43-2.95 (br, 16H, $NCH_2$), 2.48 (br, 1H, CH), 1.81-1.52 (br, 20H, $CH_2$), 1.50 (s, 9H, $C(CH_3)_3$), 1.42-1.15 (br, 12H, $CH_2$), 0.89 (t, J=6.8 Hz, 18H, $CH_3$) ppm. $^1$H NMR ($CD_2Cl_2$, 20° C.): δ 7.47 (s, 1H, CH=N), 7.10 (s, 1H, m-H), 7.07 (s, 1H, m-H), 4.24 (s, 2H, ethylene-$CH_2$), 3.31 (br, 2H, $NCH_2$), 3.09-2.95 (br, 14H, $NCH_2$), 2.64 (br, 1H, CH), 1.68-1.50 (br, 20H, $CH_2$), 1.49 (s, 9H, $C(CH_3)_3$), 1.39-1.26 (m, 12H, $CH_2$), 0.93 (t, J=6.8 Hz, 18H, $CH_3$) ppm. $^{13}$C{$^1$H} NMR (DMSO-$d_6$, 40° C.): (166.57, 166.46, 161.55, 142.16, 129.99, 129.26, 128.39, 128.13, 127.63, 124.18, 118.34, 56.93, 41.64, 34.88, 32.27, 29.63, 22.37, 18.64, 18.51, 12.70 ppm. $^{15}$N{$^1$H} NMR (DMSO-$d_6$): −163.43 ppm. $^{15}$N{$^1$H} NMR (THF-$d_8$, 20° C.): δ −166.80 ppm. $^{19}$F{$^1$H} NMR (DMSO-$d_6$, 20° C.): δ −50.65, −50.70 ppm.

Example 5

Preparation of Complex 9

Complex 9 is prepared according to Reaction scheme 5.

[Reaction Scheme 5]

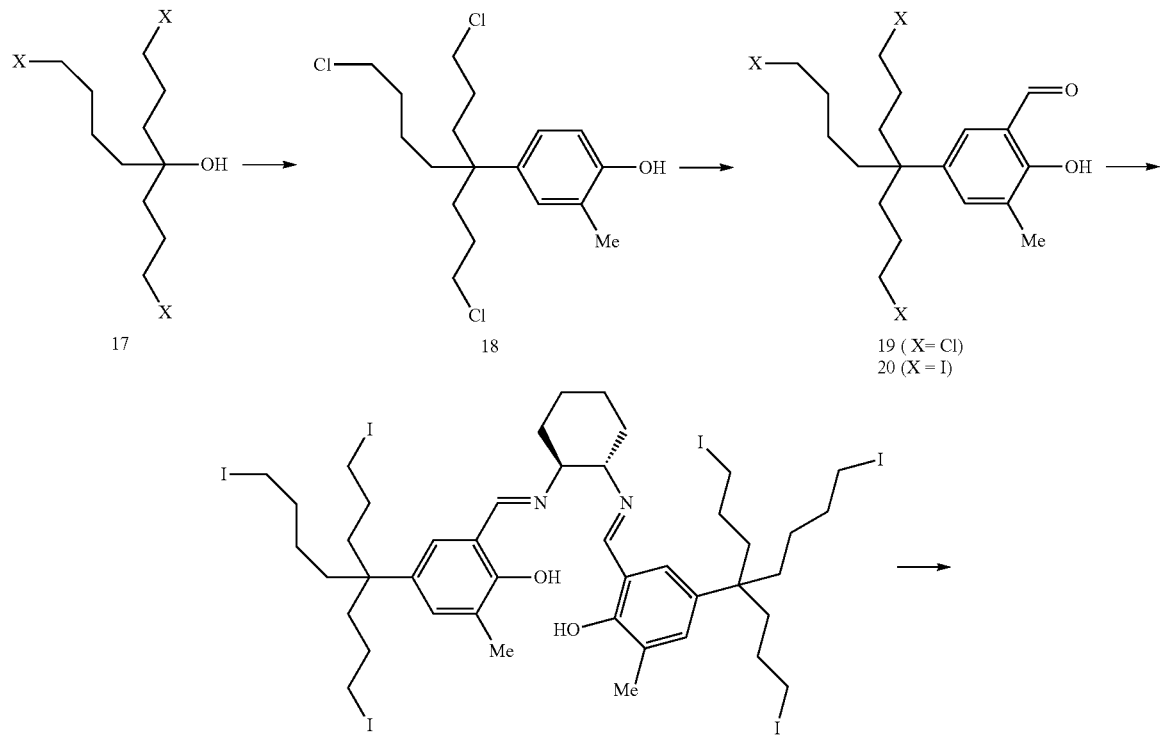

-continued

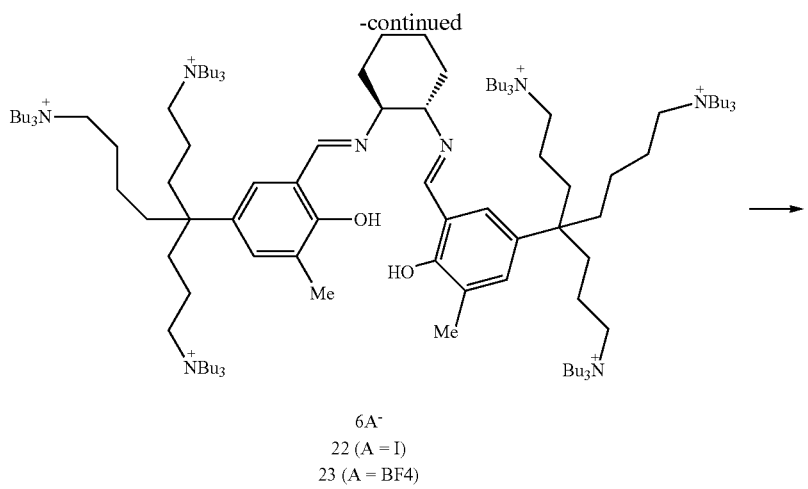

6A⁻
22 (A = I)
23 (A = BF4)

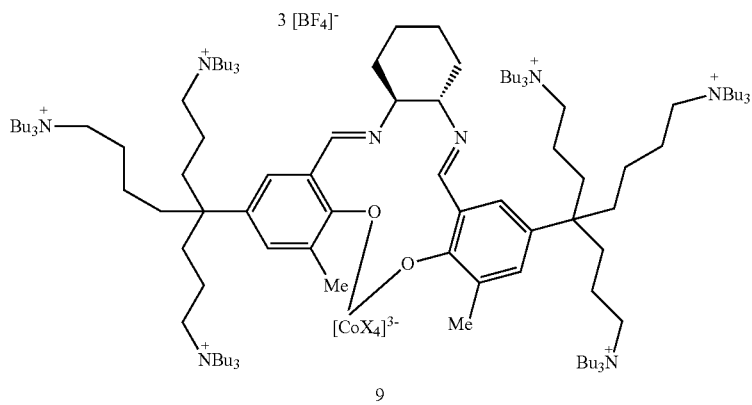

9

Preparation of Compound 17

First, 1-chloro-4-iodobutane (1.00 g, 4.57 mmol) was dissolved into a mixture solvent of diethyl ether/pentane (2:3) to obtain a concentration of 0.10 M, the resultant mixture was cooled to −78° C. t-butyl lithium (3.690 g, 9.610 mmol, 1.7M solution in pentane) was added gradually to the cooled solution of 1-chloro-4-iodobutane and stirred for 2 hours. 1,5-dichloropentane-3-one (838 mg, 4.580 mmol) dissolved in diethyl ether (8 mL) was added gradually to the reaction mixture. The reaction mixture was stirred for additional 4 hours at −78° C., and then ice water (50 mL) was added to quench the reaction path, followed by extraction with diethyl ether. The organic layer was collected and dried over anhydrous magnesium sulfate and filtered, the solvents were removed under reduced pressure. The obtained crude product was purified by column chromatography using silica gel (hexane:ethyl acetate=5:1) to obtain 820 mg of compound 17 (yield 65%).

$^1$H NMR (CDCl$_3$): δ 3.52 (t, J=6.4 Hz, 6H, CH$_2$Cl), 1.80-1.73 (m, 6H, CH$_2$), 1.56-1.52 (m, 4H, CH$_2$), 1.42 (s, 4H, CH$_2$) ppm. $^{13}$C{$^1$H} NMR (CDCl$_3$): δ 73.58, 45.69, 44.95, 38.29, 36.48, 32.94, 26.96, 20.88 ppm.

Preparation of Compound 18

Under nitrogen atmosphere, compound 17 (1.122 g, 4.070 mmol), o-cresol (3.521 g, 32.56 mmol), and aluminum trichloride (0.597 g, 4,477 mmol) were added to a round bottom flask and stirred for overnight. Diethyl ether (20 mL) and water (20 mL) were added thereto the reaction flask, and the aqueous phase was repeatedly extracted with diethyl ether (three times). The organic phases are combined and dried over anhydrous magnesium sulfate, filtered and removed the solvents under reduced pressure. The resultant oily product was purified by column chromatography using silica gel (hexane:ethyl acetate=10:1) to obtain 907 mg of compound 18 (yield 61%).

IR (KBr): 3535 (OH) cm$^{-1}$. $^1$H NMR (CDCl$_3$): δ 7.02 (d, J=2.0 Hz, 1H, m-H), 6.99 (dd, J=8.8 Hz, 2.0 Hz, 1H, m-H), 6.73 (d, J=8.0 Hz, 1H, o-H), 4.67 (s, 1H, OH), 3.53-3.46 (m, 6H, CH$_2$Cl), 2.27 (s, 3H, CH$_3$), 1.79-1.44 (m, 6H, CH$_2$), 1.67-1.62 (m, 2H, CH$_2$), 1.58-1.53 (m, 4H, CH$_2$), 1.28-1.20 (br, 2H, CH$_2$) ppm. $^{13}$C{$^1$H} NMR (CDCl$_3$): δ 151.81, 137.96, 128.89, 124.87, 114.70, 60.83, 46.05, 45.04, 42.09, 36.69, 35.07, 27.26, 21.40, 21.02, 16.54, 14.49 ppm. HRMS (FAB): m/z calcd (M$^+$C$_{18}$H$_{27}$Cl$_3$O) 364.1131. found 365.1206.

Preparation of Compound 19

Compound 18 (907 mg, 2.48 mmol), paraformaldehyde (298 mg, 9.920 mmol), magnesium dichloride (944 mg, 9.92 mmol) and triethylamine (1.051 g, 10.42 mmol) were introduced into a flask, and tetrahydrofuran (50 mL) was added as the solvent. The reaction mixture was refluxed for 5 hours under nitrogen atmosphere. The reaction mixture was cooled to room temperature, and methylene chloride (50 mL) and water (50 mL) were added thereto to extract the organic layer. The organic layer was collected and dried over anhydrous magnesium sulfate, filtered and removed the solvents. The resultant product was purified by column chromatography using silica gel (hexane:ethyl acetate=20:1) to obtain 540 mg of compound 19 (yield 58%).

IR (KBr): 2947 (OH), 1650 (C=O) cm$^{-1}$. $^1$H NMR (CDCl$_3$): δ 11.05 (s, 1H, OH), 9.78 (s, 1H, CH=O), 7.25 (s, 1H, m-H), 7.19 (s, 1H, m-H), 3.44-3.39 (m, 6H, CH$_2$Cl), 2.19 (s, 3H, CH$_3$), 1.74-1.43 (m, 12H, CH$_2$), 1.20-1.11 (br, 2H, CH$_2$) ppm. $^{13}$C{$^1$H} NMR (CDCl$_3$): δ 196.79, 158.07, 136.98, 135.85, 128.95, 126.85, 119.52, 45.77, 44.88, 42.12, 36.50, 34.64, 33.09, 27.07, 20.85, 15.71 ppm. HRMS (FAB): m/z calcd (M$^+$C$_{19}$H$_{27}$Cl$_3$O) 393.1151. found 393.1155.

Preparation of Compound 20

Compound 19 (520 mg, 1.304 mol) and sodium iodide (2.932 g, 19.56 mmol) were introduced into a flask, and acetonitrile (2 mL) was added as the solvent, followed by refluxing for 12 hours. Then, the solvent is removed under reduced pressure, methylene chloride (5 mL) and water (5 mL) are added thereto to extract the organic layer. The organic layer is dried over anhydrous magnesium sulfate and the solvent is removed under reduced pressure. The resultant product is purified through a column (hexane:ethyl acetate=20:1) to obtain 759 mg of compound 20 (yield 87%).

IR (KBr): 2936 (OH), 1648 (C=O) cm$^{-1}$. $^1$H NMR (CDCl$_3$): δ 11.06 (s, 1H, OH), 9.80 (s, 1H, CH=O), 7.25 (s, 1H, m-H), 7.17 (d, J=2.8 Hz, 1H, m-H), 3.21-3.14 (m, 6H, CH$_2$Cl), 2.27 (s, 3H, CH$_3$), 1.79-1.53 (m, 12H, CH$_2$), 1.28-1.19 (br, 2H, CH$_2$) ppm. $^{13}${$^1$H} NMR (CDCl$_3$): δ 196.81, 158.20, 137.00, 135.90, 128.90, 126.98, 119.54, 42.17, 38.45, 36.11, 33.93, 27.83, 24.50, 15.84, 7.96, 7.14 ppm.

Preparation of Compound 21

Compound 20 (680 mg, 1.018 mmol) and cyclohexyl diamine (58 mg, 0.509 mmol) were dissolved in methylene chloride (5 mL) and the reaction mixture was stirred for 12 hours. The resultant product was purified by passing through a short pad of silica eluting with methylene chloride to obtain the product as a pure yellow solid (560 mg, yield 78%).

IR (KBr): 2933 (OH), 1629 (C=N) cm$^{-1}$. $^1$H NMR (CDCl$_3$): δ 13.45 (s, 2H, OH), 8.34 (s, 2H, CH=N), 7.05 (s, 2H, m-H), 6.941 (d, J=1.6 Hz, 2H, m-H), 3.39-3.36 (m, 2H, cyclohexyl-CH), 3.17-3.09 (m, 12H, CH$_2$I), 2.26 (s, 6H, CH$_3$), 1.96-1.89 (m, 4H, cyclohexyl-CH$_2$), 0.96-1.43 (m, 32H, cyclohexyl-CH$_2$ and CH$_2$), 1.18-1.20 (br, 4H, CH$_2$) ppm. $^{13}$C{$^1$H} NMR (CDCl$_3$): δ164.97, 157.2, 135.58, 131.25, 127.12, 125.50, 117.65, 72.89, 42.00, 38.71, 36.14, 34.18, 33.73, 27.91, 24.57, 24.50, 16.32, 8.26, 7.18 ppm.

Preparation of Compound 22

Compound 21 (364 mg, 0.257 mmol) was dissolved in acetonitrile (5 mL), and added tributylamine (291 mg, 1.57 mmol). The reaction mixture was reflux for 2 days under nitrogen atmosphere. The reaction mixture was cooled to room temperature, the solvents were removed under reduced pressure, and diethyl ether (10 mL) was added. The resultant slurry was stirred for 10 minutes to obtain the product in solid form. Diethyl ether was decanted and the above process was repeated twice. The yellow solid was collected by filtration followed by washing with diethyl ether. The residual solvents were completely by applying vacuum to obtain 579 mg of compound 22 (yield 89%).

IR (KBr): 2959 (OH), 1627 (C=N) cm$^{-1}$. $^1$H NMR (CDCl$_3$): δ. 13.46 (s, 2H, OH), 8.58 (s, 2H, CH=N), 7.18 (s, 2H, m-H), 7.07 (s, 2H, m-H), 3.42 (br, 2H, cyclohexyl-CH), 3.32 (br, 16H, NCH$_2$), 3.16 (br, 32H, NCH$_2$), 2.10 (s, 6H, CH$_3$), 1.74-1.20 (br, 108H, cyclohexyl-CH$_2$, CH$_2$), 0.86 (t, 18H, CH$_3$), 0.75 (t, 36H, CH$_3$) ppm. $^{13}$C{$^1$H} NMR (CDCl$_3$): δ164.78, 157.27, 134.04, 130.82, 127.22, 125.15, 117.46, 71.01, 9.96, 59.63, 59.00, 58.86, 53.52, 43.03, 34.89, 33.90, 33.68, 24.16, 24.05, 23.07, 22.78, 20.69, 19.68, 19.53, 17.64, 15.79, 13.58 ppm.

Preparation of Compound 23

Compound 22 (455 mg, 0.180 mmol) and silver tetrafluoro borate (211 mg, 1.08 mmol) were introduced into a flask, and methylene chloride (12 mL) is added as a solvent. The flask was wrapped with aluminum foil and the reaction mixture was stirred at room temperature for 1 day. The reaction mixture was filtered over a pad of celite to remove solid, and the remaining solution was removed under reduced pressure. The product was purified by column chromatography using silica gel (methylene chloride:ethanol=5:1) to obtain 322 mg of yellow compound 23 (yield 78%).

IR (KBr): 2961 (OH), 1628 (C=N) cm$^{-1}$. $^1$H NMR (CDCl$_3$): δ. 13.64 (s, 2H, OH), 8.52 (s, 2H, CH=N), 7.27 (s, 2H, m-H), 7.16 (s, 2H, m-H), 3.44 (br, 2H, cyclohexyl-CH), 3.30-3.10 (br, 48H, NCH$_2$), 2.24 (s, 6H, CH$_3$), 1.95-1.29 (br, 108H, cyclohexyl-CH$_2$, CH$_2$), 0.99 (t, 18H, CH$_3$), 0.90 (t, 36H, CH$_3$) ppm.

Preparation of Complex 9

Compound 23 (59 mg, 0.026 mmol) and Co(OAc)$_2$ (4.6 mg, 0.026 mmol) were introduced into a vial in a glove box, ethanol (1 mL) was added and the reaction mixture was stirred for 12 hours. The solvent was removed under reduced pressure and the resultant product was washed twice with diethyl ether to obtain a red solid. 2,4-dinitrophenol (5.0 mg, 0.026 mmol) was added to and the reaction mixture and stirred for 3 hours in the presence of oxygen atmosphere. sodium 2,4-dinitrophenolate (27 mg, 0.13 mmol) was added to the reaction flask and stirred for further 12 hours. The resultant solution was filtered over a pad of celite, removed the solvents under reduced pressure to obtain 73 mg of a dark red solid.

IR (KBr): 2961 (OH), 1607 (C=N) cm$^{-1}$. $^1$H NMR (DMSO-d$_6$, 38° C.): δ 8.68 (br, 4H, (NO$_2$)$_2$C$_6$H$_3$O), δ. 8.05 (br, 4H, (NO$_2$)$_2$C6H$_3$O), 7.85 (br, 2H, CH=N), 7.30 (br, 4H, m-H), 6.76 (br, 4H, (NO$_2$)$_2$C$_6$H$_3$O), 3.58 (br, 2H, cyclohexyl-CH), 3.09 (br, 48H, NCH$_2$), 2.63 (s, 6H, CH$_3$), 1.53-1.06 (br, 108H, cyclohexyl-CH$_2$, CH$_2$), 0.93-0.85 (m, 54H, CH$_3$) ppm.

Example 6

Preparation of Complex 10

Complex 10 is prepared according to Reaction Scheme 6.

[Reaction Scheme 6]

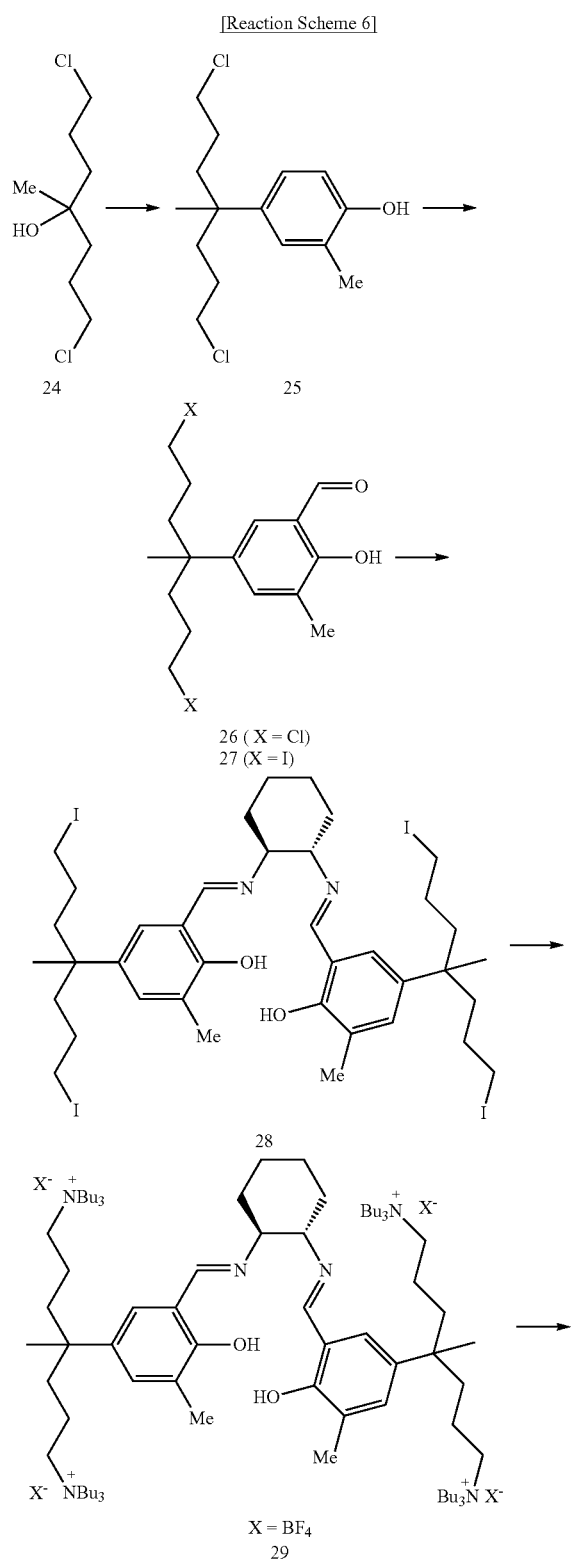

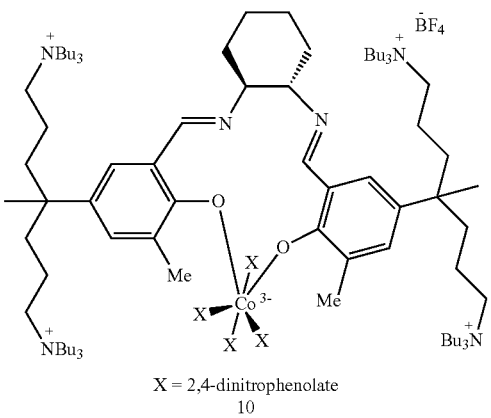

X = 2,4-dinitrophenolate
10

Preparation of Compound 24

First, 1,7-dichloroheptan-4-one (17.40 g, 95.04 mmol) was dissolved into diethyl ether (285 mL) under nitrogen atmosphere. The reaction mixture was cooled to −78° C., MeLi (1.5 M solution in diethyl ether 80.97 g, 142.56 mmol) was added drop wise using a syringe under nitrogen atmosphere. The reaction mixture was stirred for 2 hours at −78° C. water (170 mL) was added at −78° C. to quench the reaction. The product was extracted using diethyl ether. The aqueous layer was repeatedly extracted with diethyl ether (2 times). Collected the organic phases and dried over anhydrous magnesium sulfate, followed by filtration and the solvents were removed under reduced pressure to obtain 17.99 g of compound 24 (yield 95%). The resultant product may be used directly for the subsequent reaction without further purification.

$^1$H NMR (CDCl$_3$): δ. 3.59 (t, J=6.4 Hz, 4H, CH$_2$Cl), 1.90-1.86 (m, 4H, CH$_2$), 1.64-1.60 (m, 4H, CH$_2$), 1.23 (s, 3H, CH$_3$) ppm. $^{13}$C{$^1$H} NMR (CDC$_3$): δ. 72.32, 45.88, 39.51, 27.60, 27.23 ppm.

Preparation of Compound 25

Under nitrogen atmosphere, o-cresol (78.17 g, 722.82 mmol), compound 24 (17.99 g, 90.35 mmol) and AlCl$_3$ (13.25 g, 99.39 mmol) were mixed in a round bottom flask and stirred overnight. Diethyl ether (500 mL) and water (300 mL) were added to quench the reaction. The organic layer was collected and the aqueous layer was further extracted three times with diethyl ether (300 mL) and collected the organic layer. The organic layer was dried over anhydrous magnesium sulfate, followed by filtration, and then the solvent were removed by a rotary evaporator under reduced pressure. The excess o-cresol was removed by vacuum distillation (2 mm Hg) at 85° C. The obtained product can be used for subsequent reaction without further purification. In this manner, 25.40 g of compound 25 was obtained (yield 97%).

$^1$H NMR (CDCl$_3$): δ. 7.01 (d, J=2.0 Hz, 1H, m-H), 6.97 (dd, J=8.0 Hz, 2.0 Hz, 1H, m-H), 6.72 (d, J=8.0 Hz, 1H, o-H), 4.85 (s, 1H, OH), 3.45 (t, J=6.4 Hz, 4H, CH$_2$Cl), 2.27 (s, 3H, CH$_3$), 1.86-1.44 (m, 8H, CH$_2$), 1.30 (s, 3H, CH$_3$) ppm. $^{13}$C{$^1$H} NMR (CDCl$_3$): δ. 151.79, 138.67, 129.06, 125.02, 123.45, 114.85, 46.20, 41.12, 39.95, 28.09, 24.22, 16.58 ppm.

Preparation of Compound 26

Compound 25 (25.40 g, 87.83 mmol) was dissolved in tetrahydrofuran (650 mL) under nitrogen atmosphere. Paraformaldehyde (10.55 g, 351.32 mmol), magnesium chloride (33.52 g, 351.32 mmol) and triethylamine (37.31 g, 368.89 mmol) were introduced, into a flask under nitrogen atmosphere, and a refluxed for 5 hours under nitrogen atmosphere. The solvent was removed by a rotary evaporator under reduced pressure and methylene chloride (500 mL) and water (300 mL) were added. The resultant mixture was filtered over a pad of Celite to obtain a methylene chloride layer. The aqueous layer was further extracted three times with methylene chloride (300 mL) and combined organic layers, dried over anhydrous magnesium sulfate and filtered, the solvents were removed by a rotary evaporator under reduced pressure to obtain an oily compound. The remaining trace amount of triethylamine is removed by a vacuum pump. The resultant compound has high purity as determined by NMR analysis and can be used for the subsequent reaction without further purification. In this manner, 26.75 g of compound 26 was obtained (yield 96%).

$^1$H NMR (CDCl$_3$): δ. 11.14 (s, 1H, OH), 9.87 (s, 1H, CH=O), 7.33 (d, J=2.4 Hz, 1H, m-H), 7.26 (d, J=2.4 Hz, 1H, m-H), 3.47 (t, J=6.4 Hz, 4H, CH$_2$Cl), 2.30 (s, 3H, CH$_3$), 1.90-1.40 (m, 8H, CH$_2$), 1.35 (s, 3H, CH$_3$) ppm. $^{13}$C{$^1$H} NMR (CDCl$_3$): δ. 196.87, 158.22, 137.56, 136.11, 128.91, 119.69, 45.88, 40.67, 39.98, 27.96, 24.06, 15.81 ppm.

Preparation of Compound 27

Compound 26 (26.75 g, 84.32 mmol) was dissolved in acetonitrile (107 mL). Sodium iodide (126.39 g, 843.18 mmol) was added and the resulting mixture was refluxed for overnight. After cooling the reaction mixture to room temperature, water (300 mL) was added. The resultant solution was extracted three times with diethyl ether (300 mL) to collect the organic layer. The organic layer was dried over anhydrous magnesium sulfate, followed by filtration; the solvents were removed by a rotary evaporator under reduced pressure. The resultant product was purified through silica gel column chromatography eluting with hexane-toluene (5:1) as eluent to obtain the compound 27 (22.17 g, yield 83%).

$^1$H NMR (CDCl$_3$): δ. 11.14 (s, 1H, OH), 9.87 (s, 1H, CH=O), 7.33 (d, J=2.4 Hz, 1H, m-H), 7.25 (d, J=2.4 Hz, 1H, m-H), 3.14-3.09 (m, 4H, CH$_2$I), 2.30 (s, 3H, CH$_3$), 1.87-1.43 (m, 8H, CH$_2$), 1.34 (s, 3H, CH$_3$) ppm. $^{13}$C{H} NMR (CDCl$_3$): δ. 196.85, 158.20, 137.50, 136.09, 128.85, 126.93, 119.62, 44.28, 39.95, 28.66, 24.16, 15.81, 7.99 ppm.

Preparation of Compound 28

Compound 27 (8.56 g, 17.01 mmol) was dissolved in methylene chloride (97 mL) under nitrogen atmosphere. (±)-trans-1,2-diaminocyclohexane (0.97 g, 8.50 mmol) was added and stirred for overnight. Solvents were removed under reduced pressure to obtain the pure compound (9.00 g, yield 98%).

$^1$H NMR (CDCl$_3$): δ. 13.48 (s, 1H, OH), 8.31 (s, 1H, CH=N), 7.04 (d, J=1.6 Hz, 1H, m-H), 6.91 (d, J=1.6 Hz, 1H, m-H), 3.38-3.35 (m, 1H, cyclohexyl-CH), 3.08-3.03 (m, 4H, CH$_2$I), 2.25 (s, 3H, CH$_3$), 1.96-1.89 (m, 2H, cyclohexyl-CH$_2$), 1.96-1.43 (m, 10H, cyclohexyl-CH$_2$ and CH$_2$), 1.26 (s, 3H, CH$_3$) ppm. $^{13}$C{$^1$H} NMR (CDCl$_3$): δ. 165.01, 157.31, 136.12, 131.35, 126.93, 125.54, 117.67, 72.94, 44.47, 39.79, 33.73, 28.72, 24.57, 24.32, 16.28, 8.38, 8.26 ppm.

Preparation of Compound 29

Compound 28 (0.855 g, 0.79 mmol) was dissolved in acetonitrile (8.5 mL) under nitrogen atmosphere, tributyl amine (1.17 g, 6.32 mmol) was added and the resulting solution was refluxed for 48 hours. Solvents were removed by a rotary evaporator under reduced pressure. Diethyl ether (20 mL) was added to the obtained slurry and titurated for 15 minutes to precipitate the product as solid. The ether layer was decanted and the above process was repeated twice to obtain beige solid compound. The solid compound was added gradually to solution of AgBF$_4$ (0.642 g, 3.30 mmol) in ethanol (40 mL) with stirring. The reaction mixture was agitated for 24 hours under light-shielded atmosphere, and the resultant AgI was removed by filteration over a pad of celite. The solvents were removed under vacuum. Then, the resultant compound was dissolved in methylene chloride (6 mL), and further filtered through a Celite pad to remove floating materials. The resultant product was purified by column chromatography using silica, eluting with methylene chloride-ethanol (5:1) as eluent to obtain the purified compound (1.23 g, yield 90%).

$^1$H NMR (CDCl$_3$): δ. 13.55 (s, 1H, OH), 8.42 (s, 1H, CH=N), 7.12 (s, 1H, m-H), 7.08 (s, 1H, m-H), 3.38 (br, 1H, cyclohexyl-CH), 3.06 (br, 16H, NCH$_2$), 2.20 (s, 3H, CH$_3$), 1.88-1.84 (br, 2H, cyclohexyl-CH$_2$), 1.68-1.26 (br, 36H), 0.87-0.86 (br, 18H, CH$_3$) ppm. $^{13}$C{$^1$H} NMR (CDCl$_3$): δ. 165.23, 157.79, 135.21, 131.17, 127.18, 125.76, 117.91, 72.05, 59.16, 58.63, 40.16, 38.10, 37.71, 26.45, 24.91, 23.90, 20.31, 19.80, 17.30, 16.01, 13.97, 13.80, 13.79 ppm.

Preparation of Complex 10

Compound 29 (100 mg, 0.06 mmol) and Co(OAc)$_2$ (10.7 mg, 0.06 mmol) were introduced into a flask and ethanol (3 mL) was added as the solvent. The reaction mixture was stirred at room temperature for 3 hours and removed the solvents under reduced pressure. The obtained product was triturated 2 times with diethyl ether to obtain the red solid compound. The residual solvents were removed completely by applying reduced pressure. Methylene chloride (3 mL) was added to dissolve the compound. Then, 2,4-dinitrophenol (11.1 mg, 0.06 mmol) was introduced and the reaction mixture was stirred for 3 hours under oxygen atmosphere. Under oxygen atmosphere, sodium-2,4-dinitrophenolate (74.5 mg, 0.30 mmol) was introduced and the mixture was stirred for overnight. The resultant solution was filtered over a pad of celite and the solvents were removed under reduced pressure to obtain the complex 10 (137 mg, yield 100%).

$^1$H NMR (DMSO-d$_6$, 38° C.): δ. 8.65 (br, 2H, (NO$_2$)$_2$C$_6$H$_3$O), δ. 7.88 (br, 3H, (NO$_2$)$_2$C$_6$H$_3$O, CH=N), 7.31 (br, 2H, m-H), 6.39 (br, 2H, (NO$_2$)$_2$C$_6$H$_3$O), 3.38 (br, 1H, cyclohexyl-CH), 3.08 (br, 16H, NCH$_2$), 2.64 (s, 3H, CH$_3$), 2.06-1.85 (br, 2H, cyclohexyl-CH$_2$), 1.50-1.15 (br, 36H), 0.86 (br, 18H, CH$_3$) ppm.

Example 7

Preparation of Complex 11

3-methyl-5-[{BF$_4$$^-$Bu$_3$N$^+$(CH$_2$)$_3$}$_2$CH$_3$C}]-salicylaldehyde compound (493 mg, 0.623 mmol) and 2,3-diamino-2,3-dimethylbutane (36 mg, 0.311 mmol) were introduced into a flask. Ethanol (4 mL) was added as the solvent, molecular sieves (180 mg) were introduced and the resultant mixture was subjected to reflux for 12 hours under nitrogen atmosphere. The mixture was filtered through a Celite pad to remove the molecular sieves and removed the solvents under reduced pressure to obtain the product as yellow solid. Co(OAc)$_2$ (55 mg, 0.31 mmol) was added to the flask and ethanol (10 mL) as the solvent. The resulting mixture was stirred for 5 hours at room temperature. Solvents were removed under reduced pressure, and the resulting compound was triturated twice with diethyl ether to obtain the red color compound. 2,4-dinitrophenol (57 mg, 0.311 mmol) was added and the mixture was dissolved in methylene chloride (10 mL) and stirred for 12 hours in the presence of oxygen. Sodium-2,4-dinitrophenolate (320 mg, 1.56 mmol) was added and the resulting reaction mixture was stirred for further 12 hours. The solution was filtered over a pad of celite and the solvents were removed under reduced pressure to obtain 736 mg of a dark red solid product.

$^1$H NMR (DMSO-d$_6$, 38° C.): δ 8.62 (br, 4H, (NO$_2$)$_2$O$_6$H$_3$O), 7.87 (br, 4H, (NO$_2$)$_2$C$_6$H$_3$O), 7.72 (br, 2H, CH=N), 7.50 (br, 2H, m-H), 7.35 (br, 2H, m-H), 6.47 (br, 4H, (NO$_2$)$_2$C$_6$H$_3$O), 3.11 (br, 32H, NCH$_2$), 2.70 (s, 6H, CH$_3$), 1.66-1.22 (br, 82H), 0.88 (br, 36H, CH$_3$) ppm. $^{13}$C{$^1$H} NMR (DMSO-d$_6$): δ 164.67, 159.42, 132.30, 129.71, 128.86 (br), 128.46 (br), 127.42 (br), 124.05 (br), 118.84, 73.92, 57.74, 57.19, 25.94, 23.33, 22.61, 21.05, 18.73, 16.68, 16.43, 12.93 ppm.

Example 8

Preparation of Complex 12

Salen ligand (500 mg, 0.301 mmol) obtained from 3-methyl-5-[{BF$_4$$^-$Bu$_3$N$^+$(CH$_2$)$_3$}$_2$CH}]-salicylaldehyde compound and Co(OAc)$_2$ (53 mg, 0.30 mmol) were introduced into a flask, and added ethanol (15 mL) as solvent, the resulting solution was stirred for 3 hours under nitrogen atmosphere. The solvent was removed under reduced pressure, and the resultant compound was triturated twice with diethyl ether to obtain red color compound. The compound was dissolved in methylene chloride (10 mL). Then, HBF$_4$ (49 mg, 0.30 mmol) was added to the resultant solution in the presence of oxygen, followed by stirring for additional 3 hours. After that, the solvents were removed under reduced pressure to obtain 520 mg of a pure compound. Complex 12 was prepared according to the known method developed by the present inventors (*Angew. Chem. Int. Ed.*, 2008, 47, 7306-7309).

Example 9

Preparation of Complex 13

Complex 13 was obtained with a Salen ligand obtained from 3-t-butyl-5-[{BF$_4$$^-$Bu$_3$N$^+$(CH$_2$)$_3$}$_2$CH}]-salicylaldehyde compound in the same manner as described in Example 8.

$^1$H NMR (DMSO-d$_6$, 40° C.): δ 7.68 (s, 1H, CH=N), 7.36 (s, 1H, m-H), 7.23 (s, 1H, m-H), 3.61 (br, 1H, NCH), 3.31-2.91 (br, 16H, NCH$_2$), 2.04 (br, 1H, cyclohexyl-CH$_2$), 1.89 (br, 1H, cyclohexyl-CH$_2$), 1.74 (s, 9H, C(CH$_3$)$_3$), 1.68-1.35 (br, 20H, CH$_2$), 1.32-1.18 (br, 12H, CH$_2$), 0.91 (t, J=7.2 Hz, 18H, CH$_3$) ppm. $^{13}$C{$^1$H} NMR (DMSO-d$_6$): δ 161.66, 160.42, 140.90, 129.71, 128.38, 127.31, 117.38, 67.40, 55.85, 33.89, 31.11, 28.70, 27.70 (br), 22.58, 21.29, 19.47, 17.45, 15.21, 11.69 ppm.

Example 10

Preparation of Complex 14

Compound 10 was dissolved in propylene oxide, and the solution was allowed to stand for 1 hour and then removed the solvents under vacuum to obtain the complex 14.

$^1$H NMR (DMSO-d$_6$): δ 8.59 (s, 1H, (NO$_2$)$_2$C$_6$H$_3$O), 8.42 (s, 1H, spiro-Meisenheimer anion), 7.74 (s, 1H, (NO$_2$)$_2$C$_6$H$_3$O), 7.39-6.98 (m, 3H, m-H, CH=N), 6.81 (s, 1H, spiro-Meisenheimer anion), 6.29 (s, (NO$_2$)$_2$C$_6$H$_3$O), 5.35 (s, 1H, spiro-Meisenheimer anion), 4.43-4.29 (m, 1H, spiro-Meisenheimer anion), 4.21-3.99 (m, 2H, spiro-Meisenheimer anion), 3.21 (br, 1H, NCH), 3.09 (br, 16H, NCH$_2$), 2.93 (m, 3H, spiro-Meisenheimer anion), 2.62 (s, 3H, CH$_3$), 1.98 (br, 1H, cyclohexyl-CH$_2$), 1.62-1.39 (br, 20H, CH$_2$), 1.39-1.15 (br, 15H, CH$_2$, CH$_3$), 0.91 (br, 18H, CH$_3$) ppm.

Example 11

Preparation of Complex 35a

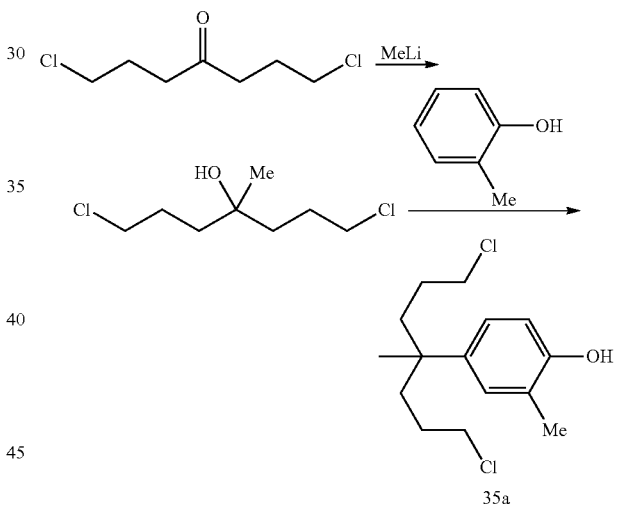

Preparation of 1,7-dichloro-4-methylheptan-4-ol

Under nitrogen atmosphere, 1,7-dichloro-4-methylheptan-4-one (17.40 g, 95.04 mmol) was dissolved in diethyl ether (285 mL). The reaction mixture was cooled to −78° C. and MeLi (1.5 M solution in diethyl ether, 80.97 g, 142.56 mmol) was added dropwise using a syringe under nitrogen atmosphere. The resulting mixture was stirred for 2 hours at −78° C. Water (170 mL) was added at −78° C. to quench the reaction path. The reaction mixture was extracted three times with diethyl ether (300 mL) and collected the organic phases. Combined the organic layers and dried over anhydrous magnesium sulfate, followed by filtration, and the solvents were removed by a rotary evaporator under reduced pressure to obtain 17.99 g (yield 95%) of the title compound, which may be used for the subsequent reaction without further purification.

$^1$H NMR (CDCl$_3$): δ. 3.59 (t, J=6.4 Hz, 4H, CH$_2$Cl), 1.90-1.86 (m, 4H, CH$_2$), 1.64-1.60 (m, 4H, CH$_2$), 1.23 (s, 3H, CH$_3$) ppm. $^{13}$C{$^1$H} NMR (CDCl$_3$): δ. 72.32, 45.88, 39.51, 27.60, 27.23.

Preparation of Complex 35a

Under nitrogen atmosphere, o-cresol (78.17 g, 722.82 mmol), 1,7-dichloro-4-methylheptane-4-ol (17.99 g, 90.35 mmol) and AlCl$_3$ (13.25 g, 99.39 mmol) were mixed in a round bottom flask and stirred overnight. Next, diethyl ether (500 mL) and water (300 mL) are introduced thereto to quench the reaction. The organic layers were collected, and the aqueous layer was further extracted three times with diethyl ether (300 mL). Combined the organic phases and dried over anhydrous magnesium sulfate, followed by filtration, and the solvents were removed by a rotary evaporator under reduced pressure. The excess o-cresol was removed by vacuum distillation (2 mmHg) at an oil bath temperature of 85° C. The compound remaining in the flask has a purity sufficient to be used for the subsequent reaction without further purification. In this manner, 25.40 g of complex 35a is obtained (yield 97%).

$^1$H NMR (CDCl$_3$): δ. 7.01 (d, J=2.0 Hz, 1H, m-H), 6.97 (dd, J=8.0 Hz, 2.0 Hz, 1H, m-H), 6.72 (d, J=8.0 Hz, 1H, o-H), 4.85 (s, 1H, OH), 3.45 (t, J=6.4 Hz, 4H, CH$_2$Cl), 2.27 (s, 3H, CH$_3$), 1.86-1.44 (m, 8H, CH$_2$), 1.30 (s, 3H, CH$_3$) ppm. $^{13}$C{$^1$H}NMR (CDCl$_3$): δ. 151.79, 138.67, 129.06, 125.02, 123.45, 114.85, 46.20, 41.12, 39.95, 28.09, 24.22, 16.58

Example 12

Preparation of Complex 39a

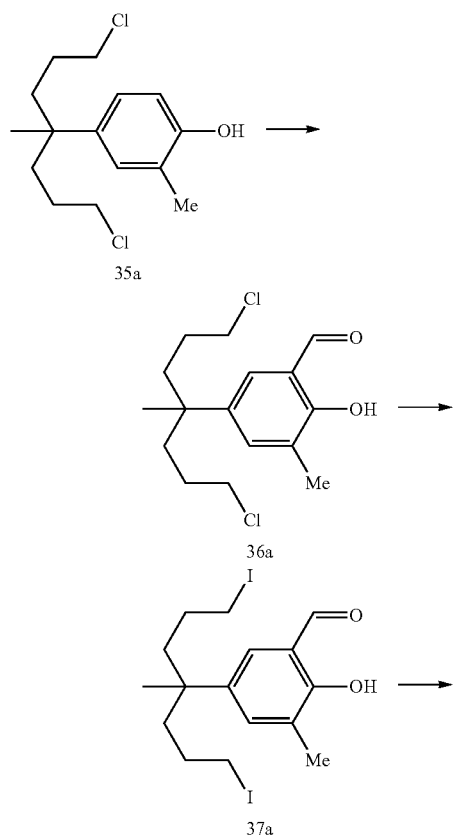

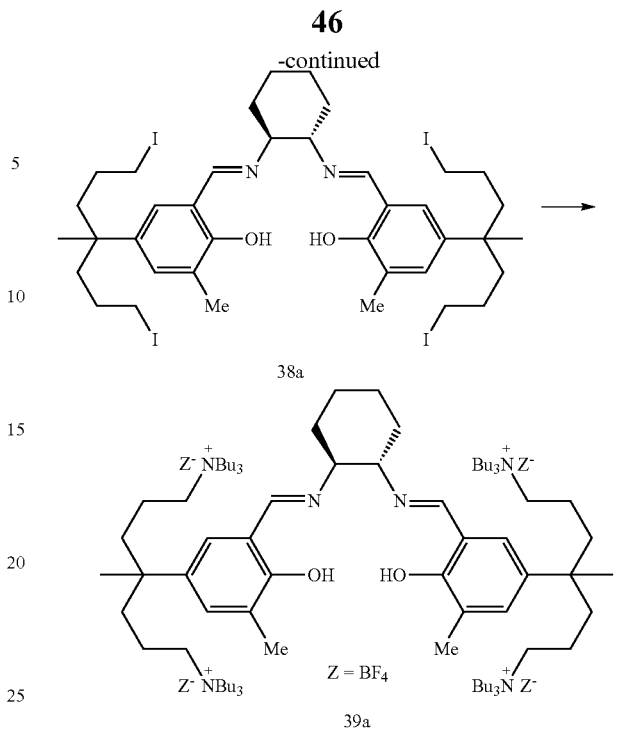

Preparation of Complex 36a

Complex 35a (25.40 g, 87.83 mmol) was dissolved in tetrahydrofuran (650 mL) under nitrogen atmosphere. Paraformaldehyde (10.55 g, 351.32 mmol), magnesium chloride (33.52 g, 351.32 mmol) and triethylamine (37.31 g, 368.89 mmol) were introduced, into a flask under nitrogen atmosphere, and a refluxed for 5 hours under nitrogen atmosphere. The solvent was removed by a rotary evaporator under reduced pressure and methylene chloride (500 mL) and water (300 mL) were added. The resultant mixture was filtered over a pad of Celite to obtain a methylene chloride layer. The aqueous layer was further extracted three times with methylene chloride (300 mL) and combined organic layers, dried over anhydrous magnesium sulfate and filtered, the solvents were removed by a rotary evaporator under reduced pressure to obtain an oily compound. The remaining trace amount of triethylamine is removed by a vacuum pump. The resultant compound has high purity as determined by NMR analysis and can be used for the subsequent reaction without further purification. In this manner 26.75 g of complex 36a was obtained (yield 96%).

$^1$H NMR (CDCl$_3$): δ. 11.14 (s, 1H, OH), 9.87 (s, 1H, CH=O), 7.33 (d, J=2.4 Hz, 1H, m-H), 7.26 (d, J=2.4 Hz, 1H, m-H), 3.47 (t, J=6.4 Hz, 4H, CH$_2$Cl), 2.30 (s, 3H, CH$_3$), 1.90-1.40 (m, 8H, CH$_2$), 1.35 (s, 3H, CH$_3$) ppm. $^{13}$C{$^1$H} NMR (CDC$_3$): δ. 196.87, 158.22, 137.56, 136.11, 128.91, 119.69, 45.88, 40.67, 39.98, 27.96, 24.06, 15.81.

Preparation of Complex 37a

Complex 36a (26.75 g, 84.32 mmol) was dissolved in acetonitrile (107 mL). Sodium iodide (126.39 g, 843.18 mmol) was added to the solution and the resulting solution was refluxed for overnight. After cooling the mixture to room temperature, water (300 mL) was added to quench the reaction path. The resultant solution was extracted three times with diethyl ether (300 mL) and collected the organic layers. The collected organic layer was dried over anhydrous magnesium sulfate, followed by filtration, and the solvents were removed by a rotary evaporator under reduced pressure. The resultant compound was purified by column chromatography using silica gel, eluting with hexane-toluene (5:1) as eluent to obtain pure complex 37a (22.17 g, yield 83%).

$^1$H NMR (CDCl$_3$): δ. 11.14 (s, 1H, OH), 9.87 (s, 1H, CH=O), 7.33 (d, J=2.4 Hz, 1H, m-H), 7.25 (d, J=2.4 Hz, 1H, m-H), 3.14-3.09 (m, 4H, CH$_2$I), 2.30 (s, 3H, CH$_3$), 1.87-1.43 (m, 8H, CH$_2$), 1.34 (s, 3H, CH$_3$) ppm. $^{13}$C{$^1$H} NMR (CDCl$_3$): δ. 196.85, 158.20, 137.50, 136.09, 128.85, 126.93, 119.62, 44.28, 39.95, 28.66, 24.16, 15.81, 7.99.

Preparation of Complex 38a

Complex 37a (8.56 g, 17.01 mmol) was dissolved in methylene chloride (97 mL) under nitrogen atmosphere. (±)-trans-1,2-diaminocyclohexane (0.97 g, 8.50 mmol) was added and stirred for overnight. The solvents were removed under reduced pressure to obtain pure complex 38a (9.00 g, yield 98%).

$^1$H NMR (CDCl$_3$): δ. 13.48 (s, 1H, OH), 8.31 (s, 1H, CH=N), 7.04 (d, J=1.6 Hz, 1H, m-H), 6.91 (d, J=1.6 Hz, 1H, m-H), 3.38-3.35 (m, 1H, cyclohexyl-CH), 3.08-3.03 (m, 4H, CH$_2$I), 2.25 (s, 3H, CH$_3$), 1.96-1.89 (m, 2H, cyclohexyl-CH$_2$), 1.96-1.43 (m, 10H, cyclohexyl-CH$_2$ and CH$_2$), 1.26 (s, 3H, CH$_3$) ppm. $^{13}$C{$^1$H} NMR (CDCl$_3$): δ. 165.01, 157.31, 136.12, 131.35, 126.93, 125.54, 117.67, 72.94, 44.47, 39.79, 33.73, 28.72, 24.57, 24.32, 16.28, 8.38, 8.26.

Preparation of Complex 39a

Complex 38a (0.855 g, 0.79 mmol) is dissolved into acetonitrile (8.5 mL) under nitrogen atmosphere, tributyl amine (1.17 g, 6.32 mmol) was added and the resulting solution was refluxed for 48 hours. Solvents were removed by a rotary evaporator under reduced pressure. Diethyl ether (20 mL) was added to the obtained slurry and titurated for 15 minutes to precipitate the product as solid. The ether layer was decanted and the above process was repeated twice to obtain beige solid compound. The solid compound was added gradually to solution of AgBF$_4$ (0.642 g, 3.30 mmol) in ethanol (40 mL) with stirring. The reaction mixture was agitated for 24 hours under light-shielded atmosphere, and the resultant AgI was removed by filtration over a pad of celite. The solvents were removed under vacuum. Then, the resultant compound was dissolved in methylene chloride (6 mL), and further filtered through a Celite pad to remove floating materials. The resultant product was purified by column chromatography using silica, eluting with methylene chloride-ethanol (5:1) as eluent to obtain the 39a (1.23 g, yield 90%).

$^1$H NMR (CDCl$_3$): δ. 13.55 (s, 1H, OH), 8.42 (s, 1H, CH=N), 7.12 (s, 1H, m-H), 7.08 (s, 1H, m-H), 3.38 (br, 1H, cyclohexyl-CH), 3.06 (br, 16H, NCH$_2$), 2.20 (s, 3H, CH$_3$), 1.88-1.84 (br, 2H, cyclohexyl-CH$_2$), 1.68-1.26 (br, 36H), 0.87-0.86 (br, 18H, CH$_3$) ppm. $^{13}$C{$^1$H} NMR (CDCl$_3$): δ. 165.23, 157.79, 135.21, 131.17, 127.18, 125.76, 117.91, 72.05, 59.16, 58.63, 40.16, 38.10, 37.71, 26.45, 24.91, 23.90, 20.31, 19.80, 17.30, 16.01, 13.97, 13.80, 13.79

Example 13

Preparation of Complex 40a

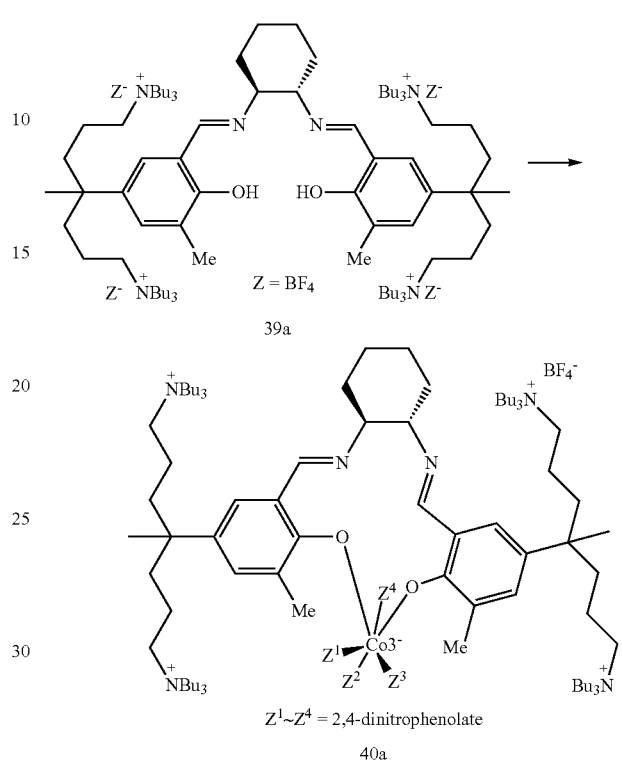

Preparation of Complex 40a

Complex 39a (100 mg, 0.06 mmol) and Co(OAc)$_2$ (10.7 mg, 0.06 mmol) were introduced into a flask and ethanol (3 mL) was added as the solvent. The reaction mixture was stirred at room temperature for 3 hours and removed the solvents under reduced pressure. The obtained product was triturated 2 times with diethyl ether to obtain the red solid compound. The residual solvents were removed completely by applying reduced pressure. Methylene chloride (3 mL) was added to dissolve the compound. Then, 2,4-dinitrophenol (11.1 mg, 0.06 mmol) was introduced and the reaction mixture was stirred for 3 hours under oxygen atmosphere. Under oxygen atmosphere, sodium-2,4-dinitrophenolate (74.5 mg, 0.30 mmol) was introduced and the mixture was stirred for overnight. The resultant solution was filtered over a pad of celite and the solvents were removed under reduced pressure to obtain the complex 40a (138 mg, yield 100%).

$^1$H NMR (DMSO-d$_6$, 38° C.): δ. 8.65 (br, 2H, (NO$_2$)$_2$C$_6$H$_3$O), δ. 7.88 (br, 3H, (NO$_2$)$_2$C$_6$H$_3$O, CH=N), 7.31 (br, 2H, m-H), 6.39 (br, 2H, (NO$_2$)$_2$C$_6$H$_3$O), 3.38 (br, 1H, cyclohexyl-CH), 3.08 (br, 16H, NCH$_2$), 2.64 (s, 3H, CH$_3$), 2.06-1.85 (br, 2H, cyclohexyl-CH$_2$), 1.50-1.15 (br, 36H), 0.86 (br, 18H, CH$_3$) ppm.

Example 14

Structural Analysis of Complexes

Complexes 7 and 8 obtained from Examples 3 and 4 are subjected to intensive structural analysis.

(1) $^1$H, $^{13}$C and $^{15}$N NMR spectra and IR spectrum

FIGS. 1, 2, 3, 4 and 5 show $^1$H NMR spectrum, $^{13}$C NMR spectrum and $^{15}$N NMR spectrum of compounds 7 and 8 in DMSO-d$_6$ as a solvent, and $^1$H NMR spectra of compounds 7 and 8 in THF-d$_8$ and CD$_2$Cl$_2$ as solvents. It can be seen that the two compounds show clearly different behaviors. In the case of complex 8 prepared from a ligand wherein R is t-butyl, sharp signals appear in both $^1$H NMR spectrum and $^{13}$C NMR spectrum. This is a typical behavior of tetradentate Salen-Co (III) compound. In the $^{15}$N NMR spectrum, only one signal appears at −163.43 ppm regardless of temperature.

In the $^1$H NMR spectrum and $^{13}$C NMR spectrum of complex 7 (Example 3) prepared from a ligand wherein R is methyl, a very complex and broad signal appears at room temperature, a simple and broad signal is obtained at 40° C., and a sharp signal is obtained at 80° C. The ratio of [DNP]/[Salen-unit] obtained from integration of the $^1$H NMR spectrum is near 4.0 rather than 5.0 observed in the case of complex 8. As determined by $^{15}$N NMR, two signals appear at −156.32 and −159.21 ppm under room temperature, a broad signal including two fused signals appears at 40° C., and only one sharp signal appears at 80° C.

Figure 4:
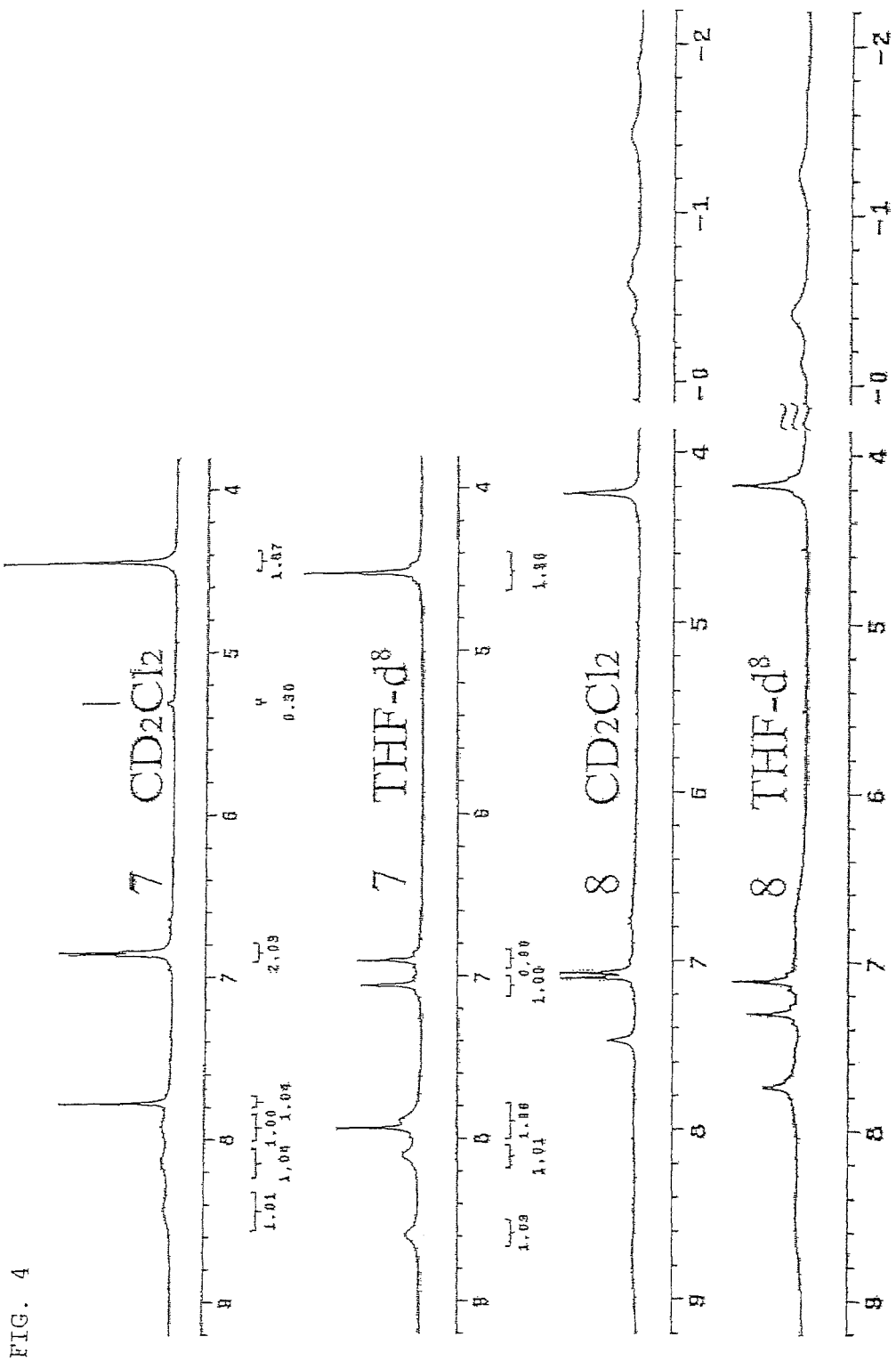
FIG. 4 shows $^1$H NMR spectra of compounds 7 and 8 in THF-$d_8$ and CD$_2$Cl$_2$ as a solvent.

Complexes 7 and 8 show significantly different behaviors as determined by $^1$H NMR spectrometry in THF-d$_8$ or CD$_2$Cl$_2$ (FIG. 4). In the $^1$H NMR spectrum of complex 8, a set of Salen-unit signals appears and a very broad DNP signal appears. Especially, some signals appear at an abnormal range, −2 to 0 ppm. This suggests that some paramagnetic compounds are present. In the case of $^1$H NMR spectrum of complex 7, only one set of Salen-unit signals appears, which has a significantly different chemical shift from complex 8. Broad DNP signals are observed at 7.88, 8.01 and 8.59 ppm. However, the ratio of [DNP]/[Salen-unit] integration is about 2.0, and only two DNP signals are observed among the four DNP signals observed in DMSO-d$_6$ with the remaining two non-observed. As determined in CD$_2$Cl$_2$, $^1$H NMR spectrometric behaviors of complexes 7 and 8 are similar to those in THF-d$_8$.

In the $^{15}$N NMR spectrum in THF-d$_8$, a sharp signal appears at −166.80 ppm (complex 8) or −154.32 ppm (complex 7). It is not reasonable to regard such a difference in chemical shift values of 12.5 ppm as a difference caused merely by the effect of substituents. It is reported that chemical shift values in the $^{15}$N NMR spectrum of imine compounds (—N═C—C$_4$H$_4$—X) and hydrazone compounds (N—N═C—C$_4$H$_4$—X) follow the Hammett type equation with a gradient of about 10. Considering a difference caused by the methyl and t-butyl substituents, the two substituents contribute a difference in chemical shift values of 1 ppm or less (Neuvonen, K.; Fülöp, F.; Neuvonen, H.; Koch, A.; Kleinpeter, E.; Pihlaja, K. *J. Org. Chem.* 2003, 68, 2151). In addition, in the case of dipyrrolmethene ligand and zinc (II) compounds obtained therefrom, substitution of hydrogen with ethyl provides a difference in chemical shift values of 2 ppm in $^{15}$N NMR spectrometry (Wood, T. E.; Berno, B.; Beshara, C. S.; Thompson, Alison, *J. Org. Chem.* 2006, 71, 2964). In fact, when viewed from the state of ligands used for preparing complexes 7 and 8, chemical shift difference is as low as 2.86 ppm. Therefore, it can be thought that the value of chemical shift of 12.5 ppm as observed herein results from different structures of the two complexes, i.e. complexes 7 and 8. When observing $^{15}$N NMR spectrum in THF-d$_8$ while varying temperature, complex 7 shows a relatively broadened signal as the temperature decreases, resulting in a full width at half maximum (FWHM) of 10 ppm at −75° C. On the other hand, complex 8 shows a relatively sharp signal at −75° C. as determined by a FWHM of 1.5 ppm. The above results suggest that complex 8 has a general structure of rigid Salen-Co (III) compounds to which all of the four ligands of Salen are coordinated, while complex 7 has a more flexible structure different therefrom.

Figure 5:
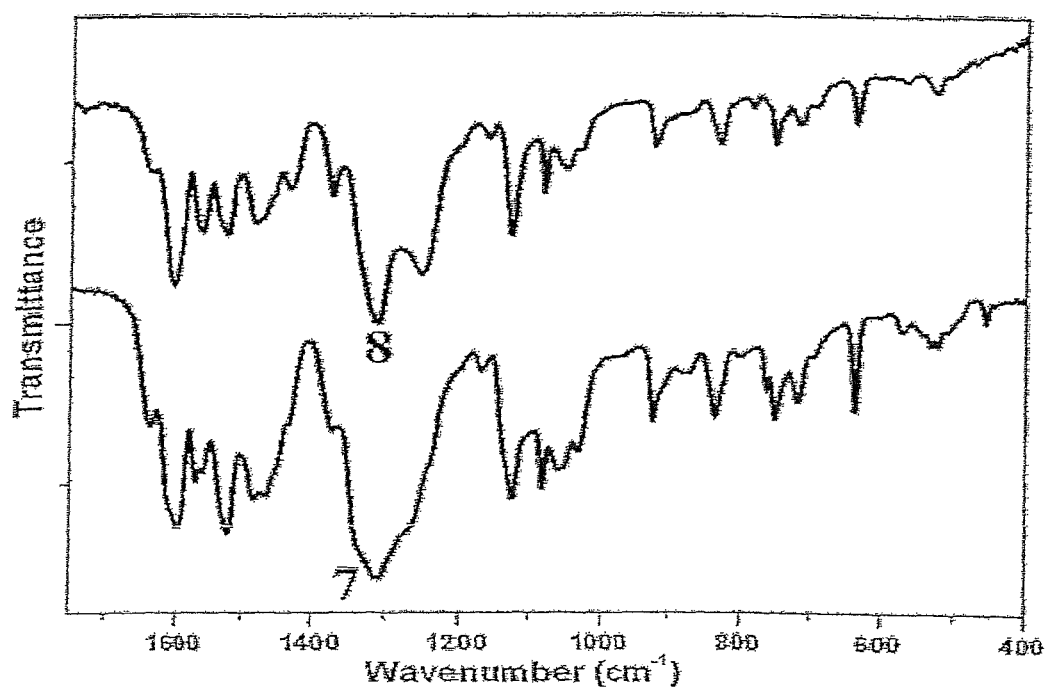
FIG. 5 shows IR spectra of compounds 7 and 8.

As shown in FIG. 5, the two complexes show clearly different signals in a range of 1200-1400 cm$^{-1}$ corresponding to the symmetric vibration of —NO$_2$ in IR spectra.

(2) Suggestion of Structure of Complexes

It can be said that complex 8 has a structure of a general Salen ligand-containing cobalt complex in which all of the four ligands of Salen are coordinated to cobalt, when observed by the $^1$H, $^{13}$C, and $^{15}$N NMR spectra. After carrying out ICP-AES, elemental analysis and $^{19}$F NMR spectrometry, it is found that one equivalent of NaBF$_4$ is inserted into the complex. In the $^1$H NMR spectrum, a broad DNP signal is observed, which suggests that the DNP ligand undergoes continuous conversion/reversion between the coordinated state and the de-coordinated state. As a part of the conversion/reversion, a square-pyramidal cobalt compound may be present transiently and the square-pyrimidal compound is known to be a paramagnetic compound [(a) Konig, E.; Kremer, S.; Schnakig, R.; Kanellakopulos, B. *Chem. Phys.* 1978, 34, 79. (b) Kemper, S.; Hrobàrik, P.; Kaupp, M.; Schlörer, N. E. *J. Am. Chem. Soc.* 2009, 131, 4172.]. Therefore, an abnormal signal is always observed at −2 to 0 ppm in the $^1$H NMR spectrum of complex 8.

When complex 7 has the above-mentioned non-imine coordinated structure, the analytic data may be understood. In addition, the structure is demonstrated through the following DFT calculation and electrochemical experiments. The structure is characterized in that four DNP ions, which are conjugate anions of quaternary ammonium salt, are coordinated instead of imine. The last operation of the catalyst preparation includes reaction with 5 equivalents of NaDNP suspended in CH$_2$Cl$_2$ to perform a change of [BF$_4$]$^-$ into DNP anion. [DNP]/[Salen-unit] integration ratio is 4.0 and this is not significantly changed even when using a more excessive amount of NaDNP (10 equivalents) or when increasing the reaction time. In other words, one among the four BF$_4$ remains unsubstituted. Since BF$_4$ signals are observed in $^{19}$F NMR but Na$^+$ ion is not observed from ICP-AES analysis unlike complex 8, it can be seen that BF$_4$ anion is present as a conjugate anion of quaternary ammonium salt. Even when preparing a catalyst with ligands having more quaternary ammonium salt units like complex 9, only the compound having four DNP ligands are observed even in the presence of a significantly excessive amount of NaDNP and even after a longer time. It is thought that an octahedral coordination compound having two Salen-phenoxy ligands and four DNP ligands is obtained in methylene chloride as a solvent, and formation of the octahedral compound causes the anion exchange. Cobalt (III) metal is classified into hard acid, and the hard acid prefers DNP to imine-base, resulting in the compound with such a different structure. In the case of complex 8, steric hindrance of t-butyl hinders formation of such a compound. The octahedral cobalt (III) compound in which cobalt has a charge of −3 is previously known [(a) Yagi, T.; Hanai, H.; Komorita T.; Suzuki T.; Kaizaki S. *J. Chem. Soc., Dalton Trans.* 2002, 1126. (b) Fujita, M.; Gillards, R. D. *Polyhedron* 1988, 7, 2731.]

Complexes 5, 9 and 10 provide $^1$H and $^{13}$C NMR spectrum and IR spectrum behaviors similar to complex 7, and thus may be regarded as a complex with a different coordination system having no imine coordination. Particularly, complex 5 has been regarded as a general Salen-compound structure having imine coordination like complex 8 in the previously known publication of the present inventors (*Angew. Chem. Int. Ed.*, 2008, 47, 7306-7309) and patent applications [Korean Patent Application No. 10-2008-0015454 (2008 Feb. 20, titled with "METHOD FOR RECOVERING CATALYST FROM COPOLYMER PREPARATION PROCESS", Bun Yeoul Lee, Sujith S, Eun Kyung Noh, Jae Ki Min, "A PROCESS PRODUCING POLYCARBONATE AND A COORDINATION COMPLEXES USED THEREFOR" PCT/KR2008/002453 (2008 Apr. 30); Sujith S, Jae Ki Min, Jong Eon Seong, Sung Jea Na, and Bun Yeoul Lee* "A HIGHLY ACTIVE AND RECYCLABLE CATALYTIC SYSTEM FOR $CO_2$/(PROPYLENE OXIDE)"]. However, it is found herein that complex 5 has such a different structure.

Complexes 6 and 11 provide $^1H$ and $^{13}C$ NMR spectrum and IR spectrum behaviors similar to complex 8, and thus may be regarded as a general Salen-compound structure having imine coordination.

(3) DFT calculation

Figure 6:
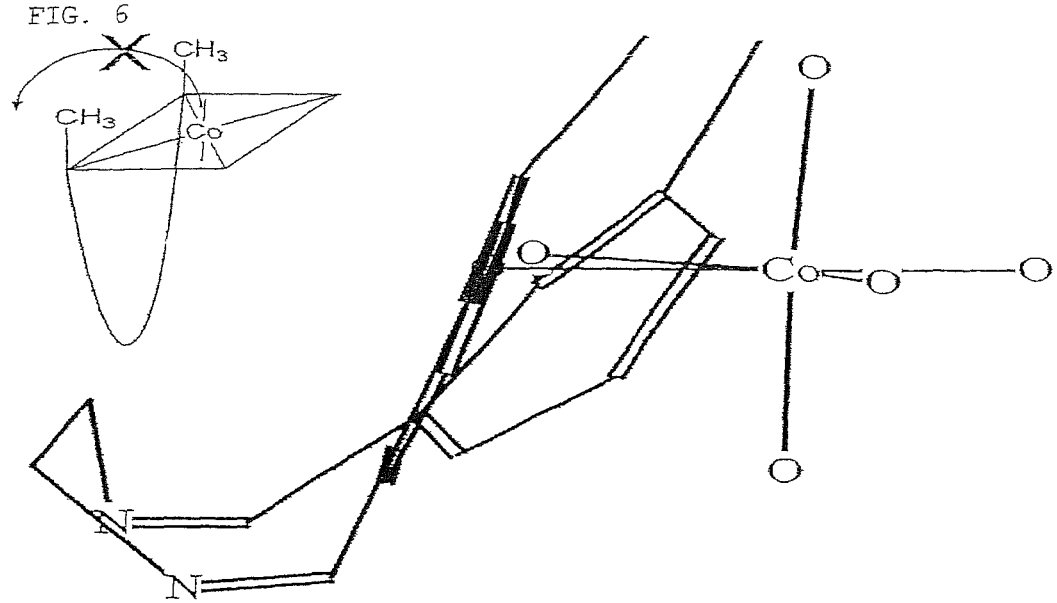
FIG. 6 shows the most stable conformation of compound 7 obtained by DFT calculation, wherein only the oxygen atoms of DNP ligands coordinated to the metal are shown for the purpose of simplicity.

DFT calculation is carried out to determine the structures and energy levels of complex 7 with a different coordination structure having no imine coordination, and another complex that are an isomer of complex 7 and have a general imine coordination structure, wherein two DNP ligands are coordinated at the axial site and the remaining two are present in a free state. FIG. 6 shows the most stable conformation of complex 7 obtained from the calculation. As can be seen from FIG. 6, complex 7 with a different structure having no imine coordination as disclosed herein has a more stable energy level than the general imine-coordinated structure by 132 kcal/mol. Such a difference in energy levels is significant.

(4) Movability of DNP Ligand

When observed from $^1H$ NMR in methylene chloride used in the last anion exchange reaction during the preparation of a catalyst, complexes 7, 9 and 10 show DNP signals at 8.4, 8.1 and 7.9 ppm with a [DNP]/[Salen-unit]integration ratio of 2.0 (FIG. 4). In other words, only two DNP ligands are observed among the four DNP ligands with the remaining two non-observed. This is because two DNP ligands undergo continuous conversion/reversion between the coordinated state and the non-coordinated state at a level of NMR time.

Figure 7:
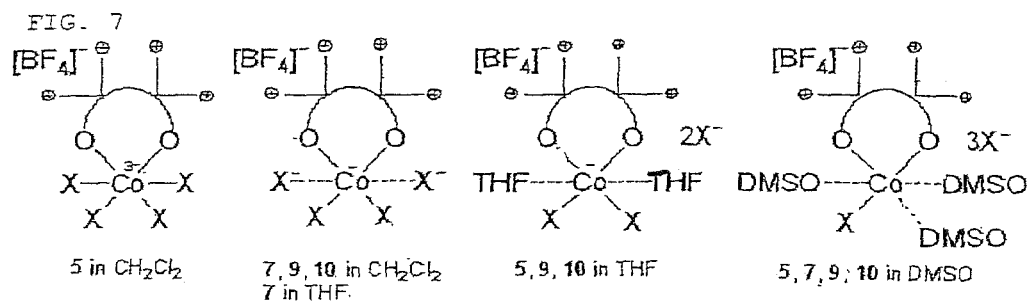
FIG. 7 is a reaction scheme illustrating a change in the state of DNP at room temperature depending on the solvent, in the case of a compound with a different coordination system having no coordination with imine (X=DNP).

On the other hand, in the case of complex 5, four DNP signals are observed at the same range. The DNP signals observed herein has a chemical shift greatly different from the chemical shift of $[Bu_4N]^+[DNP]^-$. Thus, it is though that the observed signals result from DNP coordinated in the complex. In other words, in the case of complexes 7, 9 and 10, two DNP ligands are coordinated and the remaining two undergo continuous conversion/reversion between the coordinated state and de-coordinated state in methylene chloride solvent at room temperature. In the case of complex 5, four DNP ligands are coordinated. FIG. 7 is a reaction scheme illustrating a change in the state of DNP at room temperature depending on the solvent, in the case of a compound with a different coordination system having no coordination with imine. As demonstrate by FIG. 7, the above statement that the complex obtained from the last anion exchange reaction has an octahedral coordination structure having two Salen-phenoxy ligands and four DNP ligands conforms to the structure adopted from the DFT calculation.

Figure 8:
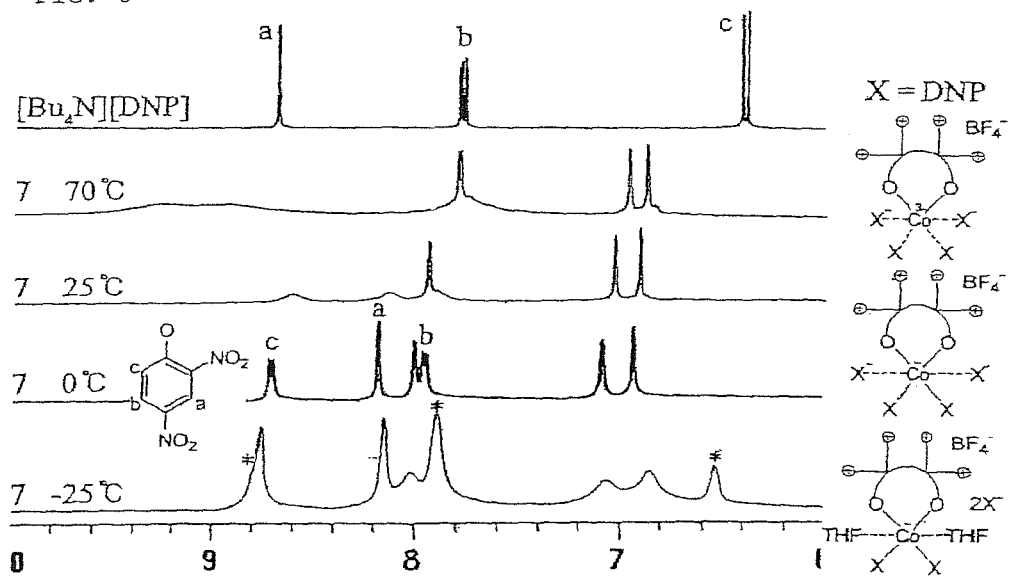
FIG. 8 shows VT $^1$H NMR spectrum of compound 7 in THF-$d_8$.

In addition, as observed from $^1H$ NMR spectrum of complex 7 measured in THF-$d_8$ at room temperature, signals corresponding to the two coordinated DNP ligands are observed at 8.6, 8.1 and 7.9 ppm (FIG. 4). When the temperature is reduced to 0° C., the signals become sharper and a signal coupling behavior is observed. The coordinated DNP signals may be more clearly understood by determining $^1H$-$^1H$ COSY NMR spectrum (FIG. 8). When the temperature is further reduced to −25° C., a new DNP signal is observed (marked with '*' in FIG. 8). The new signal has a similar chemical shift to $[Bu_4N]^+DNP^-$. Thus, the new signal may be regarded as DNP remaining in the de-coordinated state for a long time. At 70° C., four DNP ligands are observed as one set of broad signals at 9.3, 9.0 and 7.8 ppm. This is similar to the chemical shift of the coordinated DNP signal, and it is thought that all of the four DNP ligands remain in the coordinated state for a long time. In other words, as the temperature increases, DNP ligands may be more adjacent to the cobalt center. The de-coordinated DNP ligands are surrounded with solvent molecules, resulting in a decrease in entropy. Such de-coordination accompanied with a decrease in entropy is preferred at low temperature. Thus, de-coordinated signals are observed at reduced temperature, while a shift into the coordinated state is observed at high temperature. Similarly, a transition from a contact ion pair to a solvent separated ion pair at reduced temperature is well known [(a) Streitwieser Jr., A.; Chang, C. J.; Hollyhead, W. B.; Murdoch, J. R. *J. Am. Chem. Soc.* 1972, 94, 5288. (b) Hogen-Esch, T. E.; Smid, J. *J. Am. Chem. Soc.* 1966, 88, 307. (c) Lü, J.-M.; Rosokha, S. V.; Lindeman, S. V.; Neretin, I. S.; Kochi, J. K. *J. Am. Chem. Soc.* 2005, 127, 1797]. FIG. 8 shows VT $^1H$ NMR spectrum of compound 7 in THF-$d_8$.

Salen Complex 8 coordinated with imine shows highly different $^1H$ NMR spectrum in THF-$d_8$, as compared to complex 7. This demonstrates that complexes 7 and 8 have different structures. When reducing the temperature to 0° C., all DNP signals become broadened so that any signals may not be observed. At −25° C., a relatively sharp DNP signal set is observed at 8.1, 7.6 and 6.8 ppm with a [DNP]/[Salen-unit]integration ratio of 2.0. In addition, a significantly broad set of signals is observed at 8.9, 8.0 and 6.8 ppm, and these chemical shift values are similar to the chemical shift values (8.7, 8.0 and 6.8 ppm) of DNP remaining in the de-coordinated state for a long time as observed in complex 7. At −50° C., the two sets of signals become sharper so that two sets of DNP signals may be seen clearly. The DNP signals observed at 8.1, 7.6 and 6.8 ppm may correspond to two DNP ligands coordinated at the axial site of the conventional Salen coordination complex. Another set of signals observed at 8.9, 8.0 and 6.8 ppm may correspond to the de-coordinated state.

The state of DNP in THF at room temperature depending on the structure of ligand is demonstrated via $^1H$ NMR. In the case of complex 7, a set of signals of two coordinated DNP ligands is observed and the remaining two DNP ligands are not observed. This suggests that the two DNP ligands that are not observed herein undergo continuous conversion/reversion between the coordinated state and the de-coordinated state. On the other hand, in the cases of complexes 5, 9 and 10, two sets of signals, i.e., one set of two coordinated DNP signals and another set of signals of two DNP ligands remaining mainly in the de-coordinated state are observed. The signals of two DNP ligands remaining mainly in the de-coordinated state as observed in complexes 9 and 10 are broader than the corresponding signals in complex 5. This suggests that the two DNP ligands in complexes 9 and 10 remain in the de-coordinated state for a shorter time as compared to complex 5. As a result, the degree of retention (binding affinity to cobalt) of the two DNP ligands remaining mainly in the de-coordinated state is in order of 7>9 and 10>5.

As determined from $^1$H NMR spectrum of complexes 5, 7, 9 and 10 in DMSO-$d_6$ at 40° C., four DNP ligands are observed as a set of broad signals (FIG. 1). The chemical shift values of the signals (8.6, 7.8 and 6.4 ppm) are similar to the chemical shift values of [Bu$_4$N]$^+$DNP$^-$ (8.58, 7.80 and 6.35 ppm). Therefore, it can be said that the four DNP ligands remain mainly in the de-coordinated state at 40° C. However, such broad signals also suggest that the ligands undergo continuous conversion/reversion between the coordinated state and the de-coordinated state. At room temperature, another set of DNP signals are observed at 8.5, 8.1 and 7.8 ppm along with a set of signals of DNP ligands remaining mainly in the de-coordinated state with an integration ratio of 1:3. The less observed DNP signals have similar chemical shift values as compared to the chemical shift values of the coordinated DNP ligands observed in THF and methylene chloride. Thus, the signals may correspond to coordinated DNP ligands. In other words, in DMSO at room temperature, one DMP remains mainly in the coordinated state and the other three DMP ligands remain in the de-coordinated state. It is thought that DMSO is coordinated at the vacant site generated by de-coordination of DNP. DMSO is coordinated well to hard acid such as cobalt (III) metal.

(5) Complicated NMR Spectrometric Analysis Observed in DMSO-$d_6$

Figure 2:
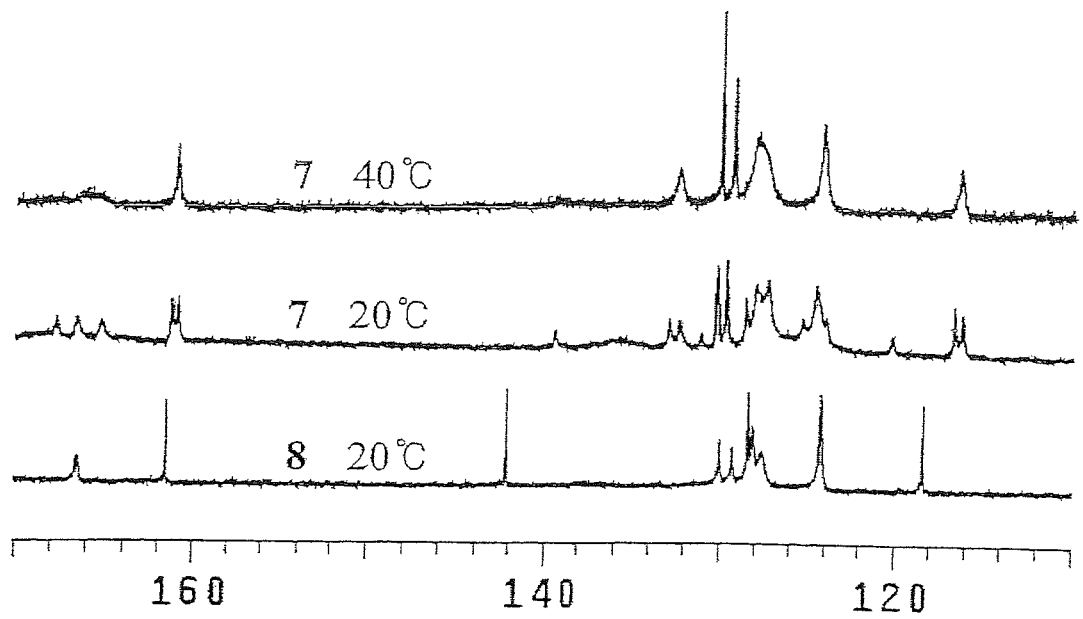
FIG. 2 shows $^{13}$C NMR spectra of compounds 7 and 8 in DMSO-$d_6$ as a solvent.
Figure 3:
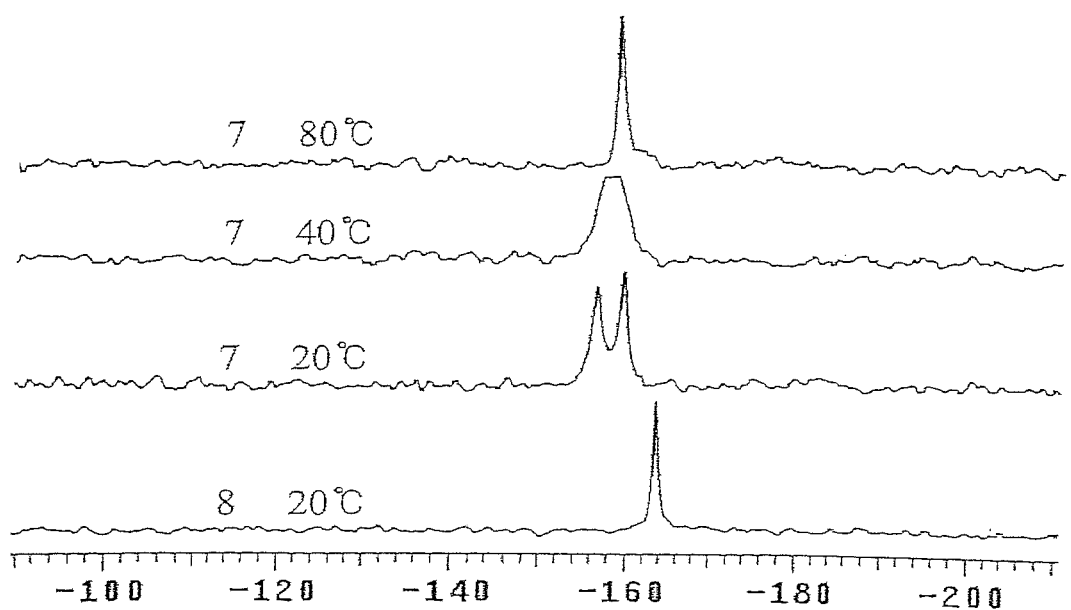
FIG. 3 shows $^{15}$N NMR spectra of compounds 7 and 8 in DMSO-$d_6$ as a solvent.

The complicated $^1$H, $^{13}$C and $^{15}$N NMR spectra of complex 7 observed in DMSO-$d_6$ may be understood through the above-described non-imine coordinated structure and the state of DNP. In the structure and state of complex 7 in DMSO at room temperature as shown in FIG. 7, two phenoxy ligands contained in one Salen-unit are subjected to different situations. One phenoxy ligand is at trans-position to DMSO, and the other is at trans-position to DNP. Therefore, two signals are observed in $^{15}$N NMR spectrum (FIG. 3), and a part of aromatic signals is divided at a ratio of 1:1 in $^1$H and $^{13}$C NMR (FIGS. 1 and 2). Especially, NCH$_2$CH$_2$N signal is divided into three signals at 4.3, 4.15 and 4.1 ppm with a ratio of 1:1:2. After the analysis through $^1$H-$^1$H COSY NMR spectrometry, it can be seen that three signals are derived from one NCH$_2$CH$_2$N-unit (FIG. 1). In the structure obtained by the DFT calculation, complex 7 shows a conformation of =NCH$_2$CH$_2$N=unit and is similar to the structure as illustrated in FIG. 6. In the above structure, complex 7 may not be converted into a structural isomer of the cobalt octahedral structure. Thus, the structure having three DMSO coordinations and one DNP coordination is chiral. Due to such chirality, two hydrogen atoms of N—CH$_2$ show NMR shift values at different positions. In the case of a complex with a chiral center, such as complex 5 or 10, $^1$H and $^{13}$C NMR spectra are more complicated. As the temperature increases to 40° C., two coordinated DNP signals disappear and one broad signal appears. In this case, the asymmetric coordination environment is broken and a simple Salen-ligand signal appears. Since the coordination environment around cobalt is symmetric in THF and CH$_2$Cl$_2$ at room temperature as shown in FIG. 7, a sharp Salen-ligand signal appears in $^1$H, $^{13}$C and $^{15}$N NMR.

(6) Cyclic Voltammetry (CV) Test

CV test also indirectly demonstrates that complexes 5 and 6 have different structures. If complexes 5 and 6 have the same structure, complex 5 having a methyl substituent is expected to cause reduction more easily. This is because methyl has lower electron donating property than t-butyl, and thus the cobalt center has less abundant electrons so that the electrons go into the cobalt center more easily. However, the opposite results are observed. Complex 5 with a methyl substituent causes reduction at a more negative potential than complex 6. It is observed that complexes 5 and 6 have a $E_{1/2}$ value of Co(III/II) of −0.076V and −0.013V, respectively, versus SCE. The difference, 63 mV, in reduction potentials between the two complexes is significant. A reduction potential difference of 59 mV from the Nernst equation [E=E°−(0.0592)log {[Ox]/[Red]}] means a difference in [Co(II)]/[Co(III)] ratios of 10 times at the same potential.

On the other hand, it is expected that complexes 12 and 13 having no DNP ligands have the same general imine-coordinated structure regardless of methyl or t-butyl substitution in a non-coordinatable solvent such as methylene chloride. After carrying out CV study with complexes 12 and 13 in methylene chloride, the two complexes show the same reduction potential (0.63 V vs. SCE). In other words, there is no difference in reduction potentials between methyl substitution and t-butyl substitution under the same structure. Thus, the above difference in reduction potentials suggests that the two complexes have different coordination systems. When the solvent is changed from CH$_2$Cl$_2$ to DMSO, the reduction potential difference appears again. The reduction potentials of complexes 12 and 13 observed in DMSO (−0.074 and −0.011 V vs. SCE) are similar to the reduction potentials of complexes 5 and 6 observed in DMSO (−0.076 and −0.013 V vs. SCE). Since DMSO is coordinated well to cobalt (III) metal, in DMSO as a solvent, complex 12 is converted into a complex with a different coordination system, such as complex 5 having no imine coordination, while four DMSO ligands are coordinated to complex 12 having a methyl substituent.

(7) Initiation Reaction

Figure 9:
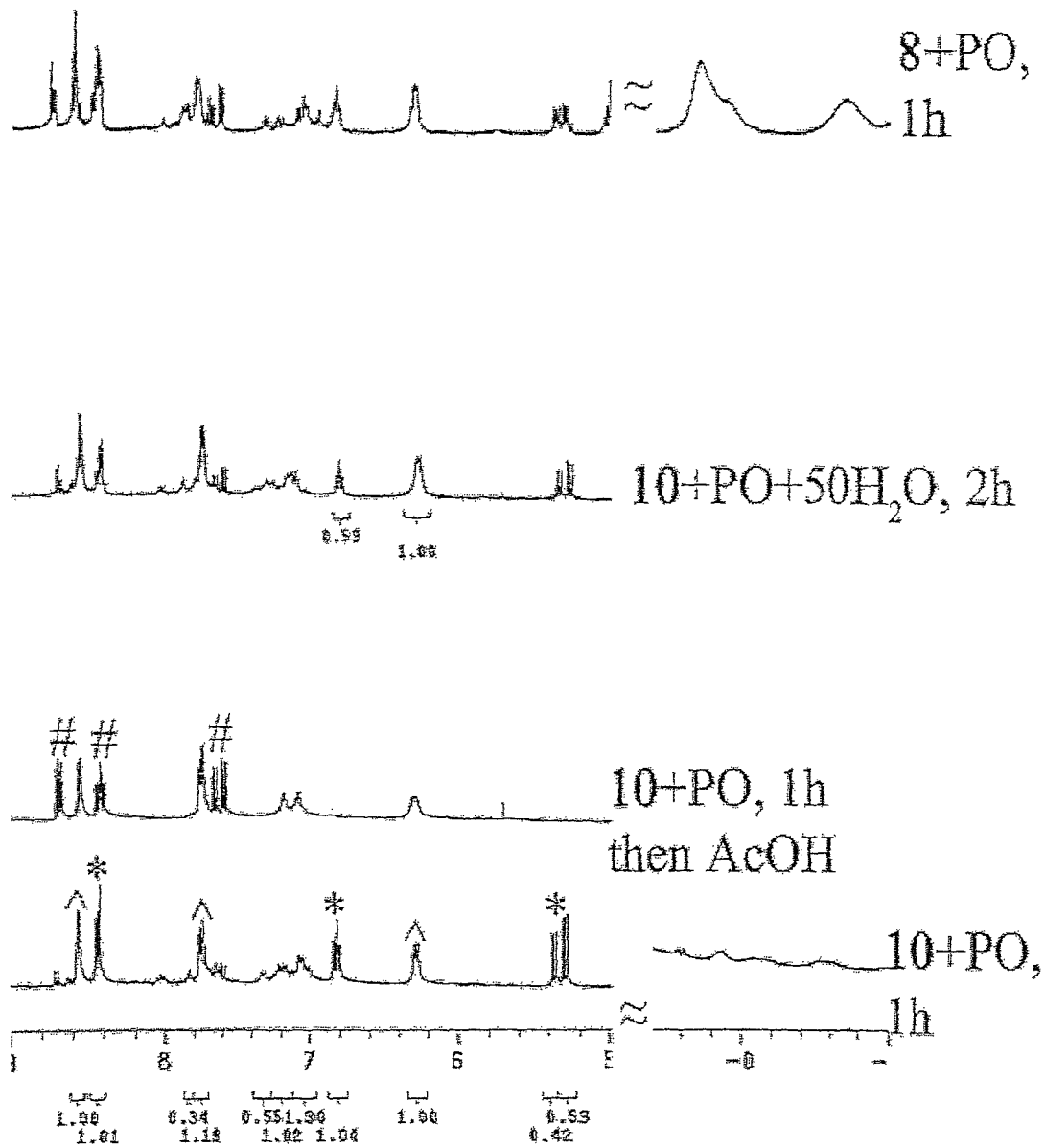
FIG. 9 is $^1$H NMR spectrum illustrating the reaction between compound 10 or 8 and propylene oxide, wherein the signals marked with "*" correspond to new signals derived from the anion of Meisenheimer salt.

Complex 10 reacts with propylene oxide. FIG. 9 is $^1$H NMR spectrum illustrating the reaction between complex 10 or 8 and propylene oxide. The signal marked with '*' is a newly generated signal that corresponds to the anion of Meisenheimer salt shown in complex 14. The oxygen atom of alkoxide obtained by the attack to propylene oxide coordinated with DNP further attacks ipso-position of the benzene ring, so that the anion of Meisenheimer salt is formed. Complicated aromatic signals of Salen are observed at 7.0-7.4 ppm. However, this is not caused by the breakage of the Salen-unit. When an excessive amount of acetic acid is added to the compound prepared after the reaction with propylene oxide, simple three Salen aromatic signals are observed. This suggests that the Salen-unit is not broken. The anion of Meisenheimer salt is stopped at a [Meisenheimer anion]/[DNP] integration ratio of 1:1. During the first one hour, DNP is converted rapidly into the anion of Meisenheimer salt so that the [Meisenheimer anion]/[DNP] integration ratio reaches 1:1. However, the conversion does not proceed any longer, and thus the integration ratio is unchanged even after 2 hours. The anion of Meisenheimer salt is a previously known compound [(a) Fendler, E. J.; Fendler, J. H.; Byrne, W. E.; Griff, C. E. *J. Org. Chem.* 1968, 33, 4141. (b) Bernasconi, C. F.; Cross, H. S. *J. Org. Chem.* 1974, 39, 1054)]. Conversion of DNP into the anion of Meisenheimer salt is significantly lowered in the presence of a certain amount of water. When 5 equivalents of water are present per equivalent of cobalt, the conversion rate is not significantly changed. However, introduction of 50 equivalents of water causes a rapid drop in the conversion rate, so that the [Meisenheimer anion]/[DNP] integration ratio becomes 0.47 after 1 hour, becomes 0.53 after 2 hours, and remains at 0.63 even after 4 hours while not providing complex 14 (FIG. 8).

The reactivity of the general imine-coordinated complex 8 with propylene oxide is different from that of the non-imine coordinated complex 10. Although the same anion of Meisenheimer salt is observed, the [Meisenheimer anion]/[DNP] integration ratio is not stopped at 1.0 but gradually increases over time (0.96 after 1 hour; 1.4 after 2 hours; 1.8 after 7 hours; and 2.0 after 20 hours). Further, unlike the behavior of complex 10, complex 8 shows a relatively large amount of broad signals between −1 ppm and 0.5 ppm. This suggests that reduction into a paramagnetic cobalt (II) compound occurs. The broad signal gradually increases over time. The cobalt (II) compound has no catalytic activity.

Example 15

Preparation of Carbon Dioxide/Propylene Oxide Copolymer (a) Copolymerization Using Complexes of Examples 3-10 as Catalyst To a 50 mL bomb reactor, any one complex obtained from Examples 3-10 (used in an amount calculated according to a ratio of monomer/catalyst of 7.58) and propylene oxide (10.0 g, 172 mmol) are introduced in a dry box and the reactor is assembled. As soon as the reactor is removed from the dry box, carbon dioxide is introduced under a pressure of 18 bar, the reactor is introduced into an oil bath controlled previously to a temperature of 80° C. and agitation is initiated. The time at which carbon dioxide pressure starts to be decreased is measured and recorded. After that, the reaction is carried out for 1 hour, and then carbon dioxide gas is depressurized to terminate the reaction. To the resultant viscous solution, monomers (10 g) are further introduced to reduce the viscosity. Then, the resultant solution is passed through a silica gel column [400 mg, Merck, 0.040-0.063 mm particle diameter (230-400 mesh)] to obtain a colorless solution. The monomers are removed by depressurization under reduced pressure to obtain a white solid. The weight of the resultant polymer is measured to calculate turnover number (TON). The polymer is subjected to $^1$H NMR spectrometry to calculate selectivity. The molecular weight of the resultant polymer is measured by GPC with calibration using polystyrene standards.

(b) Copolymerization Using Complex of Example 13 as Catalyst

To a 50 mL bomb reactor, complex 40a (6.85 mg, 0.0030 mmol, monomer/catalyst ratio=50,000) obtained from Example 13 and propylene oxide (9.00 g, 155 mmol) are introduced and the reactor is assembled. The reactor is introduced into an oil bath controlled previously to a temperature of 80° C. and is agitated for about 15 minutes so that the reactor temperature is in equilibrium with the bath temperature. Next, carbon dioxide is added under 20 bars. After 30 minutes, it is observed that carbon dioxide is depressurized while the reaction proceeds. Carbon dioxide is further injected continuously for 1 hour under 20 bars. To the resultant viscous solution, monomers (10 g) are further introduced to reduce the viscosity. Then, the resultant solution is passed through a silica gel column [400 mg, Merck, 0.040-0.063 mm particle diameter (230-400 mesh)] to obtain a colorless solution. The monomers are removed by depressurization under reduced pressure to obtain 2.15 g of a white solid. The catalytic activity of the complex used in this Example corresponds to a TON of 6100 and a turnover frequency (TOF) of 9200 h$^{-1}$. The resultant polymer has a molecular weight (Mn) of 89000 and a polydispersity (Mw/Mn) of 1.21 as measured by GPC. The polymer formation selectivity is 96% as determined by $^1$H NMR.

Example 16

Recovery of Copolymer and Catalyst

In the cases of complexes 5, 7 and 10, the following process is used to recover catalysts. The colored portion containing a cobalt catalyst component at the top of the silica column in Example 12 is collected, and dispersed into methanol solution saturated with NaBF$_4$ to obtain a red colored solution. The red solution is filtered, washed twice with methanol solution saturated with NaBF$_4$ until the silica becomes colorless, the resultant solution is collected, and the solvent is removed by depressurization under reduced pressure. To the resultant solid, methylene chloride is added. In this manner, the brown colored cobalt compound is dissolved into methylene chloride, while the unsoluble white NaBF$_4$ solid may be separated. To the methylene chloride solution, 2 equivalents of solid 2,4-dinitrophenol and 4 equivalents of sodium 2,4-dinitrophenolate are introduced per mole of the catalyst, followed by agitation overnight. The resultant mixture is filtered to remove methylene chloride solution and to obtain brown colored powder. After $^1$H NMR analysis, the resultant compound is shown to be the same as the catalyst compound and to have similar activity in the copolymerization.

Table 1 shows the polymerization reactivity of each catalyst.

TABLE 1

Polymerization reactivity of each catalyst[a]

| No. | Catalyst | Induction Time (min) | TOF[b] | Selectivity[c] | $M_n^d$ (10$^{-3}$) | $M_w/M_n$ |
|---|---|---|---|---|---|---|
| 1 | 5 | 60[e] | 13,000 | 92 | 210 | 1.26 |
| 2 | 6 | 0 | 1,300 | 84 | 38 | 2.34 |
| 3 | 7 | 120[e] | 8,300 | 97 | 113 | 1.23 |
| 4 | 8 | 0 | 5,000 | 85 | 120 | 1.41 |
| 5 | 9 | | 0 | | | |
| 6 | 10 | 260[e] | 11,000 | 96 | 140 | 1.17 |
| 7 | 11 | | 0 | | | |
| 8 | 14 | 30 | 13,000 | 99 | 170 | 1.21 |
| 9 | 15 | 0 | 15,000 | 99 | 270 | 1.26 |
| 10[f] | 15 | 0 | 16,000 | 99 | 300 | 1.31 |

[a]Polymerization condition: PO (10 g, 170 mmol), [PO]/[Cat] = 100,000, CO$_2$ (2.0-1.7 MPa), temperature 70-75° C., reaction time 60 minutes.
[b]calculated based on the weight of the polymer containing cyclic carbonate.
[c]calculated by $^1$H NMR.
[d]measured by GPC using polystyrene standards.
[e]induction time of 1-10 hours depending on batch.
[f]polymerization using 220 g of PO.

As can be seen from Table 1, the general compounds having imine coordination, i.e. complexes 6, 8 and 11 has little or no polymerization activity. On the other hand, the complexes with a different structure having no imine coordination according to the present invention have high polymerization activity. However, complex 9 with a different structure having no imine coordination but containing six ammonium units has no activity.

Complexes 5, 7 and 10 have higher activity in order of 5>10>7, which is the converse of order of Co-binding affinity of weak bound DNP undergoing continuous conversion/reversion between the Co-coordinated state and the de-coordinated state.

Complex 10 is used to perform many experiments. Under a high-temperature high-humidity condition in the summer season, a great change is observed in induction time (1-12 hours). After the induction time, polymerization rate are observed to be nearly constant (TOF, 9,000-11,000 h$^{-1}$). In the summer season, the amount of water infiltrating into the dry box for a polymerization reactor is not negligible. In this case, the polymerization system absorbs water and the induction time varies with the amount of water. In fact, under a dry low-temperature condition in the winter season, induction time decreases to 1 hour. In this case, when an additional amount of water is added thereto (50 equivalents vs. cobalt), induction time increases to 3 hours (entry 10). Introduction of a significant amount of water (250 equivalents) does not allow polymerization.

When a certain amount of water is present, the rate of polymerization initiation caused by an attack of DNP to propylene oxide is decreased significantly, as determined by NMR (FIG. 9). When using compound 15 obtained from the reaction with propylene oxide as a catalyst, it is possible to solve the problem of such a great change in induction time depending on the amount of water (entry 13). When using compound 15 as a catalyst, water sensitivity decreases to allow polymerization even under a [propylene oxide]/[catalyst] ratio of 150000:1, resulting in further improvement in TON (entry 14). Under such a condition, complex 10 has no polymerization activity even when using thoroughly purified propylene oxide. Compound 15 is obtained by dissolving a high concentration of complex 10 into propylene oxide and by performing a reaction for 1 hour. In this case, it is possible to neglect the ratio of [water remaining in propylene oxide]/[compound 10].

The present application contains subject matter related to Korean Patent Application Nos. 10-2008-0074435, 10-2008-0126170, 10-2009-0054481 and 10-2009-0054569 filed in the Korean Intellectual Property Office on Jul. 30, 2008, Dec. 11, 2008, Jun. 18, 2009, and Jun. 18, 2009, the entire contents of which are incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. A method for preparing polycarbonate, comprising carrying out copolymerization of an epoxide compound with carbon dioxide using a complex represented by Chemical Formula 6:

[Chemical Formula 6]

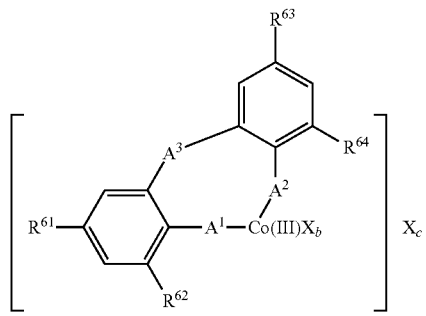

wherein
$A^1$ and $A^2$ independently represent an oxygen or sulfur atom;
Xb and Xc independently represents 2,4-dinitrophenolate or $BF_4^-$;
$R^{62}$ and $R^{64}$ are independently selected from tert-butyl, methyl, ethyl, isopropyl and hydrogen, and $R^{61}$ and $R^{63}$ independently represent —[CH{(CH$_2$)$_3$N$^+$Bu$_3$}$_2$] or —[CMe{(CH$_2$)$_3$N$^+$Bu$_3$}$_2$];
b+c−1 represents 4; and
$A^3$ represents —CH=N-Q-N=CH— and Q represents trans-1,2-cyclohexylene or ethylene as a catalyst.

2. The method according to claim 1, wherein the epoxide compound is selected from the group consisting of (C2-C20) alkylene oxide substituted or unsubstituted by a halogen or alkoxy; (C4-C20) cycloalkylene oxide substituted or unsubstituted by a halogen or alkoxy; and (C8-C20) styrene oxide substituted or unsubstituted by a halogen, alkoxy, alkyl or aryl.

3. A method for preparing polycarbonate, comprising carrying out copolymerization of an epoxide compound with carbon dioxide using a complex represented by Chemical Formula 6:

[Chemical Formula 6]

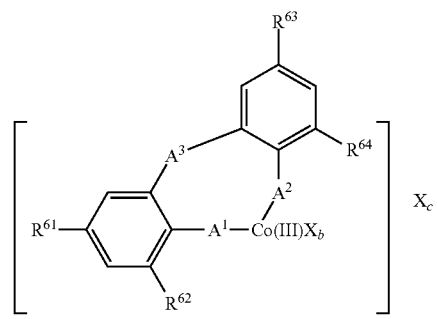

wherein
$A^1$ and $A^2$ independently represent an oxygen or sulfur atom; one of Xb and Xc represents $BF_4^-$, two of them represent 2,4-dinitrophenolate, and the remaining two are anions represented by Chemical Formula 10;
$R^{62}$ and $R^{64}$ are independently selected from tert-butyl, methyl, ethyl, isopropyl and hydrogen, and $R^{61}$ and $R^{63}$ independently represent —[CH{(CH$_2$)$_3$N$^+$Bu$_3$}$_2$] or —[CMe{(CH$_2$)$_3$N$^+$Bu$_3$}$_2$];
b+c−1 represents 4; and
$A^3$ represents —CH=N-Q-N=CH— and Q represents trans-1,2-cyclohexylene or ethylene as a catalyst,

[Chemical Formula 10]

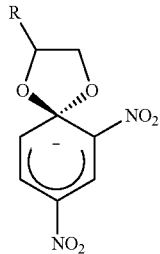

wherein
R represents methyl or H.

* * * * *